United States Patent
Bifulco, Jr. et al.

(10) Patent No.: US 10,000,490 B2
(45) Date of Patent: Jun. 19, 2018

(54) INHIBITORS OF THE FIBROBLAST GROWTH FACTOR RECEPTOR

(71) Applicant: BLUEPRINT MEDICINES CORPORATION, Cambridge, MA (US)

(72) Inventors: Neil Bifulco, Jr., Sudbury, MA (US); Lucian V. DiPietro, Gloucester, MA (US); Chandrasekhar V. Miduturu, Cambridge, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days. days.

(21) Appl. No.: 15/599,006

(22) Filed: May 18, 2017

(65) Prior Publication Data

US 2017/0253593 A1 Sep. 7, 2017

Related U.S. Application Data

(62) Division of application No. 14/596,987, filed on Jan. 14, 2015.

(60) Provisional application No. 61/927,793, filed on Jan. 15, 2014.

(51) Int. Cl.

| C07D 487/04 | (2006.01) |
|---|---|
| C07D 471/04 | (2006.01) |
| C07D 403/04 | (2006.01) |
| A61K 31/517 | (2006.01) |
| A61P 35/00 | (2006.01) |
| C07D 413/04 | (2006.01) |
| C07D 239/74 | (2006.01) |
| C07D 217/16 | (2006.01) |
| C07D 217/14 | (2006.01) |
| C07D 487/14 | (2006.01) |

(52) U.S. Cl.
CPC .......... *C07D 471/04* (2013.01); *A61K 31/517* (2013.01); *C07D 217/14* (2013.01); *C07D 217/16* (2013.01); *C07D 239/74* (2013.01); *C07D 403/04* (2013.01); *C07D 413/04* (2013.01); *C07D 487/04* (2013.01); *C07D 487/14* (2013.01)

(58) Field of Classification Search
CPC .......................... C07D 487/04; A61K 31/4353
USPC .................... 546/122; 514/300, 313
See application file for complete search history.

(56) References Cited

U.S. PATENT DOCUMENTS

| 6,605,615 | B2 | 8/2003 | Medina et al. |
|---|---|---|---|
| 6,936,612 | B2 | 8/2005 | Barvian et al. |
| 8,802,697 | B2* | 8/2014 | Bifulco, Jr. .......... C07D 239/42 514/264.11 |
| 9,034,898 | B2 | 5/2015 | Sanofi |
| 9,126,951 | B2* | 9/2015 | Bifulco, Jr. .......... C07D 239/42 |
| 9,200,002 | B2 | 12/2015 | Hodous et al. |
| 9,266,883 | B2 | 2/2016 | Buschmann et al. |
| 9,321,786 | B2 | 4/2016 | D'Agostino et al. |
| 9,334,263 | B2 | 5/2016 | Hodous et al. |
| 9,340,514 | B2* | 5/2016 | Bifulco, Jr. .......... C07D 239/42 |
| 9,434,700 | B2 | 9/2016 | Bifulco, Jr. et al. |
| 9,499,522 | B2 | 11/2016 | DiPietro et al. |
| 9,533,988 | B2 | 1/2017 | Buschmann et al. |
| 9,688,680 | B2 | 6/2017 | Hodous |
| 9,695,165 | B2 | 7/2017 | Bifulco, Jr. et al. |
| 9,745,311 | B2 | 8/2017 | Lu et al. |
| 2005/0124562 | A1 | 6/2005 | Guiles et al. |
| 2013/0035366 | A1 | 2/2013 | Swayze et al. |
| 2013/0150342 | A1 | 6/2013 | Brain et al. |
| 2014/0187559 | A1 | 7/2014 | Miduturu |
| 2016/0002223 | A1 | 1/2016 | Chekal et al. |
| 2016/0102097 | A1 | 4/2016 | Hodous et al. |
| 2016/0115164 | A1 | 4/2016 | Wu et al. |
| 2017/0022206 | A1 | 1/2017 | Hodous et al. |
| 2017/0029409 | A1 | 2/2017 | DiPietro et al. |
| 2017/0057953 | A1 | 3/2017 | Hodous et al. |
| 2017/0066773 | A1 | 3/2017 | Wenglowsky et al. |
| 2017/0066812 | A1 | 3/2017 | Bifulco, Jr. et al. |
| 2017/0121312 | A1 | 5/2017 | Brubaker et al. |
| 2017/0145018 | A1 | 5/2017 | Wenglowsky et al. |
| 2017/0174652 | A1 | 6/2017 | Bifulco, Jr. et al. |
| 2017/0204104 | A1 | 7/2017 | Hodous et al. |
| 2017/0267661 | A1 | 9/2017 | Kim et al. |
| 2017/0298069 | A1 | 10/2017 | Brooijmans et al. |

FOREIGN PATENT DOCUMENTS

| EP | 1 836 174 B1 | 2/2013 |
|---|---|---|
| EP | 2 657 233 A1 | 10/2013 |
| JP | 2004-519422 A | 7/2004 |
| JP | 2011-526299 A | 10/2011 |
| JP | 2012-501654 A | 1/2012 |
| JP | 2014-513729 A | 6/2014 |

(Continued)

OTHER PUBLICATIONS

"Chemotherapy of Neoplastic Diseases" in, *Goodman & Gilman's: The Pharmacological Basis of Therapeutics*. 11th ed., L.L. Brunton et al. (Eds.), The McGraw Hill Cos., 2008; pp. 853-908.

Antczak, C. et al. (2009) "Structure-activity relationships of 6-(2,6-dichlorophenyl)-8-methyl-2-(phenylamino)pyrido[2,3-d]pydimidin-7-ones: Toward selective Abl inhibitors" *Bioorg Med Chem Lett*, 19:6872-6876.

Bennett, J.C. and F. Plum (Eds.) (1996) *Cecil Textbook of Medicine*. 20th Edition, vol. 1. W.B. Saunders Co.; pp. 1004-1010.

(Continued)

*Primary Examiner* — Venkataraman Balasubramanian
(74) *Attorney, Agent, or Firm* — Finnegan, Henderson, Farabow, Garrett & Dunner, LLP

(57) ABSTRACT

Described herein are inhibitors of FGFR-4, pharmaceutical compositions including such compounds, and methods of using such compounds and compositions to inhibit the activity of FGFR-4.

12 Claims, No Drawings

(56) References Cited

FOREIGN PATENT DOCUMENTS

| | | |
|---|---|---|
| WO | WO 96/015128 A2 | 5/1996 |
| WO | WO 01/29013 A1 | 4/2001 |
| WO | WO 01/38315 A1 | 5/2001 |
| WO | WO 01/64646 A2 | 9/2001 |
| WO | WO 02/12238 A2 | 2/2002 |
| WO | WO 02/076985 A1 | 10/2002 |
| WO | WO 2004/063195 A1 | 7/2004 |
| WO | WO 2005/030131 A2 | 4/2005 |
| WO | WO 2006/039718 A2 | 4/2006 |
| WO | WO 2008/079988 A2 | 7/2008 |
| WO | WO 2009/046448 A1 | 4/2009 |
| WO | WO 2009/158571 A1 | 12/2009 |
| WO | WO 2010/026291 A1 | 3/2010 |
| WO | WO 2010/028236 A1 | 3/2010 |
| WO | WO 2010/076238 A1 | 7/2010 |
| WO | WO 2011/016528 A1 | 2/2011 |
| WO | WO 2011/034907 A2 | 3/2011 |
| WO | WO 2011/101409 A1 | 8/2011 |
| WO | WO 2011/135376 A1 | 11/2011 |
| WO | WO 2012/158843 A2 | 11/2012 |
| WO | WO 2013/179034 A1 | 12/2013 |
| WO | WO 2014/011900 A2 | 1/2014 |
| WO | WO 2014/944846 A1 | 3/2014 |
| WO | WO 2014-128588 A1 | 8/2014 |
| WO | WO 2014/144737 A1 | 9/2014 |
| WO | WO 2015/057963 A1 | 4/2015 |
| WO | WO 2015/061572 A1 | 4/2015 |
| WO | WO 2015/957938 A1 | 4/2015 |
| WO | WO 2015/105992 A1 | 7/2015 |
| WO | WO 2016/064960 A1 | 4/2016 |
| WO | WO 2016/134294 A1 | 8/2016 |
| WO | WO 2016/134314 A1 | 8/2016 |
| WO | WO 2016/134320 A1 | 8/2016 |
| WO | WO 2017/070708 A1 | 4/2017 |

OTHER PUBLICATIONS

Brown, A.P. et al. (2005) "Cartilage Dysplasia and Tissue Mineralization in the Rat Following Administration of a FGF Receptor Tyrosine Kinase Inhibitor" *Toxicologic Pathology*, 33:449-455.

Bruix, J. et al. (2016) "Efficacy and safety of regorafenib versus placebo in patients with hepatocellular carcinoma (HCC) progressing on sorafonib: results of the international, randomized phase 3 RESORCE trial" *Annals of Oncology*, 27(Suppl 2):ii140-ii141, Abstract LBA-03.

Brunton, L. et al (Eds) (2008) "Chemotherapy of Neoplastic Diseases" in *Goodman & Gilman's: Manual of Pharmacology and Therapeutics*. New York: McGraw-Hill Medical; pp. 853-908.

Cao, L. et al. (2010) "Genome-Wide Identification of PAX3-FKHR Binding Sites in Rhabdomyosarcoma Reveals Candidate Target Genes Important for Development and Cancer" *Cancer Research*, 70(16):6497-6508.

Carmi, C. et al. (2012) "Irreversible inhibition of epidermal growth factor receptor activity by 3-aminopropanamides" *J Med Chem*, 55(5):2251-2264.

Cheng, A.L. et al. (2009) "Efficacy and safety of sorafenib in patients in the Asia-Pacific region with advanced hepatocellular carcinoma: a phase III randomised, double-blind, placebo-controlled trial" *Lancet Oncol*, 10(1):25-34.

Chiang, D.Y. et al. (2008) "Focal Gains of VEGFA and Molecular Classification of Hepatocellular Carcinoma" *Cancer Res*, 68(16):6779-6788.

Cohen, P. (1999) "The development and therapeutic potential of protein kinase inhibitors" *Current Opinions in Chemical Biology*, 3(4):459-465.

Dermer, G. (Mar. 1994) "Another Anniversary for the War on Cancer" *Bio/Technology*, 12:320.

Dieci, M.V. et al. (2013) "Fibroblast Growth Factor Receptor Inhibitors as a Cancer Treatment: From a Biologic Rationale to Medical Perspectives" *Cancer Disc*, 3:264-279.

Ding, L. et al. (Oct. 23, 2008) "Somatic mutations affect key pathways in lung adenocarcinoma" *Nature*, 455:1069-1075.

Freshney, R. et al. (1983) *Culture of Animal Cells, A Manual of Basic Techniques*. Alan R Liss, Inc., pp. 1-6.

Gao, H. et al. (2015) "High-throughput screening using patient-derived tumor xenografts to predict clinical trial drug response" *Nature Medicine*, 21(11)1318-1325.

Golub, T.R. et al. (1999) "Molecular Classification of Cancer: Class Discovery and Class Prediction by Gene Expression Monitoring" *Science*, 286:531-537.

Guagnano, V. et al. (2011) "Discovery of 3-(2,6-Dichloro-3,5-dimethoxy-phenyl)-1-(6-[4-(4-ethyl-piperazin-1-yl)-phenylamino]-pyrimidin-4-yl)-1 methyl-urea (NVP-BGJ398), A Potent and Selective Inhibitor of the Fibroblast Growth Factor Receptor Family of Receptor Tyrosine Kinase" *J Med Chem*, 54:7066-7083.

Hagel, M et al. (2015) "First Selective Small Molecule inhibitor of FGFR4 for the Treatment of Hepatocellular Carcinomas with an Activated FGFR4 Signaling Pathway" *Cancer Discovery*, 5(4):425-437.

Ho, H.K. et al. (2009) "Fibroblast growth factor receptor 4 regulates proliferation, anti-apoptosis and alpha-fetoprotein secretion during hepatocellular carcinoma progression and represents a potential target for therapeutic intervention" *Journal of Hepatology*, 50:118-127.

Ho, H.K. et al. (2013) "Developing FGFR4 Inhibitors As Potential Anti-Cancer Agents Via In Silico Design, Supported by In Vitro and Cell-Based Testing" *Curr Med Chem*, 20:1203-1217.

International Search Report and Written Opinion for International Application No. PCT/US2013/050106, dated Jan. 10, 2014.

International Search Report and Written Opinion for International Application No. PCT/US2014/061974, dated Dec. 23, 2014.

International Search Report and Written Opinion for International Application No. PCT/US2015/011424, dated May 29, 2015.

Jain, V.K. and N.C. Turner (2012) "Challenges and opportunities in the targeting of fibroblast growth factor receptors in breast cancer" *Breast Cancer Research*, 14:208 (9 pages).

Kamb, A. (1998) "Cyclin-dependent kinase inhibitors and human cancer" *Curr Top Microbiol Immunol*, 227:139-148.

Katoh, Y. and M. Katoh (2009) "FGFR2-related pathogenesis and FGER2-targeted therapeutics" *Int'l J Mol Med*, 23:307-311.

Kelland, L.R. (2004) "'Of mice and men': values and liabilities of the athymic nude mouse model in anticancer drug development" *Eur J Cancer*, 40:827-836.

Lehàr, J. et al. (2009) "Synergistic drug combinations tend to improve therapeutically relevant selectivity" *Nat Biotechnol*, 27(7):659-666. HHS Public Access Author Manuscript; available in PMC Jan. 1, 2010 (23 pages).

Leproult, E. et al. (2011) "Cysteine Mapping in Conformationally Distinct Kinase Nucleotide Binding Sites: Application to the Design of Selective Covalent Inhibitors" *J Med Chem*, 54(5):1347-1355.

Liang, G. et al. (2013) "Small molecule inhibition of fibroblast growth factor receptors in cancer" *Cytokine & Growth Factor Reviews*, 24:467-475.

Llovet, J. et al. (2008) "Sorafenib in advanced hepatocellular carcinoma" *N Eng J Med*, 359:378-390.

Neidle, S. et al. (eds). (2008) *Cancer Drug Design and Discovery*. Elsevier/Academic Press; pp. 427-431.

Notice of Allowance dated Sep. 26, 2017, in U.S. Appl. No. 15/093,354, filed Apr. 7, 2016, by Blueprint Medicines Corp.

Notice of Allowance dated Sep. 5, 2017, in U.S. Appl. No. 15/217,503, filed Jul. 22, 2016, by Blueprint Medicines Corp.

Notice of Allowance dated Oct. 25, 2017, in U.S. Appl. No. 15/340,428, filed Nov. 1, 2016, by Blueprint Medicines Corp.

Roidl, A. et al. (2010) "The FGFR4 Y3670 mutant is a dominant oncogene in MDA-MB453 breast cancer cells" *Oncogene*, 29:1543-1552.

Sawey, E.T. et al. (Mar. 2011) "Identification of a Therapeutic Strategy Targeting Amplified *FGF19* in Liver Cancer by Oncogenomic Screening" *Cancer Cell* 19:347-358.

Taylor, J.G. et al. (Nov. 2009) "Identification of *FGFR4*-activating mutations in human rhabdomyosarcomas that promote metastasis in xenotranspianted models" *J Clin Invest*, 119(11):3395-3407.

(56) References Cited

OTHER PUBLICATIONS

Torre, L.A. et al. (2015) "Global Cancer Statistics, 2012" *CA Cancer J Clin*, 65:87-108.
U.S. Appl. No. 15/548,925, filed Aug. 4, 2017, by Blueprint Medicines Corp.
U.S. Appl. No. 15/657,057, filed Jul. 21, 2017, by Blueprint Medicines Corp.
U.S. Appl. No. 15/660,640, Bed Jul. 26, 2017, by Blueprint Medicines Corp.
Vergnes, L. et al. (Jun. 2013) "Diet1 Functions in the FGE15/19 Enterohepatic Signaling Axis to Modulate Bile Acid and Lipid Levels" *Cell Metabolism*, 17:916-928.
Wu, D. et al. (2008) "A solid-phase Bcr-Abl kinase assay in 96-well hydrogel plates" *Analytical Biochemistry*, 375:18-26.
Wu, X et al. (2010) "FGF19-induced Hepatocyte Proliferation is Mediated through FGFR4 Activation" *J Biol Chem*, 285:5165-5170.
Zaid, T.M. et al. (Feb. 2013) "Identification of FGFR4 as a Potential Therapeutic Target for Advanced-Stage, High-Grade Serous Ovarian Cancer" *Clinical Cancer Research*, 19(4):809-820.
Zhou, W. et al. (Mar. 2010) "A Structure-Guided Approach to Creating Covalent FGFR Inhibitors" *Chemistry & Biology*, 17(3):285-295.

\* cited by examiner

INHIBITORS OF THE FIBROBLAST GROWTH FACTOR RECEPTOR

CLAIM OF PRIORITY

This application is a divisional of U.S. Ser. No. 14/596,987, filed on Jan. 14, 2015, which claims priority to U.S. Ser. No. 61/927,793, filed on Jan. 15, 2014, each of which is hereby incorporated by reference in its entirety.

FIELD OF THE INVENTION

Described herein are compounds, pharmaceutical compositions, and methods of using such compounds and compositions to inhibit the activity of FGFR-4.

BACKGROUND

Fibroblast growth factor receptor 4 (FGFR-4) is a protein that in humans is encoded by the FGFR-4 gene. This protein is a member of the fibroblast growth factor receptor family, where amino acid sequence was highly conserved between members throughout evolution. FGFR family members 1-4 differ from one another in their ligand affinities and tissue distribution. A full-length representative protein consists of an extracellular region composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. The genomic organization of the FGFR-4 gene encompasses 18 exons. Although alternative splicing has been observed, there is no evidence that the C-terminal half of the IgIII domain of this protein varies between three alternate forms, as indicated for FGFR 1-3.

Ectopic mineralization, characterized by inappropriate calcium-phosphorus deposition in soft tissue, has been observed in rats treated with an FGFR-1 inhibitor (Brown, A P et al. (2005), Toxicol. Pathol., p. 449-455). This suggests that selective inhibition of FGFR-4 without inhibition of other isoforms of FGFR, including FGFR-1, may be desirable in order to avoid certain toxicities. FGFR-4 preferentially binds fibroblast growth factor 19 (FGF19) and has recently been associated with the progression of certain sarcomas, renal cell cancer, breast cancer, and liver cancer.

SUMMARY OF THE INVENTION

Described herein are inhibitors of FGFR-4. Further described herein are pharmaceutical compositions and pharmaceutical formulations that include an inhibitor of FGFR-4.

In one aspect, the invention features a compound of Formula I, or pharmaceutically acceptable salt thereof, wherein:

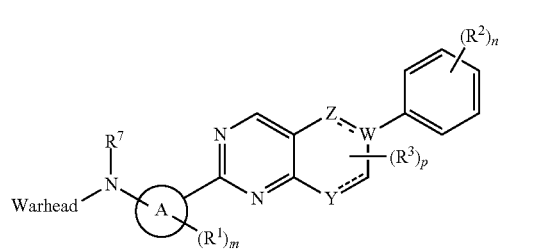

Formula I denotes a single or double bond;
Warhead is a moiety capable of forming a covalent bond with a nucleophile;
Ring A is a 5-8 membered aryl, 5-12 membered heteroaryl, 3-7 member heterocyclyl or 3-12 membered cycloalkyl group;
W is C or N, X and Z are each independently CH or N;
Y is CH or N—$R^4$ wherein $R^4$ is H, $C_{1-6}$ alkyl, or 3-12 membered cycloalkyl;
each of $R^1$-$R^3$ is, independently, halo, cyano, optionally substituted $C_{1-6}$ alkyl, optionally substituted $C_{1-6}$ alkoxy, hydroxy, oxo, amino, amido, alkyl urea, optionally substituted 3-7 member heterocyclyl;
$R^7$ is hydrogen or $C_{1-6}$ alkyl; or $R^7$ together with Ring A forms an 8-12 membered bicyclic heterocyclyl optionally substituted with 1-5 occurrences of $R^1$;
m is 0-5;
n is 0-5; and
p is 0-2.

In the compounds disclosed herein, a warhead is a moiety that is reactive with a nucleophile, for example, capable of forming a covalent bond with a nucleophile. Examples of warheads include, without limitation, alkyl halides, alkyl sulfonates, heteroaryl halides, epoxides, haloacetamides, maleimides, sulfonate esters, alpha-beta unsaturated ketones, alpha-beta unsaturated esters, vinyl sulfones, propargyl amides, acrylamides. In some of these instances, e.g., acrylamide and propargyl amide, the N of the warhead is the adjacent N in the formulae shown above. Structures of exemplary warheads are shown below:

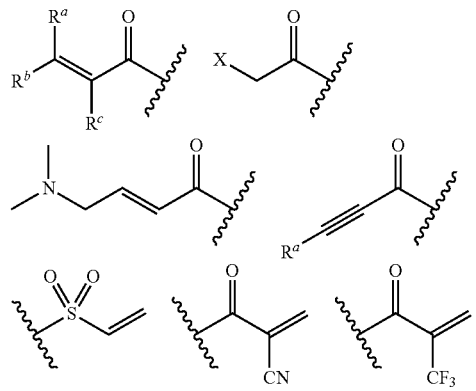

wherein X is a leaving group such as halo, or an activated hydroxyl moiety (e.g., triflate); and each of $R^a$, $R^b$, and $R^c$ is, independently, H, substituted or unsubstituted $C_{1-4}$ alkyl, substituted or unsubstituted $C_{1-4}$ cycloalkyl, or cyano.

In the formulae shown above, the warheads are typically attached to a N atom on the inhibitor. In other embodiments, the warhead can alternatively be attached to an atom other than N. Examples of exemplary warheads include, without limitation,

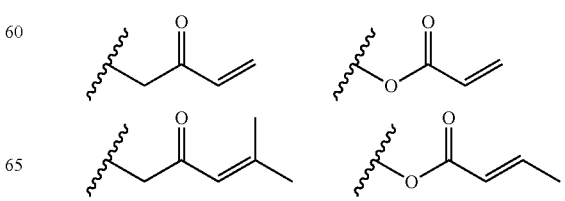

-continued

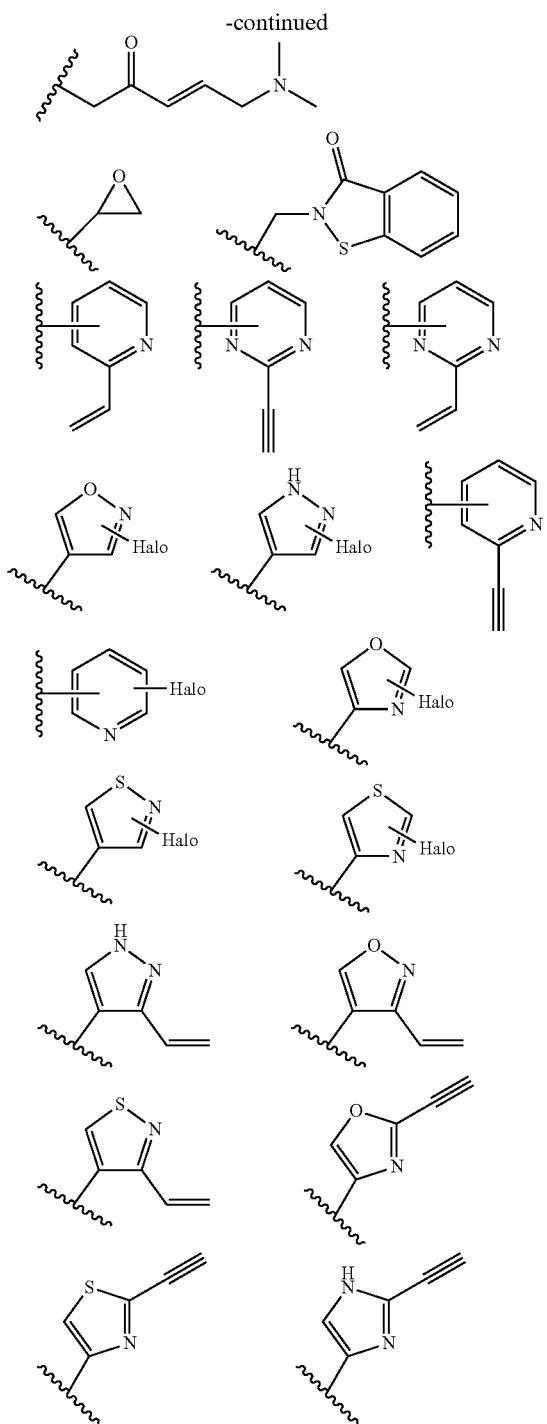

Other examples of warheads can be found, e.g., in WO 2010/028236 and WO 2011/034907.

In another aspect, the invention features a method for treating a condition mediated by FGFR-4, a condition characterized by overexpression of FGFR-4, a condition characterized by amplification of FGFR4, a condition mediated by FGF19, a condition characterized by amplified FGF-19, or a condition characterized by overexpression of FGF19, any of these methods comprising administering a therapeutically effective amount of a compound disclosed herein to a subject.

In another aspect, the invention features a method of treating any of the following conditions by administering a therapeutically effective amount of a compound disclosed herein to a subject: hepatocellular carcinoma, breast cancer, ovarian cancer, lung cancer, liver cancer, a sarcoma, or hyperlipidemia.

The invention includes all possible combinations of the embodiments described above and below.

DETAILED DESCRIPTION

The compounds disclosed herein can form a covalent bond with FGFR-4 protein; for example, the compounds can form a covalent bond with a cysteine residue of FGFR-4, for example, the cysteine at residue 552. FGFRs1-3 do not contain this cysteine. The ability to form a covalent bond between the compound and FGFR-4 is therefore an important factor in the selectivity of the compounds disclosed herein for FGFR-4.

The details of construction and the arrangement of components set forth in the following description or illustrated in the drawings are not meant to be limiting. Other embodiments and different ways to practice the invention are expressly included. Also, the phraseology and terminology used herein are for the purpose of description and should not be regarded as limiting. The use of "including," "includes," "include," "comprising," or "having," "containing", "involving", and variations thereof herein, is meant to encompass the items listed thereafter and equivalents thereof as well as additional items.

Definitions

"Aliphatic group", as used herein, refers to a straight-chain, branched-chain, or cyclic hydrocarbon group and includes saturated and unsaturated groups, such as an alkyl group, an alkenyl group, and an alkynyl group.

"Alkenyl", as used herein, refers to an aliphatic group containing at least one double bond.

"Alkoxyl" or "alkoxy", as used herein, refers to an alkyl group having an oxygen radical attached thereto. Representative alkoxyl groups include methoxy, ethoxy, propyloxy, tert-butoxy and the like.

"Alkyl", as used herein, refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. "Alkylene" refers to a double radical, that is, an aliphatic group substituted on two ends. In some embodiments, a straight chain or branched chain alkyl has 30 or fewer carbon atoms in its backbone (e.g., $C_1$-$C_{30}$ for straight chains, $C_3$-$C_{30}$ for branched chains), and in other embodiments can have 20 or fewer, or 10 or fewer. Likewise, certain cycloalkyls may have from 3-10 carbon atoms in their ring structure, and in some embodiments may have 5, 6 or 7 carbons in the ring structure. The term "alkenyl", as used herein, refers to an aliphatic group containing at least one double bond; the term "alkynyl", as used herein, refers to an aliphatic group containing at least one triple bond.

"Alkylthio", as used herein, refers to a hydrocarbyl group having a sulfur radical attached thereto. In some embodiments, the "alkylthio" moiety is represented by one of —S-alkyl, —S-alkenyl, or —S-alkynyl. Representative alkylthio groups include methylthio, ethylthio, and the like.

"Amido", as used herein, refers to —C(=O)—N($R^1$)($R^2$) or —N($R^1$)—C(=O)—$R^2$ wherein each of $R^1$ and $R^2$ is independently hydrogen, hydroxyl, $C_1$-$C_6$ alkyl, or $C_1$-$C_6$ alkoxyl, e.g., methoxyl.

"Amino", as used herein, refers to —NH$_2$, —NH(alkyl), or —N(alkyl)(alkyl).

"Amplified", as used herein, means additional copies of a gene or chromosome segment are produced in cancer cells that may confer a growth or survival advantage.

"Aralkyl", as used herein, refers to an alkyl group substituted with an aryl group (e.g., an aromatic or heteroaromatic group).

"Aryl", as used herein, refers to 5-, 6-, and 7-membered single-ring aromatic groups that may include from zero to four heteroatoms, for example, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. Each ring can contain, e.g., 5-7 members.

The term "carbocycle" as used herein, refers to an aromatic or non-aromatic ring in which each atom of the ring is carbon.

The term "cycloalkyl" as used herein, includes cyclic, bicyclic, tricyclic, or polycyclic non-aromatic hydrocarbon groups having 3 to 12 carbons. Any substitutable ring atom can be substituted (e.g., by one or more substituents). The cycloalkyl groups can contain fused or spiro rings. Fused rings are rings that share a common carbon atom. Examples of cycloalkyl moieties include, but are not limited to, cyclopropyl, cyclobutyl, cyclopentyl, cyclohexyl, methylcyclohexyl, adamantyl, and norbornyl.

"Covalent inhibitor," as used herein, means an inhibitor that can form a covalent bond with a protein.

The "enantiomeric excess" or "% enantiomeric excess" of a composition can be calculated using the equation shown below. In the example shown below a composition contains 90% of one enantiomer, e.g., the S-enantiomer, and 10% of the other enantiomer, i.e., the R-enantiomer.

$$ee=(90-10)/100=80\%.$$

Thus, a composition containing 90% of one enantiomer and 10% of the other enantiomer is said to have an enantiomeric excess of 80%. In some embodiments, the compositions described herein contain an enantiomeric excess of at least 50%, at least 75%, at least 80%, at least 85%, at least 90%, at least 95%, or at least 99% of the S-enantiomer. In other words, the compositions contain an enantiomeric excess of the S-enantiomer over the R-enantiomer. In some embodiments, the compositions described herein contain an enantiomeric excess of at least 50%, at least 75%, at least 80%, at least 85%, at least 90%, at least 95%, or at least 99% of the R-enantiomer. In other words, the compositions contain an enantiomeric excess of the R-enantiomer over the S-enantiomer.

"FGFR-4" or "FGFR-4 protein" refers to any form of the FGFR-4 protein, including wild type and all variant forms (including, without limitation, mutant forms and splice variants). The FGFR-4 protein is a product of the FGFR-4 gene, and the FGFR-4 protein therefore includes any protein encoded by any form of the FGFR-4 gene, including all aberrations, e.g., point mutations, indels, translocation fusions, and focal amplifications.

"Halo" refers to a radical of any halogen, e.g., —F, —Cl, —Br, or —I.

"Haloalkyl" and "haloalkoxy" refers to alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroarylalkyl" refers to an alkyl group substituted with a heteroaryl group.

"Heterocyclyl" or "heterocyclic group" refers to a ring structure, such as a 3- to 14-membered ring structure, whose ring(s) include one or more heteroatoms. Heterocyclyl can also include polycycles, with each group having, e.g., 3-7 ring members. The term "heterocyclyl" or "heterocyclic group" includes "heteroaryl" and "saturated or partially saturated heterocyclyl" structures. The term "saturated or partially saturated heterocyclyl" refers to a non-aromatic cyclic structure that includes at least one heteroatom. The term "heterocyclyl" can also include 8-12 membered bicyclic heterocyclyls, e.g., wherein a saturated or partially saturated heterocyclyl is fused to an aromatic or heteroaromatic ring. The term "heterocyclyl" can also include 8-12 membered bicyclic heterocyclyls, e.g., wherein a saturated or partially saturated cycloalkyl is fused to an aromatic or heteroaromatic ring. The point of attachment of the heterocyclyl to the rest of the molecule can be through the saturated or partially saturated heterocyclyl or cycloalkyl, or through the aromatic or heteroaromatic ring.

"Heteroaryl" refers to a 5-14 membered (i.e., 5-8 membered monocyclic, 8-12 membered bicyclic, or 11-14 membered tricyclic) aromatic ring system having 1-3 ring heteroatoms if monocyclic, 1-6 ring heteroatoms if bicyclic, or 1-9 ring heteroatoms if tricyclic, said ring heteroatoms independently selected from O, N, and S (e.g., 1-3, 1-6, or 1-9 ring heteroatoms of N, O, or S if monocyclic, bicyclic, or tricyclic, respectively). Any ring atom can be substituted (e.g., by one or more substituents).

Heterocyclyl groups include, for example, thiophenyl, thianthrenyl, furanyl, pyranyl, isobenzofuranyl, chromenyl, xanthenyl, phenoxathiin, pyrrolyl, imidazolyl, pyrazolyl, isothiazolyl, isoxazolyl, pyridinyl, pyrazinyl, pyrimidinyl, pyridazinyl, indolizinyl, isoindolyl, indolyl, indazolyl, purinyl, quinolizinyl, isoquinolinyl, quinolinyl, phthalazinyl, naphthyridinyl, quinoxalinyl, quinazolinyl, cinnolinyl, pteridinyl, carbazolyl, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

"Heterocyclylalkyl" refers to an alkyl group substituted with a heterocycle group.

"Hydroxy" or "hydroxyl" refers to the chemical group —OH.

"Inhibitor" refers to a compound that inhibits an enzyme such that a reduction in activity of the enzyme can be observed, e.g., in a biochemical assay. In certain embodiments, an inhibitor has an $IC_{50}$ of less than about 1 µM, less than about 500 nM, less than about 250 nM, less than about 100 nM, less than about 50 nM, or less than about 10 nM. An inhibitor of FGFR-4 refers to a compound that inhibits FGFR-4.

"Nucleophile" refers to a species that donates an electron-pair to an electrophile to form a chemical bond in a reaction. In some embodiments, a nucleophile can be an oxygen nucleophile, e.g., water or hydroxyl, a nitrogen nucleophile, e.g., amine, or a sulfur nucleophile, e.g., thiol, such as, for example, the thiol in the side chain of a cysteine residue.

"Overexpressed," as used herein, means there is production of a gene product in a sample that is substantially higher than that observed in a population of control samples (e.g. normal tissue).

"Oxo" refers to (=O).

"Selective" refers to a compound that inhibits the activity of a target protein, e.g., FGFR-4, more potently than it inhibits activity of other proteins. In this instance, the isoforms FGFR-1, FGFR-2, FGFR-3, and FGFR-4 are all considered distinct proteins. In some embodiments, a compound can inhibit the activity of the target protein, e.g., FGFR-4, at least 1.5, at least 2, at least 5, at least 10, at least 20, at least 30, at least 40, at least 50, at least 60, at least 70, at least 80, at least 90, at least 100, at least 200, at least 500, or at least 1000 or more times potently than it inhibits the activity of a non-target protein.

"Substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

"Warhead moiety" or "warhead" refers to a moiety of an inhibitor which participates, either reversibly or irreversibly, with the reaction of a donor, e.g., a protein, with a substrate. Warheads may, for example, form covalent bonds with the protein, or may create stable transition states, or be a reversible or an irreversible alkylating agent. For example, the warhead moiety can be a functional group on an inhibitor that can participate in a bond-forming reaction, wherein a new covalent bond is formed between a portion of the warhead and a donor, for example an amino acid residue of a protein. In embodiments, the warhead is an electrophile and the "donor" is a nucleophile such as the side chain of a cysteine residue. Examples of suitable warheads include, without limitation, the groups shown below:

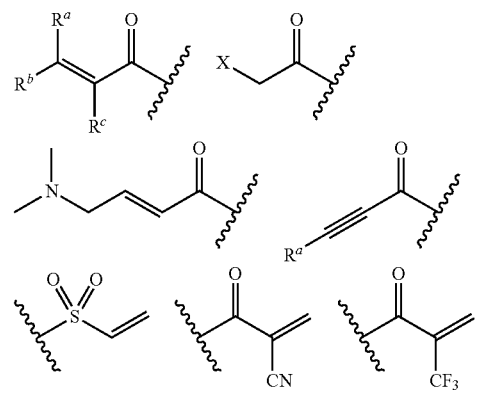

wherein X is a leaving group such as halo, or an activated hydroxyl moiety (e.g., triflate); and each of $R^a$, $R^b$, and $R^c$ is, independently, H, substituted or unsubstituted $C_{1-4}$ alkyl, substituted or unsubstituted $C_{1-4}$ cycloalkyl, or cyano.

As used herein, the term "patient" or "subject" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "modulate" or "modulating" refers to an increase or decrease, e.g., in the activity of an enzyme in response to exposure to a compound or composition described herein, e.g., the inhibition of FGFR-4, in at least a sub-population of cells in a subject such that a desired end result is achieved (e.g., a therapeutic result). In some embodiments, a compound as described herein inhibits a target described herein, e.g., FGFR-4.

Compounds

The compounds described herein may contain unnatural proportions of atomic isotopes at one or more of the atoms that constitute such compounds. For example, the compounds may be radiolabeled with radioactive isotopes, such as for example tritium ($^3$H) or carbon-14 ($^{14}$C). All isotopic variations of the compounds disclosed herein, whether radioactive or not, are intended to be encompassed within the scope of the present invention. For example, deuterated compounds or compounds containing $^{13}$C are intended to be encompassed within the scope of the invention.

Certain compounds can exist in different tautomeric forms, and all possible tautomeric forms of all of the compounds described herein are intended to be encompassed within the scope of the invention.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The compounds described herein can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

In one aspect, the invention provides a compound having structural Formula I:

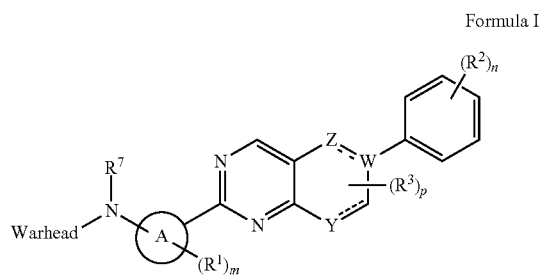

Formula I wherein:

⌇ denotes a single or double bond;

Warhead is a moiety capable of forming a covalent bond with a nucleophile;

Ring A is a 5-8 membered aryl, 5-12 membered heteroaryl, 3-7 member heterocyclyl or 3-12 membered cycloalkyl group;

W is C or N, X and Z are each independently CH or N;

Y is CH or N—R$^4$ where R$^4$ is H, C$_{1-6}$ alkyl, or 3-12 membered cycloalkyl;

each of R$^1$-R$^3$ is, independently, halo, cyano, optionally substituted C$_{1-6}$ alkyl, optionally substituted C$_{1-6}$ alkoxy, hydroxy, oxo, amino, amido, alkyl urea, optionally substituted 3-7 member heterocyclyl;

R$^7$ is hydrogen or C$_{1-6}$ alkyl; or R$^7$ together with Ring A forms an 8-12 membered bicyclic heterocyclyl optionally substituted with 1-5 occurrences of R$^1$;

m is 0-5;

n is 0-5; and p is 0-2.

In some embodiments, ⌇ denotes a single bond. In some embodiments, ⌇ denotes a double bond. In some embodiments, ⌇ is a single bond and the other ⌇ is a double bond.

In some embodiments, Ring A is aryl. In some embodiments, Ring A is phenyl substituted with 0-3 R$^1$. In some embodiments, R$^1$ is selected from the group consisting of halo, optionally substituted C$_{1-6}$ alkyl, and optionally substituted C$_{1-6}$ alkoxy.

In some embodiments, R$^7$ is hydrogen or C$_{1-6}$ alkyl. In some embodiments, R$^7$ together with Ring A forms an 8-12 membered bicyclic heterocyclyl optionally substituted with 1-5 occurrences of R$^1$. In some embodiments, R$^7$ together with Ring A forms an 8-12 membered bicyclic heterocyclyl optionally substituted with 1-3 occurrences of R$^1$.

In some embodiments, X is N. In some embodiments, X is CH.

In some embodiments, Y is N—R$^4$ wherein R$^4$ is C$_{1-6}$ alkyl or 3-12 membered cycloalkyl. In some embodiments, R$^4$ is methyl, ethyl or isopropyl. In some embodiments, R$^4$ is ethyl. In some embodiments, R$^4$ is 3-12 membered cycloalkyl. In some embodiments, R$^4$ is cyclopentyl.

In some embodiments, Y is N—R$^4$ wherein R$^4$ is C$_{1-6}$ alkyl or 3-12 membered cycloalkyl and R$^3$ is oxo. In some embodiments, R$^4$ is methyl, ethyl or isopropyl. In some embodiments, R$^4$ is ethyl. In some embodiments, R$^4$ is 3-12 membered cycloalkyl. In some embodiments, R$^4$ is cyclopentyl.

In some embodiments, q is 0.

In some embodiments, the warhead moiety is selected from the group consisting of

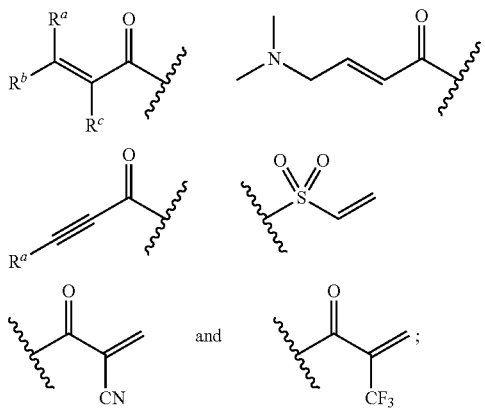

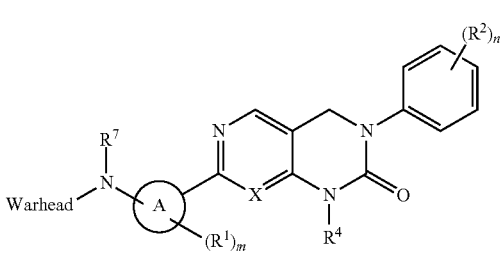

wherein X is CH or N. In some embodiments, X is CH. In some embodiments, X is N.

In one embodiment, the invention features a compound of Formula I(d) or a pharmaceutically acceptable salt thereof:

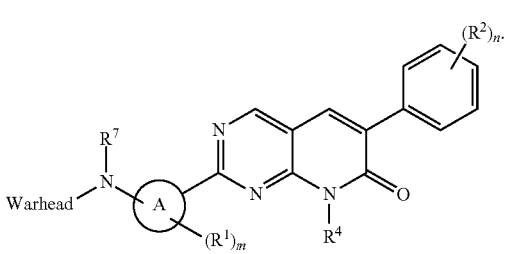

In some embodiments, the Warhead moiety is wherein each of $R^a$, $R^b$, and $R^c$ is, independently, hydrogen, optionally substituted $C_{1-4}$ alkyl, optionally substituted 3-12 membered cycloalkyl, or cyano.

In some embodiments, $R^2$ is alkoxy or halo. In some embodiments, $R^2$ is methoxy or chloro. In some embodiments, two $R^2$ are chloro and two $R^2$ are methoxy.

In one embodiment, the invention features a compound of Formula I(a) or a pharmaceutically acceptable salt thereof:

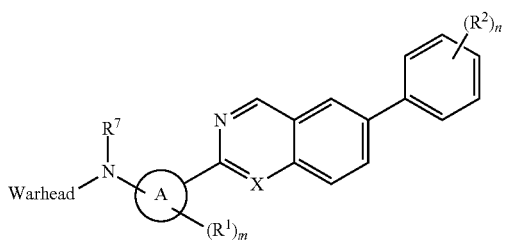

wherein X is CH or N. In some embodiments, X is CH. In some embodiments, X is N.

In one embodiment, the invention features a compound of Formula I(b) or a pharmaceutically acceptable salt thereof:

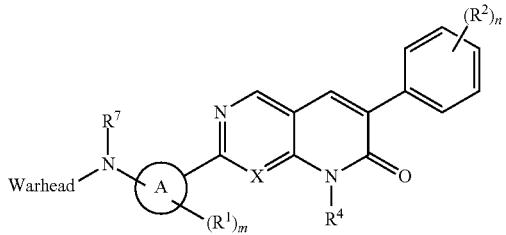

wherein X is CH or N. In some embodiments, X is CH. In some embodiments, X is N.

In one embodiment, the invention features a compound of Formula I(b) or a pharmaceutically acceptable salt thereof:

Ring A is phenyl, and $R^7$ together with Ring A forms an 8-12 membered bicyclic heterocyclyl optionally substituted with 1-5 occurrences of $R^1$; $R^4$ is $C_{1-6}$ alkyl or 3-12 membered cycloalkyl; $R^2$ is $C_{1-6}$ alkoxy or halo; and n is 4. In some embodiments, $R^7$ together with Ring A forms an 8-12 membered bicyclic heterocyclyl optionally substituted with 1-3 occurrences of $R^1$.

In some embodiments, Ring A together with $R^7$ forms an 8-10 membered heterocyclyl. In some embodiments, Ring A together with $R^7$ forms:

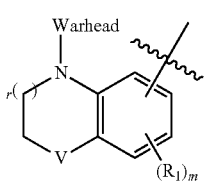

wherein V is $CH_2$ or O; r is 0 or 1; and $R^1$ and m are as defined herein.

In some embodiments, Ring A together with $R^7$ forms:

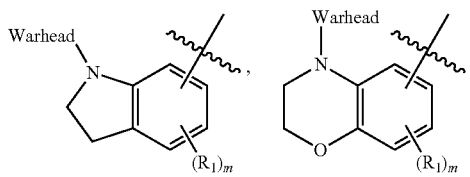

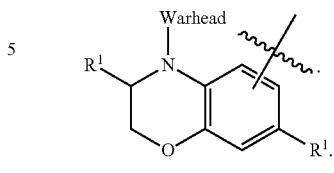

or

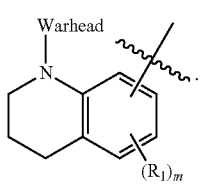

In some embodiments, Ring A together with $R^7$ forms:

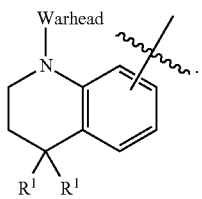

In some embodiments, Ring A together with $R^7$ forms:

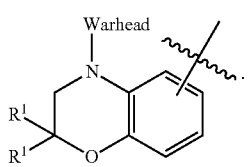

In some embodiments, Ring A together with $R^7$ forms:

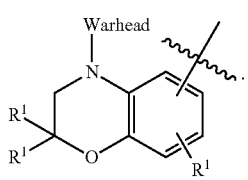

In some embodiments, Ring A together with $R^7$ forms:

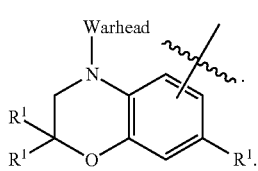

In some embodiments, Ring A together with $R^7$ forms:

[structure with Warhead, $R^1$, O, and $R^1$ substituents on a benzoxazine-type ring]

wherein V is $CH_2$ or O; r is 0 or 1; and $R^1$ and m are as defined herein.

The invention also features pharmaceutical compositions comprising a pharmaceutically acceptable carrier and any compound of Formulas I, I(a), I(b), I(c), and I(d).

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting. In certain embodiments, the compounds provided herein include their hydrates.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable salts of a compound described herein include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and $N$-(alkyl)$_4^+$ salts. This invention also envisions the quaternization of any basic nitrogen-containing groups of the compounds described herein. Water or oil-soluble or dispersible products may be obtained by such quaternization.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16)

pyrogen-free water; (17) isotonic saline; (18) Ringer's solution; (19) ethyl alcohol; (20) phosphate buffer solutions; (21) cyclodextrins such as Captisol®; targeting ligands attached to nanoparticles, such as Accurins™; and (22) other nontoxic compatible substances, such as polymer-based compositions, employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intradermally, intraperitoneally, subcutaneously, subcuticularly, or by inhalation.

Indications

FGFR-4 regulates proliferation, survival, and alpha-fetoprotein secretion during hepatocellular carcinoma (HCC) progression; inhibitors of FGFR-4 are therefore promising potential therapeutic agents for this unmet medical need (Ho et al., Journal of Hepatology, 2009, 50:118-27). HCC afflicts more than 550,000 people worldwide every year and has one of the worst 1-year survival rates of any cancer type.

Further evidence of the link between FGFR-4 and HCC is shown through the involvement of FGF19, a member of the fibroblast growth factor (FGF) family, which consists of hormones that regulate glucose, lipid, and energy homeostasis. Increased hepatocyte proliferation and liver tumor formation have been observed in FGF19 transgenic mice. FGF19 activates FGFR-4, its predominant receptor in the liver, and it is believed that activation of FGFR-4 is the mechanism whereby FGF19 can increase hepatocyte proliferation and induce hepatocellular carcinoma formation (Wu et al., J Biol Chem (2010) 285(8):5165-5170). FGF19 has been identified as a driver gene in HCC by others as well (Sawey et al., Cancer Cell (2011) 19: 347-358). It is therefore believed that the compounds disclosed herein, which are potent and selective inhibitors of FGFR-4, can be used to treat HCC and other liver cancers.

Oncogenome screening has identified an activating fibroblast growth factor receptor 4 (FGFR-4) Y367C mutation in the human breast cancer cell line MDA-MB-453. This mutation was shown to elicit constitutive phosphorylation, leading to an activation of the mitogen-activated protein kinase cascade. Accordingly, it has been suggested that FGFR-4 may be a driver of tumor growth in breast cancer (Roidl et al., Oncogene (2010) 29(10):1543-1552). It is therefore believed that the compounds disclosed herein, which are potent and selective inhibitors of FGFR-4, can be used to treat FGFR-4 modulated breast cancer.

Molecular changes (e.g., translocations) in genes upstream of FGFR-4 can lead to activation/overexpression of FGFR-4. For example, a PAX3-FKHR translocation/gene fusion can lead to FGFR-4 overexpression. Overexpression of FGFR-4 due to this mechanism has been associated with rhabdomyosarcoma (RMS) (Cao et al., Cancer Res (2010)

70(16): 6497-6508). Mutations in FGFR-4 itself (e.g., kinase domain mutations) can lead to over-activation of the protein; this mechanism has been associated with a sub-population of RMS (Taylor et al., J Clin Invest (2009) 119: 3395-3407). It is therefore believed that the compounds disclosed herein, which are potent and selective inhibitors of FGFR-4, can be used to treat FGFR-4 modulated RMS and other sarcomas.

Other diseases have been associated with changes in genes upstream of FGFR-4 or with mutations in FGFR-4 itself. For example, mutations in the kinase domain of FGFR-4 lead to over-activation, which has been associated with lung adenocarcinoma (Ding et al., Nature (2008) 455 (7216): 1069-1075). Amplification of FGFR-4 has been associated with conditions such as renal cell carcinoma (TCGA provisional data). In addition, silencing FGFR4 and inhibiting ligand-receptor binding significantly decrease ovarian tumor growth, suggesting that inhibitors of FGFR4 could be useful in treating ovarian cancer. (Zaid et al., Clin. Cancer Res. (2013) 809).

Pathogenic elevations of bile acid levels have been linked to variations in FGF19 levels (Vergnes et al., Cell Metabolism (2013) 17, 916-28). Reduction in the level of FGF19 may therefore be of benefit in promoting the synthesis of bile acid and thus in the treatment of hyperlipidemia.

Dose Levels

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above.

Combination and Targeted Therapy

Administration of the FGFR-4 inhibitors disclosed herein can be combined with other cancer treatments. For example, the inhibitors can be administered in combination with surgical treatments, radiation, or other therapeutic agents such as antibodies, other selective kinase inhibitors, or chemotherapeutics. The inhibitors may also be administered in combination with RNAi therapy or antisense therapy. The FGFR-4 inhibitors described herein may be combined with one, two, or more other therapeutic agents. Examples of other therapeutic agents include sorafenib, gemcitabine, capecitabine, and doxorubicin. In the examples outlined below, it is understood that "second therapeutic agent" also includes more than one therapeutic agent other than the FGFR-4 inhibitor. A FGFR-4 inhibitor described herein may be administered with one, two, or more other therapeutic agents.

The FGFR-4 inhibitors described herein and the second therapeutic agent do not have to be administered in the same pharmaceutical composition, and may, because of different physical and chemical characteristics, be administered by different routes. For example, the FGFR-4 inhibitor can be administered orally, while the second therapeutic agent is administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The FGFR-4 inhibitor and the second therapeutic agent may be administered concurrently (e.g., simultaneously, essentially simultaneously or within the same treatment protocol) or sequentially (i.e., one followed by the other, with an optional time interval in between), depending upon the nature of the proliferative disease, the condition of the patient, and the actual choice of second therapeutic agent to be administered.

In addition, the FGFR-4 inhibitors disclosed herein can be administered as part of an antibody-drug conjugate, where the FGFR-4 inhibitor is the "payload" portion of the conjugate.

The table below shows exemplary compounds.

| Compound Number | Structure |
|---|---|
| 1 | 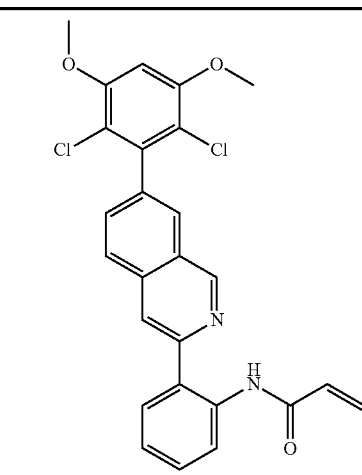 |

-continued
| Compound Number | Structure |
|---|---|
| 2 | 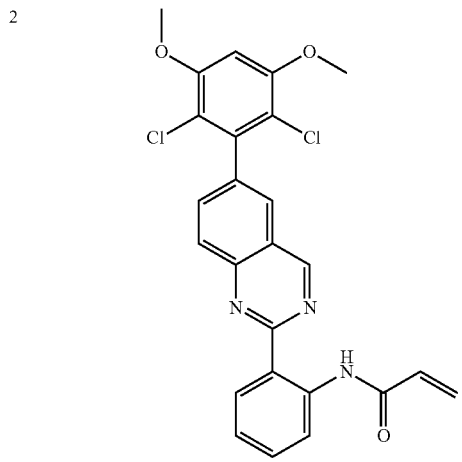 |
| 3 | 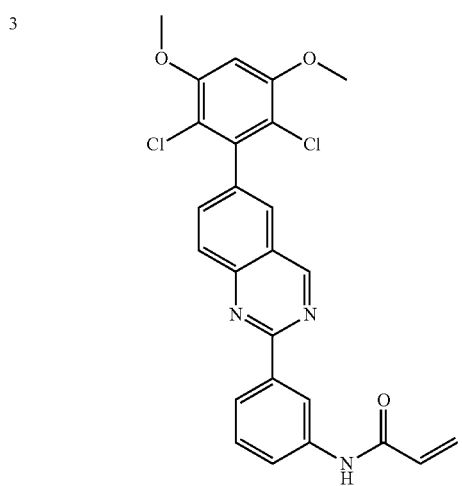 |
| 4 | 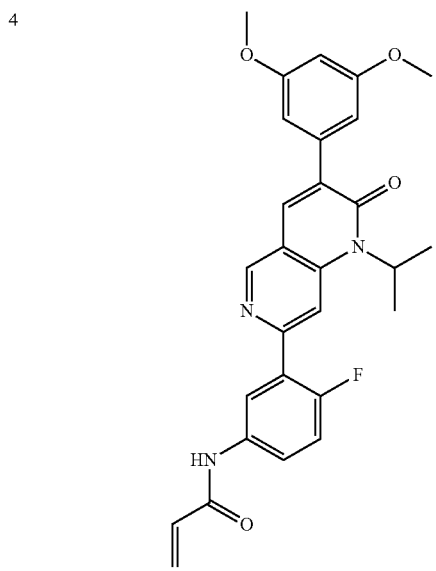 |
-continued
| Compound Number | Structure |
|---|---|
| 5 | 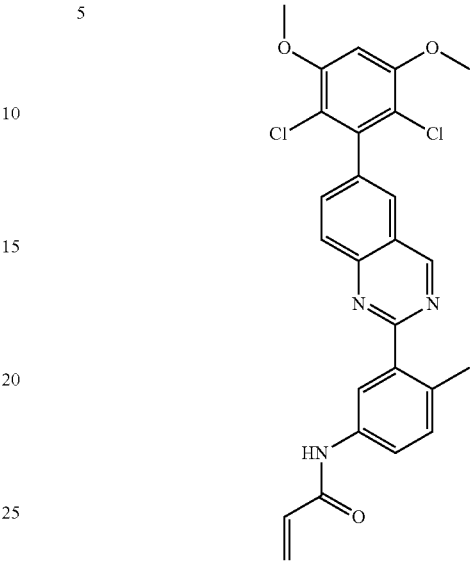 |
| 6 | 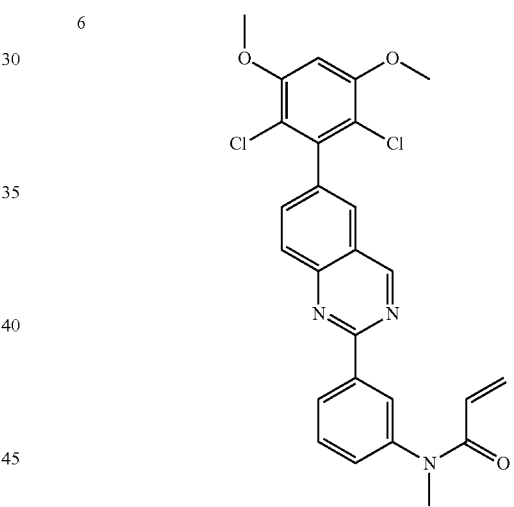 |
| 7 | 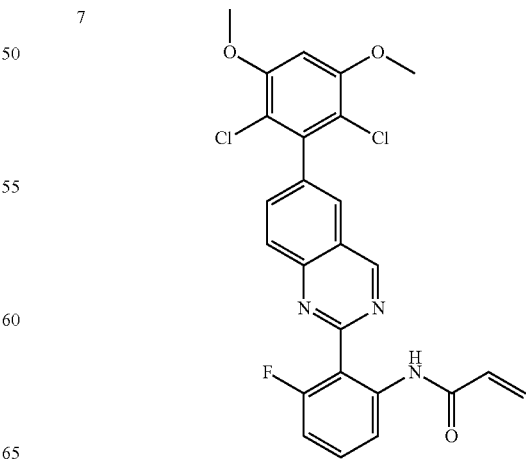 |

-continued
| Compound Number | Structure |
|---|---|
| 8 | 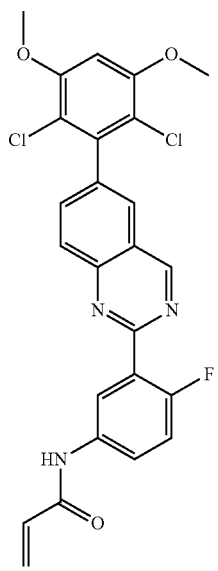 [SMILES: C=CC(=O)Nc1ccc(F)c(-c2ncc3cc(-c4c(Cl)c(OC)cc(OC)c4Cl)ccc3n2)c1] |
| 9 | 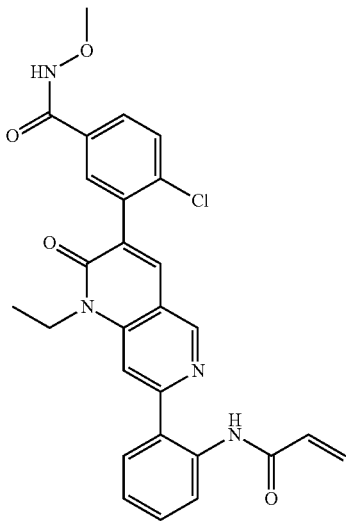 [SMILES: C=CC(=O)Nc1ccccc1-c1cc2c(cn1)cc(-c1cc(C(=O)NOC)ccc1Cl)c(=O)n2CC] |
-continued
| Compound Number | Structure |
|---|---|
| 10 | 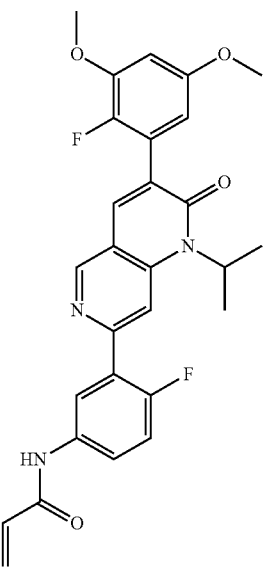 [SMILES: C=CC(=O)Nc1ccc(F)c(-c2cc3c(cn2)cc(-c2cc(OC)cc(OC)c2F)c(=O)n3C(C)C)c1] |
| 11 | 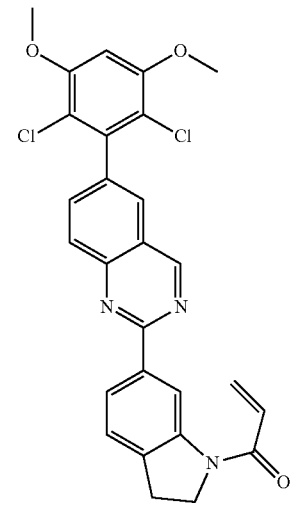 [SMILES: C=CC(=O)N1CCc2ccc(-c3ncc4cc(-c5c(Cl)c(OC)cc(OC)c5Cl)ccc4n3)cc21] |

-continued
| Compound Number | Structure |
|---|---|
| 12 | 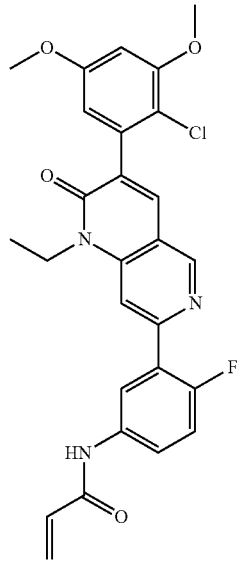 [SMILES: C=CC(=O)Nc1ccc(F)c(-c2cc3c(cn2)cc(-c2cc(OC)cc(OC)c2Cl)c(=O)n3CC)c1] |
| 13 | 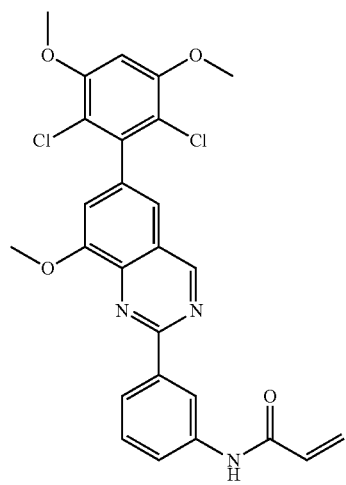 [SMILES: C=CC(=O)Nc1cccc(-c2ncc3cc(-c4c(Cl)c(OC)cc(OC)c4Cl)cc(OC)c3n2)c1] |
| 14 | 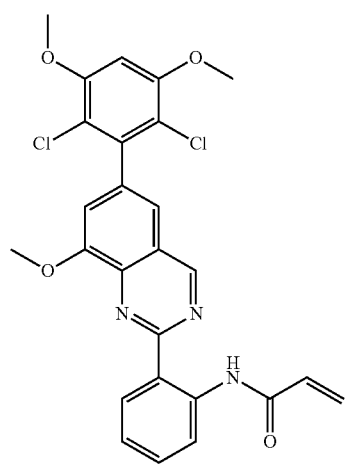 [SMILES: C=CC(=O)Nc1ccccc1-c1ncc2cc(-c3c(Cl)c(OC)cc(OC)c3Cl)cc(OC)c2n1] |
-continued
| Compound Number | Structure |
|---|---|
| 15 | 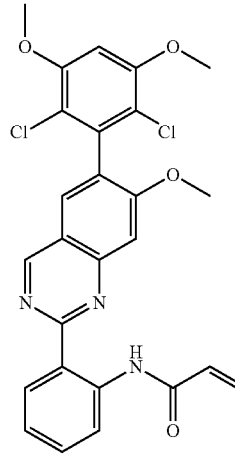 |
| 16 | 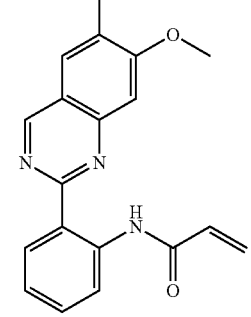 |
| 17 | 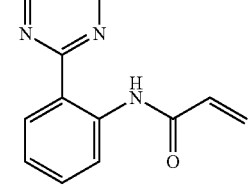 |

-continued
| Compound Number | Structure |
|---|---|
| 18 | 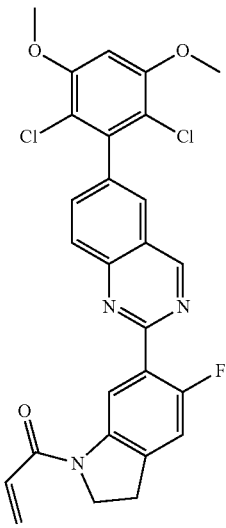 [SMILES: C=CC(=O)N1CCc2cc(F)c(-c3ncc4cc(-c5c(Cl)c(OC)cc(OC)c5Cl)ccc4n3)cc21] |
| 19 | 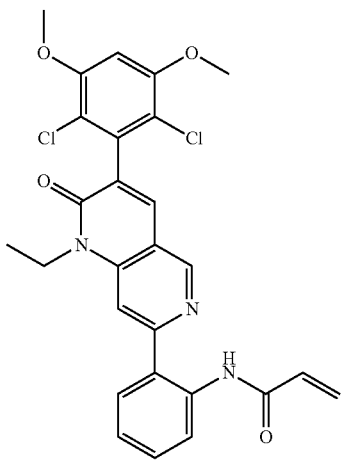 [SMILES: C=CC(=O)Nc1ccccc1-c1cc2c(cn1)cc(-c1c(Cl)c(OC)cc(OC)c1Cl)c(=O)n2CC] |
| 20 | 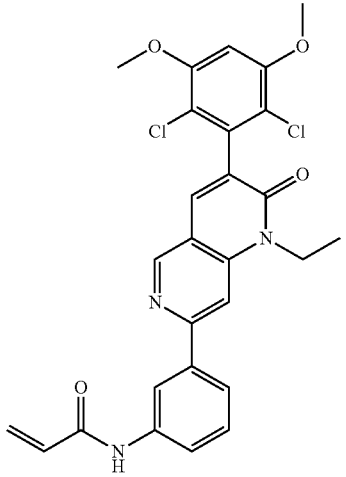 [SMILES: C=CC(=O)Nc1cccc(-c2cc3c(cn2)cc(-c2c(Cl)c(OC)cc(OC)c2Cl)c(=O)n3CC)c1] |
-continued
| Compound Number | Structure |
|---|---|
| 21 | 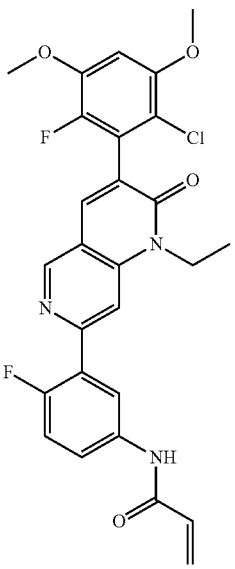 [SMILES: C=CC(=O)Nc1ccc(F)c(-c2cc3c(cn2)cc(-c2c(F)c(OC)cc(OC)c2Cl)c(=O)n3CC)c1] |
| 22 | 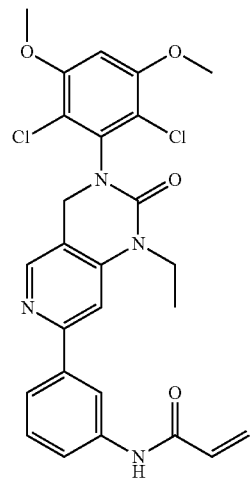 [SMILES: C=CC(=O)Nc1cccc(-c2cc3c(cn2)CN(c2c(Cl)c(OC)cc(OC)c2Cl)C(=O)N3CC)c1] |

-continued
| Compound Number | Structure |
|---|---|
| 23 | 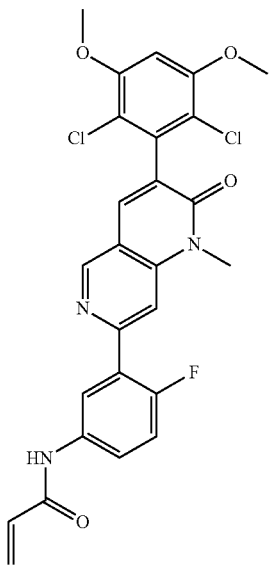 [SMILES: C=CC(=O)Nc1ccc(F)c(-c2cc3c(cn2)cc(-c2c(Cl)c(OC)cc(OC)c2Cl)c(=O)n3C)c1] |
| 24 | 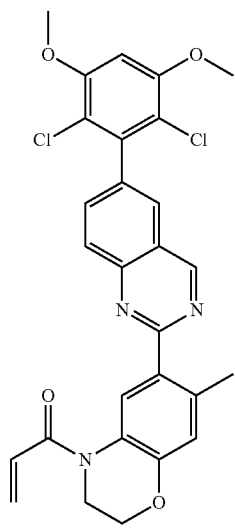 [SMILES: C=CC(=O)N1CCOc2cc(C)c(-c3ncc4cc(-c5c(Cl)c(OC)cc(OC)c5Cl)ccc4n3)cc21] |
| 25 | 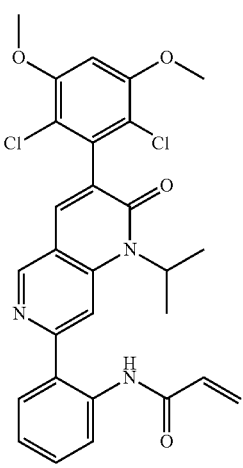 [SMILES: C=CC(=O)Nc1ccccc1-c1cc2c(cn1)cc(-c1c(Cl)c(OC)cc(OC)c1Cl)c(=O)n2C(C)C] |
-continued
| Compound Number | Structure |
|---|---|
| 26 | 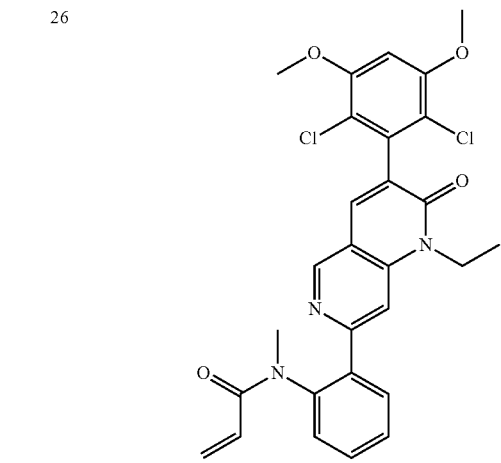 |
| 27 | 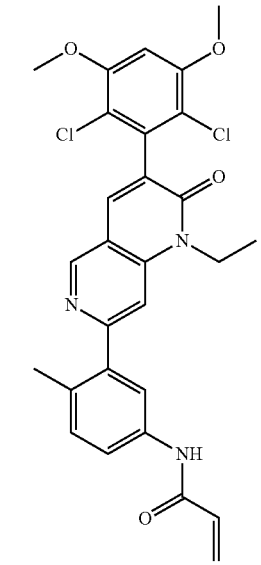 [SMILES: C=CC(=O)Nc1ccc(C)c(-c2cc3c(cn2)cc(-c2c(Cl)c(OC)cc(OC)c2Cl)c(=O)n3CC)c1] |
| 28 | 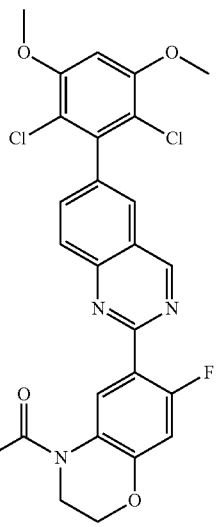 |

-continued
| Compound Number | Structure |
|---|---|
| 29 | 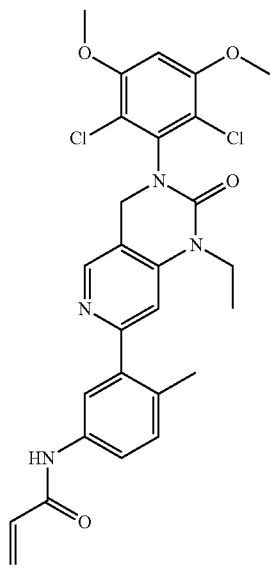 [SMILES: C=CC(=O)Nc1ccc(C)c(-c2cc3c(cn2)CN(c2c(Cl)c(OC)cc(OC)c2Cl)C(=O)N3CC)c1] |
| 30 | 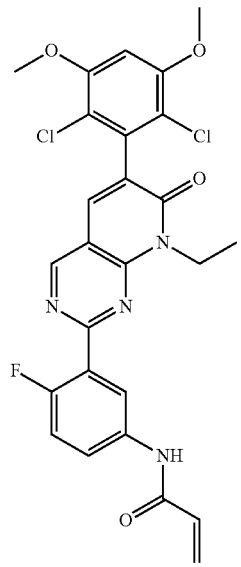 |
-continued
| Compound Number | Structure |
|---|---|
| 31 | 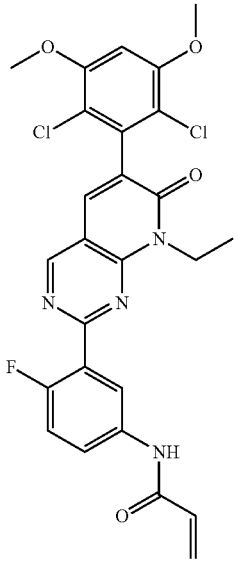 [SMILES: C=CC(=O)Nc1ccc(F)c(-c2ncc3cc(-c4c(Cl)c(OC)cc(OC)c4Cl)c(=O)n(CC)c3n2)c1] |
| 32 | 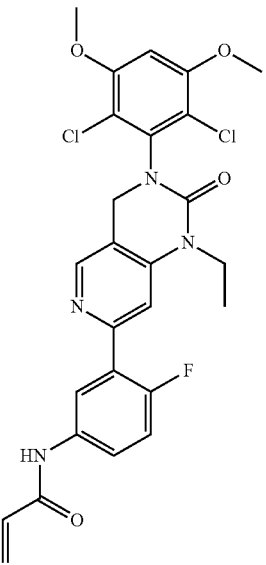 [SMILES: C=CC(=O)Nc1ccc(F)c(-c2cc3c(cn2)CN(c2c(Cl)c(OC)cc(OC)c2Cl)C(=O)N3CC)c1] |

-continued
| Compound Number | Structure |
|---|---|
| 33 | 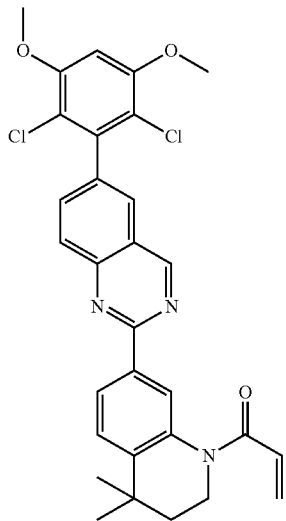 [SMILES: C=CC(=O)N1CCC(C)(C)c2ccc(-c3ncc4cc(-c5c(Cl)c(OC)cc(OC)c5Cl)ccc4n3)cc21] |
| 34 | 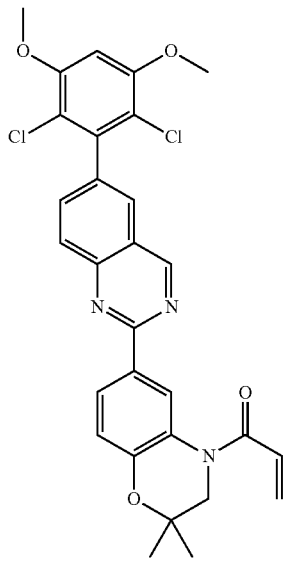 [SMILES: C=CC(=O)N1CC(C)(C)Oc2ccc(-c3ncc4cc(-c5c(Cl)c(OC)cc(OC)c5Cl)ccc4n3)cc21] |
| 35 | 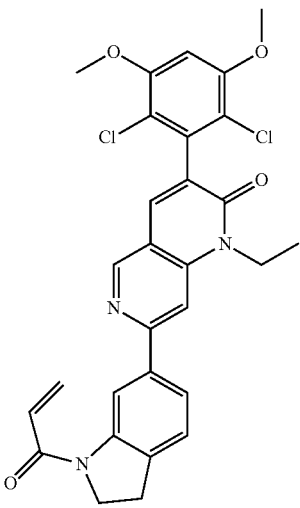 [SMILES: C=CC(=O)N1CCc2ccc(-c3cc4c(cn3)cc(-c3c(Cl)c(OC)cc(OC)c3Cl)c(=O)n4CC)cc21] |
-continued
| Compound Number | Structure |
|---|---|
| 36 | 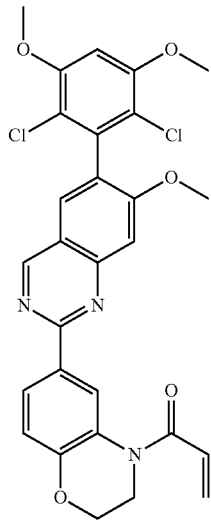 [SMILES: C=CC(=O)N1CCOc2ccc(-c3ncc4cc(-c5c(Cl)c(OC)cc(OC)c5Cl)c(OC)cc4n3)cc21] |
| 37 | 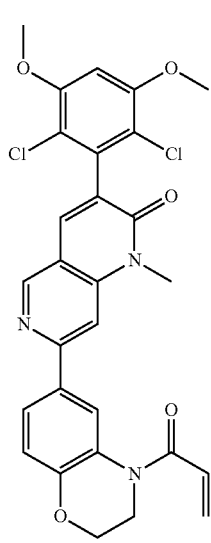 [SMILES: C=CC(=O)N1CCOc2ccc(-c3cc4c(cn3)cc(-c3c(Cl)c(OC)cc(OC)c3Cl)c(=O)n4C)cc21] |
| 38 | 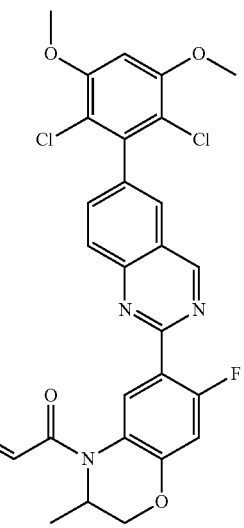 |

| Compound Number | Structure |
|---|---|
| 39 | 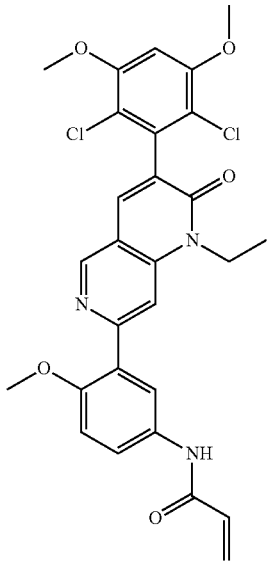 [SMILES: C=CC(=O)Nc1ccc(OC)c(-c2cc3c(cn2)cc(-c2c(Cl)c(OC)cc(OC)c2Cl)c(=O)n3CC)c1] |
| 40 | 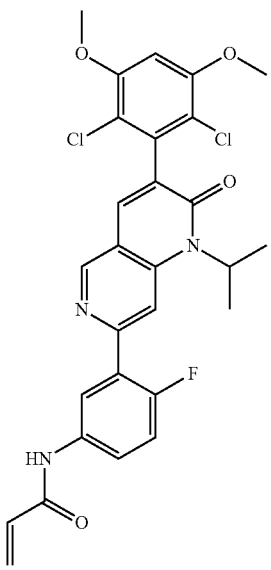 [SMILES: C=CC(=O)Nc1ccc(F)c(-c2cc3c(cn2)cc(-c2c(Cl)c(OC)cc(OC)c2Cl)c(=O)n3C(C)C)c1] |
| Compound Number | Structure |
|---|---|
| 41 | 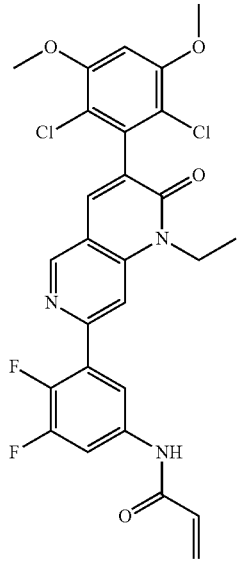 [SMILES: C=CC(=O)Nc1cc(F)c(F)c(-c2cc3c(cn2)cc(-c2c(Cl)c(OC)cc(OC)c2Cl)c(=O)n3CC)c1] |
| 42 | 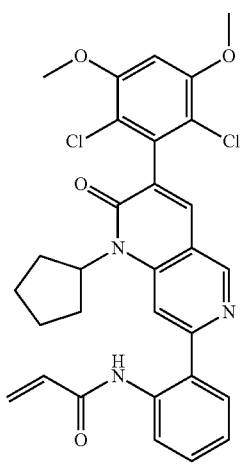 [SMILES: C=CC(=O)Nc1ccccc1-c1cc2c(cn1)cc(-c1c(Cl)c(OC)cc(OC)c1Cl)c(=O)n2C1CCCC1] |
| 43 | 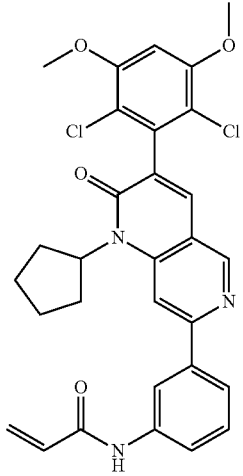 [SMILES: C=CC(=O)Nc1cccc(-c2cc3c(cn2)cc(-c2c(Cl)c(OC)cc(OC)c2Cl)c(=O)n3C2CCCC2)c1] |

-continued
| Compound Number | Structure |
|---|---|
| 44 | 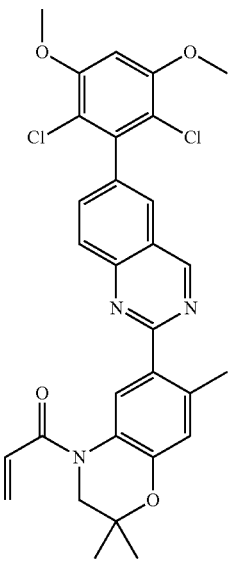 [SMILES: C=CC(=O)N1CC(C)(C)Oc2cc(C)c(-c3ncc4cc(-c5c(Cl)c(OC)cc(OC)c5Cl)ccc4n3)cc21] |
| 45 | 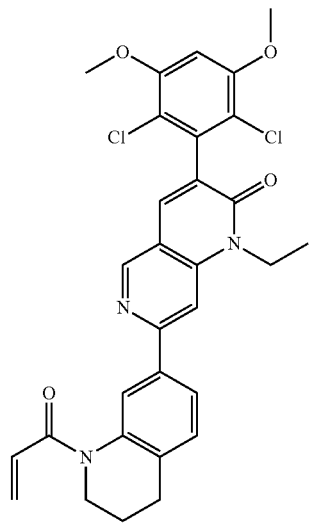 [SMILES: C=CC(=O)N1CCOc2ccc(-c3cc4c(cn3)cc(-c3c(Cl)c(OC)cc(OC)c3Cl)c(=O)n4CC)cc21] |
| 46 | 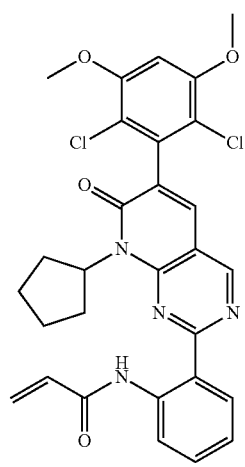 |
-continued
| Compound Number | Structure |
|---|---|
| 47 | 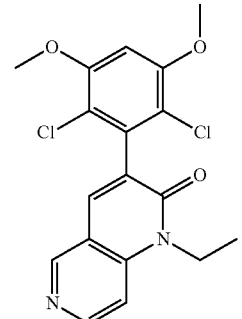 |
| 48 | 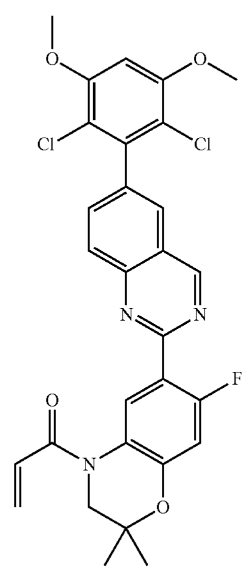 [SMILES: C=CC(=O)N1CC(C)(C)Oc2cc(F)c(-c3ncc4cc(-c5c(Cl)c(OC)cc(OC)c5Cl)ccc4n3)cc21] |

-continued
| Compound Number | Structure |
|---|---|
| 49 | 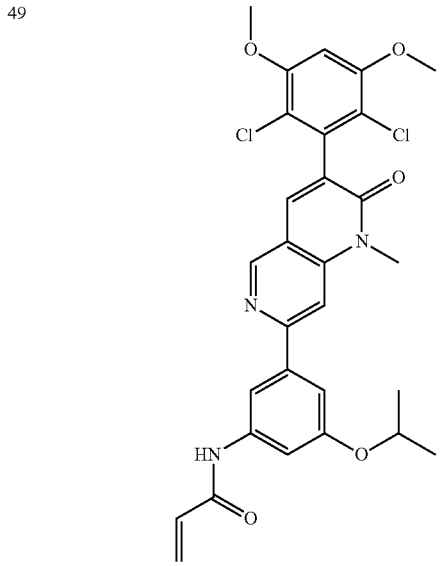 |
| 50 | 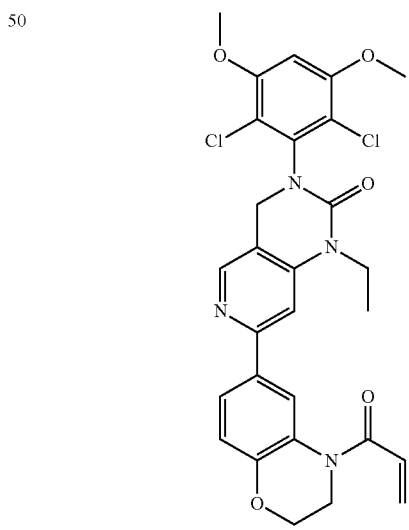 |
| 51 | 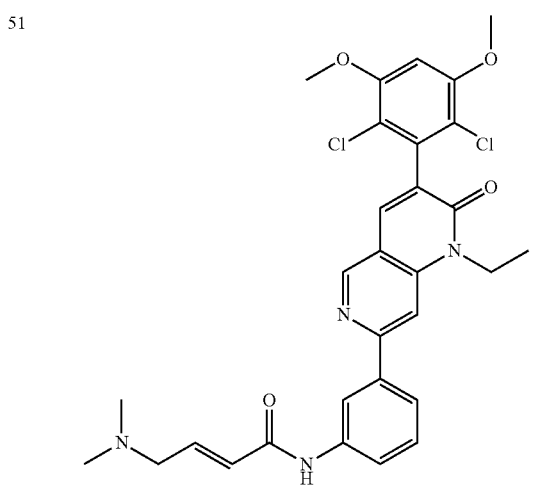 |
-continued
| Compound Number | Structure |
|---|---|
| 52 | 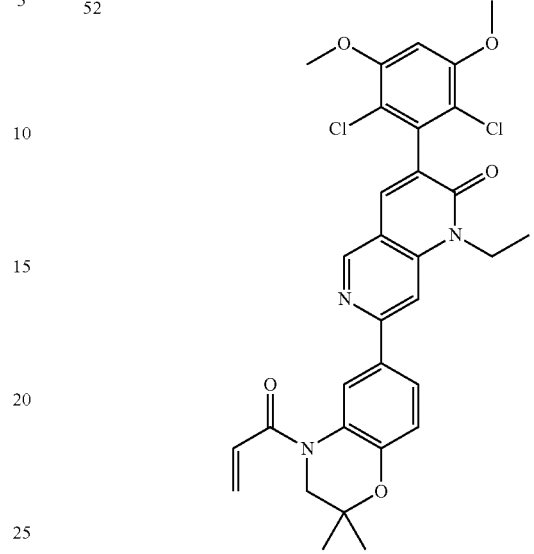 |
| 53 | 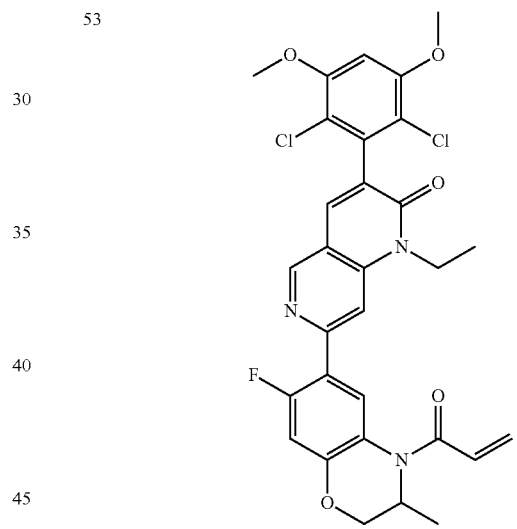 |
| 54 | 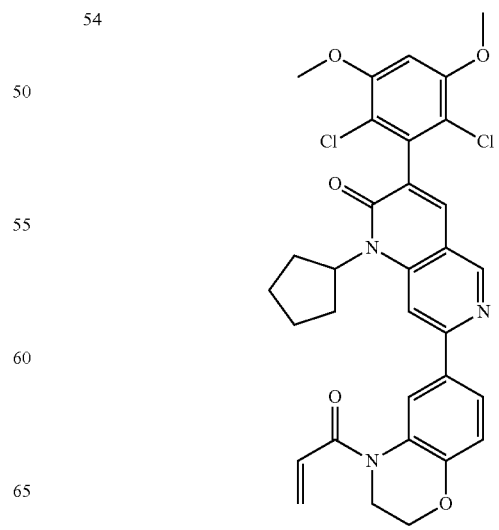 |

US 10,000,490 B2

| Compound Number | Structure |
|---|---|
| 55 | (structure shown) |
| 56 | (structure shown) |

Synthesis

Compounds of the invention, including salts and N-oxides thereof, can be prepared using known organic synthesis techniques and can be synthesized according to any of numerous possible synthetic routes, such as those in the Schemes below. The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC).

LCMS:

Liquid chromatography-mass spectrometry (LCMS) data (sample analyzed for purity and identity) can be obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase can be of a mixture of solvent 0.1% formic acid in water and 0.1% formic acid in acetonitrile. A constant gradient from 95% aqueous/5% organic to 5% aqueous/95% organic mobile phase over the course of 4 minutes can be utilized.

Proton NMR:

$^1H$ NMR spectra can be obtained with a Varian 400 MHz Unity Inova 400 MHz NMR instrument (acquisition time=3.5 seconds with a 1 second delay; 16 to 64 scans). Where characterized, all protons are generally reported in DMSO-$d^6$ solvent as parts-per million (ppm) with respect to residual DMSO (2.50 ppm).

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Example 1: Synthesis of 2-chloro-6-(2,6-dichloro-3,5-dimethoxyphenyl)quinazoline Step 1: Synthesis of (2-amino-5-bromophenyl)methanol

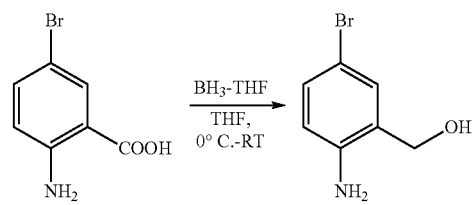 [SMILES: Nc1ccc(Br)cc1C(=O)O ; Nc1ccc(Br)cc1CO ; "BH3-THF"]

To a solution of 2-amino-5-bromobenzoic acid (10.0 g, 46.3 mmol) in THF (150 mL) was added BH$_3$-THF (1 M, 231 mL) at room temperature, and the reaction mixture was stirred overnight. An aliquot of the reaction mixture was analyzed by LCMS and indicated that the reaction had proceeded to completion. The reaction was quenched with water (150 mL) and extracted with EtOAc (3×500 mL). The organic layers were separated, combined, washed with water (200 mL) and brine (200 mL), dried over sodium sulfate, filtered, and concentrated to afford the title compound (10 g, crude), which was directly used in the next step without further purification. MS (ES+) $C_7H_8BrNO$ requires: 201, found: 202, 204 $[M+H]^+$.

Step 2: Synthesis of 2-amino-5-bromobenzaldehyde

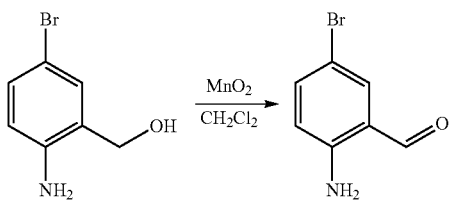

A mixture of (2-amino-5-bromophenyl)methanol (10 g, 49.5 mmol) and $MnO_2$ (25.8 g, 296.6 mmol) in $CH_2Cl_2$ (400 mL) was stirred at RT overnight. LCMS showed the reaction was completed. The solid was filtered off, and the filtrate was concentrated to give the title compound as a light yellow solid (8 g, 81%), which was directly used in next step without further purification. MS (ES+) $C_7H_6BrNO$ requires: 199, found: 200, 202 $[M+H]^+$.

Step 3: Synthesis of 6-bromoquinazolin-2-ol

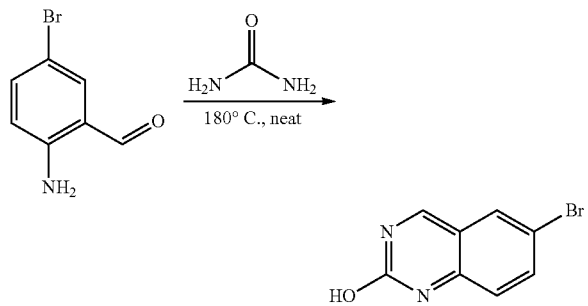

A mixture of 2-amino-5-bromobenzaldehyde (29) (6 g, 30.0 mmol) and urea (30) (27 g, 450.0 mmol) was heated to 180° C. and stirred for 5 hours. LCMS showed the reaction was completed. The reaction mixture was cooled to room temperature, and the resulting precipitate was washed with $H_2O$ (3×500 mL) and co-evaporated with toluene three times to completely remove the moisture trapped. 6-bromoquinazolin-2-ol (31)(6 g, 89%) was obtained as a yellow solid. MS (ES+) $C_8H_5BrN_2O$ requires: 224, found: 225, 227 $[M+H]^+$.

Step 4: Synthesis of 6-bromo-2-chloroquinazoline

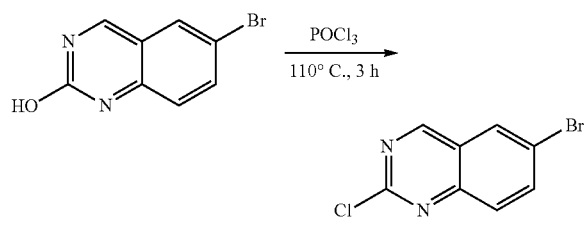

A solution of 6-bromoquinazolin-2-ol (31) (6.0 g, 26.7 mmol) in $POCl_3$ (80 mL) was refluxed at 110° C. for 5 hours. An aliquot of the reaction mixture was analyzed by LCMS and indicated that the reaction had proceeded to completion. Most of $POCl_3$ was removed under reduced pressure, and the residue was added dropwise to ice water (500 mL). The resulting precipitate was collected via filtration as a yellow solid (3.5 g, 54%). MS (ES+) $C_8H_4BrClN_2$ requires: 242, found: 243, 245 $[M+H]^+$.

Step 5: Synthesis of 2-chloro-6-(3,5-dimethoxyphenyl)quinazoline

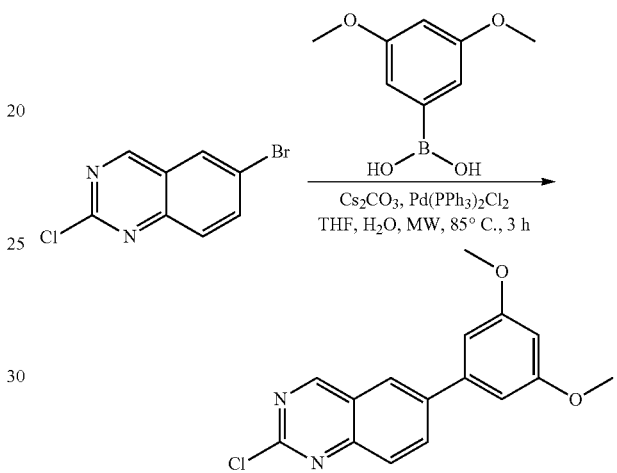

A mixture of 6-bromo-2-chloroquinazoline (32) (5.0 g, 20.5 mmol), 3,5-dimethoxyphenylboronic acid (33) (3.7 g, 20.5 mmol), $Cs_2CO_3$ (20.0 g, 61.5 mmol) and $Pd(PPh_3)_2Cl_2$ (1.4 g, 2.1 mmol) in THF (50 mL), dioxane (50 mL) and water (10 mL) was degassed with $N_2$ three times, and stirred at 80° C. for 3 hours. An aliquot of the reaction mixture was analyzed by both TLC and LCMS, which indicated that the reaction had proceeded to completion. The mixture was cooled to room temperature, and extracted with EtOAc (3×200 mL). The combined organic layers were washed with water and brine, dried over sodium sulfate, filtered and concentrated. The residue was purified by silica gel chromatography (petroleum ether/EtOAc=8:1) to obtain 2-chloro-6-(3,5-dimethoxyphenyl)quinazoline (34) as a light yellow solid (2.4 g, 38%). MS (ES+) $C_{16}H_{13}ClN_2O_2$ requires: 300, found: 301, 303 $[M+H]^+$.

Step 6: Synthesis of 2-chloro-6-(2,6-dichloro-3,5-dimethoxyphenyl)quinazoline

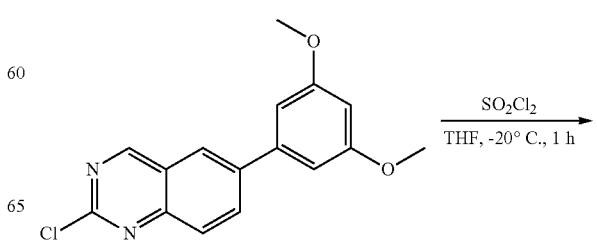

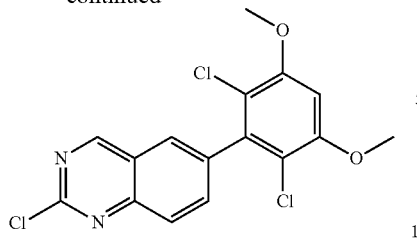

To a solution of 2-chloro-6-(3,5-dimethoxyphenyl)quinazoline (34) (2.7 g, 8.9 mmol) in dry THF (80 mL) was added dropwise SO₂Cl₂ (3.0 g, 22.3 mmol) at −20° C., and the reaction mixture was stirred for an additional hour. An aliquot of the reaction mixture was analyzed by both TLC and LCMS, which indicated that the reaction had proceeded to completion. The reaction mixture was quenched with water (1 mL), and the solvents were removed under reduced pressure. The precipitate was washed with CH₃CN and dried to obtain 2-chloro-6-(2,6-dichloro-3,5-dimethoxyphenyl)quinazoline (35) (2.6 g, 79%) as a white solid.

Synthetic Example 2: Synthesis of 7-chloro-3-(2,6-dichloro-3,5-dimethoxyphenyl)-1-methyl-1,6-naphthyridin-2(1H)-one Step 1: Synthesis of ethyl 6-chloro-4-(methylamino)nicotinate

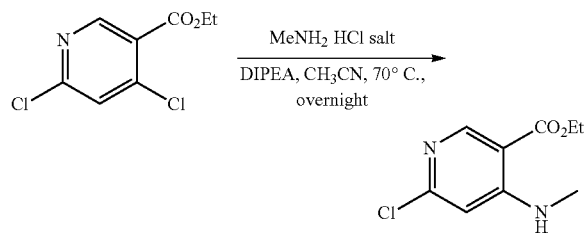

To a solution of ethyl 4,6-dichloronicotinate (5.0 g, 22.7 mmol) in acetonitrile (50 mL) was added methylamine hydrochloride salt (1.84 g, 27.2 mmol) and diisopropylethylamine (14.6 g, 113.6 mmol), and the reaction mixture was heated at 70° C. overnight. LCMS showed the reaction was completed. The reaction was cooled to RT, quenched with water (50 mL) and extracted with ethyl acetate (3×100 mL). The organic layers were separated, combined, washed with water (50 mL) and brine (100 mL), dried over sodium sulfate, filtered, and concentrated to afford the title compound (4.7 g, crude), which was directly used in the next step without further purification. MS (ES+) C₉H₁₁ClN₂O₂ requires: 214, 216, found: 215, 217 [M+H]⁺.

Step 2: Synthesis of (6-chloro-4-(methylamino)pyridin-3-yl)methanol

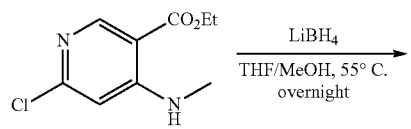

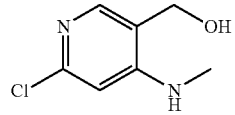

To a solution of ethyl 6-chloro-4-(methylamino)nicotinate (4.7 g, 21.9 mmol) in THF (30 mL) and methanol (30 mL) was added lithium borohydride (2.4 g, 109.8 mmol), and the reaction mixture was heated at 55° C. overnight. LCMS showed the reaction was completed. The reaction was cooled to RT, quenched with water (1 mL) and filtered. The filtrate was concentrated to afford the title compound (4.2 g, crude) as a white solid, which was directly used in the next step without further purification. MS (ES+) C₇H₉ClN₂O requires: 172, 174, found: 173, 175 [M+H]⁺.

Step 3: Synthesis of 6-chloro-4-(methylamino)nicotinaldehyde

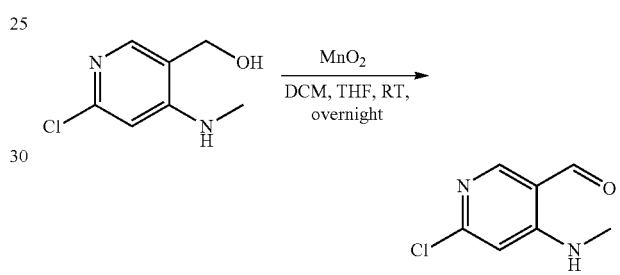

A mixture of (6-chloro-4-(methylamino)pyridin-3-yl)methanol (4.2 g, 24.7 mmol) and manganese(IV) oxide (active, 25.8 g, 296.6 mmol) in dichloromethane (50 mL) and THF (50 mL) was stirred at RT overnight. LCMS showed the reaction was completed. The solid was filtered off, and the filtrate was concentrated to afford the title compound (3.7 g, crude) as a light yellow solid, which was directly used in the next step without further purification. MS (ES+) C₇H₇ClN₂O requires: 170, 172, found: 171, 173 [M+H]⁺.

Step 4: Synthesis of 7-chloro-3-(3,5-dimethoxyphenyl)-1-methyl-1,6-naphthyridin-2(1H)-one

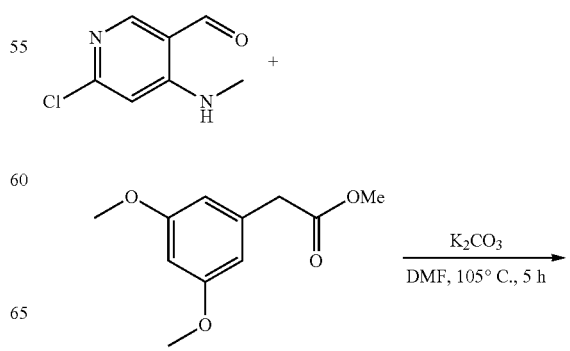

-continued

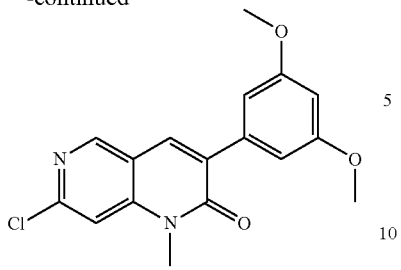

A mixture of 6-chloro-4-(methylamino)nicotinaldehyde (3.7 g, 21.7 mmol), methyl 2-(3,5-dimethoxyphenyl)acetate (4.5 g, 21.7 mmol) and potassium carbonate (9.0 g, 65.1 mmol) in N,N-dimethylformamide (30 mL) was heated at 105° C. for 5 h. LCMS showed the reaction was completed. The reaction was cooled to RT, quenched with water (200 mL), and filtered. The filtration cake was washed by petroleum ether (50 mL) and ethyl acetate (50 mL) to afford the title compound (5.8 g, 77%) as a yellow solid. MS (ES+) $C_{18}H_{19}ClN_2O_3$ requires: 346, 348, found: 347, 349 $[M+H]^+$.

Step 5: Synthesis of 7-chloro-3-(2,6-dichloro-3,5-dimethoxyphenyl)-1-methyl-1,6-naphthyridin-2(1H)-one

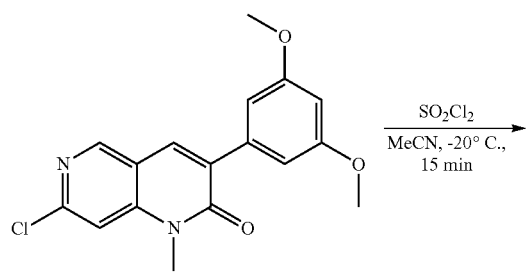

To a solution of 7-chloro-3-(3,5-dimethoxyphenyl)-1-methyl-1,6-naphthyridin-2(1H)-one (5.6 g, 16.9 mmol) in actonitrile (30 mL) was dropwise added sulfuryl chloride (3.36 mL, 42.2 mmol) at −20° C., and the mixture was stirred for another 15 mins. LCMS showed the reaction was completed. The reaction was quenched with water (1 mL), and the solvents were removed under reduced pressure. The precipitate was washed with acetonitrile and dried to afford the title compound (5.01 g, 75%) as a white solid.

Synthetic Example 2a: Synthesis of 7-chloro-1-isopropyl-3-(2-fluoro-3,5-dimethoxyphenyl)-1,6-naphthyridin-2(1H)-one

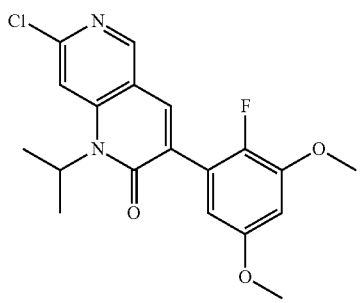 [SMILES: COc1cc(OC)c(F)c(-c2cc3cnc(Cl)cc3n(C(C)C)c2=O)c1]

To a stirred −15° C. mixture of 7-chloro-3-(3,5-dimethoxyphenyl)-1-isopropyl-1,6-naphthyridin-2(1H)-one (205.5 mg, 0.573 mmol) in acetonitrile (11.5 mL) was added Selectfluor (203 mg, 0.573 mmol). The mixture was stirred at −15° C. and slowly allowed to warm up to room temperature over 1 hour. The reaction was stirred for a total of 3 hours and 45 minutes before workup. The reaction was diluted with dichloromethane (50 mL) and washed with saturated aqueous NaHCO3 (30 mL). The aqueous layer was extracted with fresh dichloromethane (2×30 mL). The combined organic layers were dried over sodium sulfate, filtered, concentrated down and purified by silica gel chromatography to yield 7-chloro-1-isopropyl-3-(2-fluoro-3,5-dimethoxyphenyl)-1,6-naphthyridin-2(1H)-one (124.9 mg, 57.3% yield). MS: M+1=377.

Synthetic Example 2b: Synthesis of 7-chloro-3-(2-chloro-6-fluoro-3,5-dimethoxyphenyl)-1-ethyl-1,6-naphthyridin-2(1H)-one Step 1: Synthesis of 7-chloro-1-ethyl-3-(2-fluoro-3,5-dimethoxyphenyl)-1,6-naphthyridin-2(1H)-one

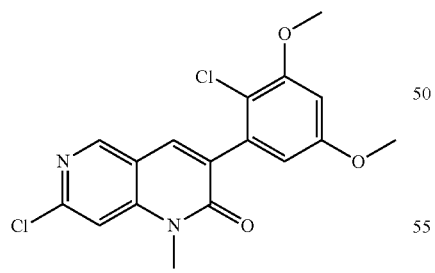

7-Chloro-1-ethyl-3-(2-fluoro-3,5-dimethoxyphenyl)-1,6-naphthyridin-2(1H)-one was prepared in a similar manner as 7-chloro-1-isopropyl-3-(2-fluoro-3,5-dimethoxyphenyl)-1,6-naphthyridin-2(1H)-one from 7-chloro-3-(3,5-dimethoxyphenyl)-1-ethyl-1,6-naphthyridin-2(1H)-one in Synthetic Example 2a. MS: M+1=363.

Step 2: Synthesis of 7-chloro-3-(2-chloro-6-fluoro-3,5-dimethoxyphenyl)-1-ethyl-1,6-naphthyridin-2(1H)-one

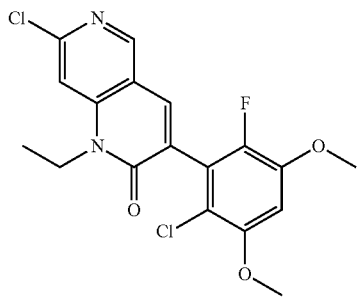 [SMILES: CCn1c(=O)c(-c2c(F)c(OC)cc(OC)c2Cl)cc2cnc(Cl)cc21]

To a 0° C. stirred suspension of 7-chloro-1-ethyl-3-(2-fluoro-3,5-dimethoxyphenyl)-1,6-naphthyridin-2(1H)-one (164.6 mg, 0.422 mmol) in acetonitrile (7 mL) was added sulfuryl chloride (57 mg, 0.422 mmol). The mixture was stirred at 0° C. At about 5 minutes, the reaction was quenched by addition of water (~30 mL). After 10 minutes of stirring, the yellow suspension was extracted with dichloromethane (120 mL+60 mL). The combined organic layers were dried over sodium sulfate, filtered, concentrated down, and dried. The crude yellow thick oil was purified by silica gel chromtaography to yield 7-chloro-3-(2-chloro-6-fluoro-3,5-dimethoxyphenyl)-1-ethyl-1,6-naphthyridin-2(1H)-one (88 mg, 50% yield) as a yellow solid. MS: M+1=397.

Synthetic Example 3: Synthesis of 7-chloro-3-(2,6-dichloro-3,5-dimethoxyphenyl)-1-ethyl-3,4-dihydropyrido[4,3-d]pyrimidin-2(1H)-one

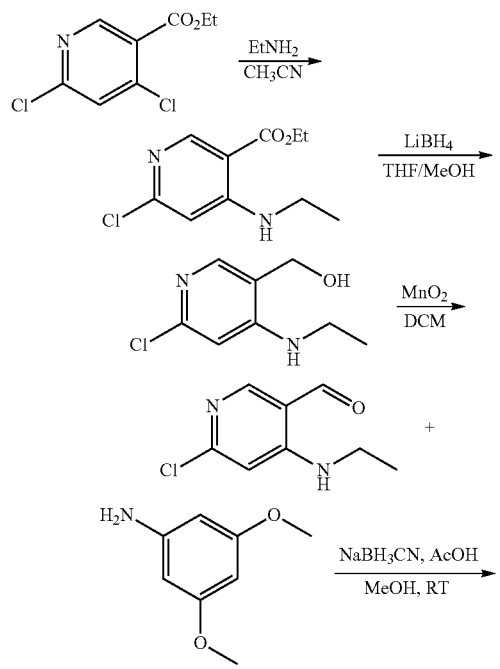

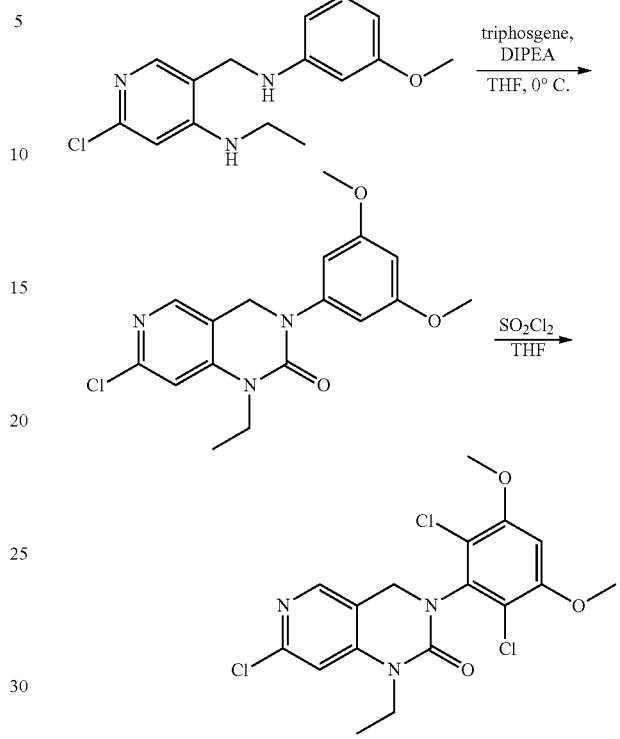

Step 1: Synthesis of ethyl 6-chloro-4-(ethylamino)nicotinate

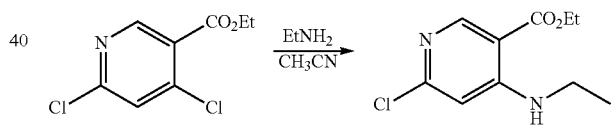

To a solution of ethyl 4,6-dichloronicotinate (6.0 g, 27.5 mmol) in acetonitrile (120 mL) was added ethylamine hydrochloride (1.45 g, 33.0 mmol) and DIPEA (17.7 g, 137.5 mmol) at RT. The resultant reaction mixture was heated at 70° C. for 12 h. After that, the reaction mixture was quenched with water (50 mL). The aqueous layer was extracted with EtOAc (3×100 mL). The organic layers were separated, combined, dried over sodium sulfate, filtered, and concentrated to afford 6-chloro-4-(ethylamino)nicotinate (6.0 g, crude), which was directly used in next step without further purification. MS (ES+) $C_{10}H_{13}ClN_2O_2$ requires: 228, 230, found: 229, 231 [M+H]+.

Step 2: Synthesis of (6-chloro-4-(ethylamino)pyridin-3-yl)methanol

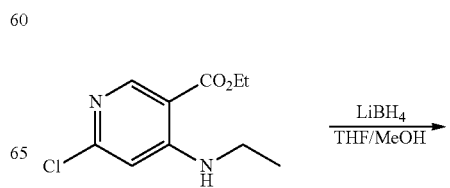

-continued

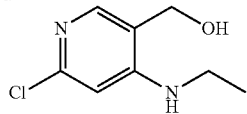

To a solution of ethyl 6-chloro-4-(ethylamino)nicotinate (3.0 g, 13.2 mmol) in THF (30 mL) and MeOH (30 mL) was added lithium borohydride (1.4 g, 65.8 mmol) at RT. The resultant reaction mixture was heated at 55° C. for 12 h. After that, the reaction mixture was quenched with water (1 mL), and the precipitate was filtered off. The filtrate was concentrated to give title compound 6-chloro-4-(ethylamino)nicotinaldehyde (2.1 g, crude), which was directly used in next step without further purification. MS (ES+) $C_8H_{11}ClN_2O$ requires: 186, 188, found: 187, 189 $[M+H]^+$.

Step 3: Synthesis of 6-chloro-4-(ethylamino)nicotinaldehyde (Notebook: SP-0010571-035)

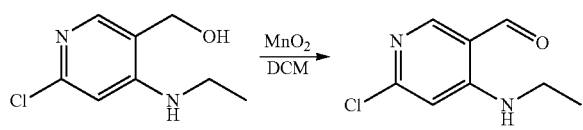

A mixture of (6-chloro-4-(ethylamino)pyridin-3-yl)methanol (4.4 g, 23.7 mmol) and manganese(IV) oxide (20.5 g, 236.6 mmol) in DCM (250 mL) and THF (50 mL) was stirred at RT for 12 h. LCMS showed the reaction was completed. The solid was filtered off, and the filtrate was concentrated to give 6-chloro-4-(ethylamino)nicotinaldehyde (4.0 g) as a light yellow solid, which was directly used in next step without the further purification. MS (ES+) $C_8H_9ClN_2O$ requires: 184, 186, found: 187, 189 $[M+H]^+$.

Step 4: Synthesis of ethyl 2-chloro-5-((3,5-dimethoxyphenylamino)methyl)-N-ethylpyridin-4-amine

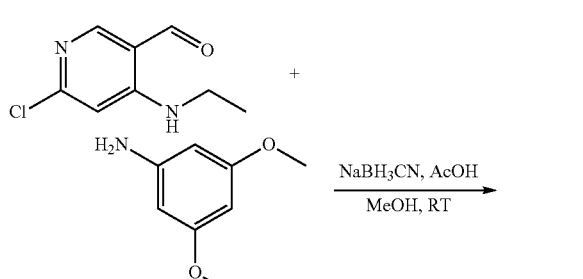

A mixture of 6-chloro-4-(ethylamino)nicotinaldehyde (700 mg, 3.8 mmol), 3,5-dimethoxyaniline (872 mg, 5.7 mmol) in MeOH (10 mL) was stirred at 20° C. for 4 h. After that, sodium cyanoborohydride (718 mg, 11.4 mmol) and acetic acid (5 mL) was added to the mixture. The resultant mixture was stirred at RT for 16 h. The mixture was diluted with EtOAc (100 mL), washed with water (50 mL) and brine, dried over $Na_2SO_4$, filtered and concentrated and purified by silica gel column, eluting with PE:EA (5:1) to get title compound ethyl 2-chloro-5-((3,5-dimethoxyphenylamino)methyl)-N-ethylpyridin-4-amine (1.1 g, 85%) as a white solid. MS (ES+) C16H20ClN3O2 requires: 321, found: 322 $[M+H]^+$.

Step 5: Synthesis of 7-chloro-3-(3,5-dimethoxyphenyl)-1-ethyl-3,4-dihydropyrido[4,3-d]pyrimidin-2(1H)-one

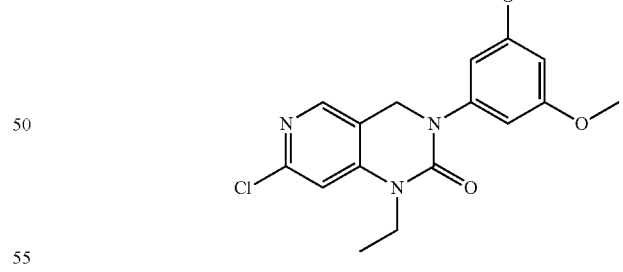

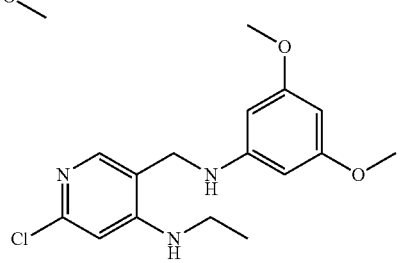

To a solution of triphosgene (345 mg, 1.2 mmol) in anhydrous THF (30 mL) at 0° C. was added 2-chloro-5-((3,5-dimethoxyphenylamino)methyl)-N-ethylpyridin-4-amine (1.1 g, 3.4 mmol) and DIPEA (877 mg, 6.8 mmol). After that, the solution was stirred at RT for 16 h. Then the solution was concentrated and purified by silica gel column, eluting with DCM:MeOH from 50:1 to 25:1 to give title compound 7-chloro-3-(3,5-dimethoxyphenyl)-1-ethyl-3,4-dihydropyrido[4,3-d]pyrimidin-2(1H)-one (250 mg, 30%) as a white solid. MS (ES+) C17H18ClN3O3 requires: 347, found: 348 [M+H]+.

Step 6: Synthesis of 7-chloro-3-(2,6-dichloro-3,5-dimethoxyphenyl)-1-ethyl-3,4-dihydropyrido[4,3-d]pyrimidin-2(1H)-one

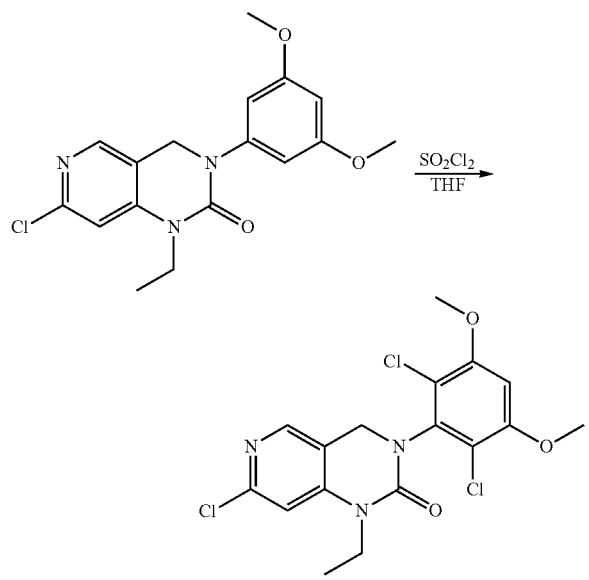

To a solution of 7-chloro-3-(3,5-dimethoxyphenyl)-1-ethyl-3,4-dihydropyrido[4,3-d]pyrimidin-2(1H)-one (250 mg, 0.72 mmol) in THF (10 mL) at −70° C. was dropwise added a solution of sulfuryl dichloride (243 mg, 1.8 mmol) in THF (2 mL). After addition, the mixture was stirred at −20° C. for another 0.5 h. LCMS showed the reaction was completed. The reaction was quenched with water (0.1 mL), and the solvents were removed under reduced pressure. The precipitate was washed with MeOH, and dried to give 7-chloro-3-(2,6-dichloro-3,5-dimethoxyphenyl)-1-ethyl-3,4-dihydropyrido[4,3-d]pyrimidin-2(1H)-one.

Synthetic Example 4: Synthesis of 6-(2,6-dichloro-3,5-dimethoxyphenyl)-8-methyl-2-(methylsulfonyl)pyrido[2,3-d]pyrimidin-7(8H)-one Step 1: Synthesis of ethyl 4-(methylamino)-2-(methylthio)pyrimidine-5-carboxylate

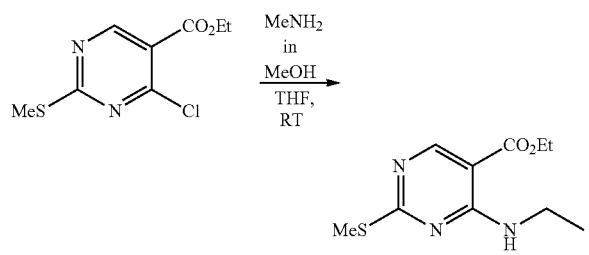

A mixture of ethyl 4-chloro-2-(methylthio)pyrimidine-5-carboxylate (5.0 g, 21.5 mmol) and 29% methylamine (5.75 g, 53.72 mmol, methanol (MeOH) solution) in tetrahydrofuran (THF) (100 mL) was stirred at room temperature for 2 hours. The reaction mixture was then concentrated, followed by the addition of sodium bicarbonate (NaHCO$_3$) (aq., 20 mL), and the resulting solution was extracted with ethyl acetate (EtOAc) (3×50 mL). The combined organic layers were washed with water and brine, dried over sodium sulfate, filtered, and concentrated to afford ethyl 4-(methylamino)-2-(methylthio)pyrimidine-5-carboxylate (4.68 g, 96%) as a yellowish solid. MS (ES+) $C_9H_{13}N_3O_2S$ requires: 227, found: 228 [M+H]$^+$.

Step 2: Synthesis of (4-(methylamino)-2-(methylthio)pyrimidin-5-yl)methanol

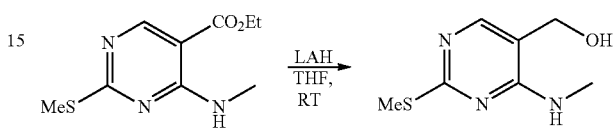

To a suspension of lithium aluminum hydride (LiAlH$_4$) (1.140 g, 30 mmol) in THF (100 mL) was added ethyl 4-(methylamino)-2-(methylthio)pyrimidine-5-carboxylate (4.536 g, 20 mmol), and the reaction mixture was stirred at room temperature for 2 hours. The solution was carefully quenched with H$_2$O (2 mL), sodium hydroxide (NaOH) (aq., 15%, 2 mL) and additional H$_2$O (7 mL), and then stirred for 1 hour. The mixture was extracted with EtOAc (2×100 mL), and the combined organic layers were washed with water and brine, dried over sodium sulfate, and concentrated to give (4-(methylamino)-2-(methylthio)pyrimidin-5-yl)methanol (3.2 g, 85%) as a yellowish solid. MS (ES+) $C_7H_{11}N_3OS$ requires: 185, found: 186 [M+H]$^+$.

Step 3: Synthesis of 4-(methylamino)-2-(methylthio)pyrimidine-5-carbaldehyde

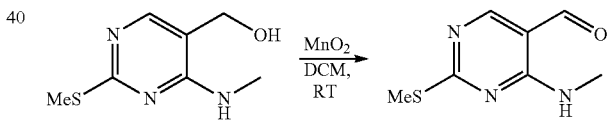

A suspension of (4-(methylamino)-2-(methylthio)pyrimidin-5-yl)methanol (3.1 g, 16.73 mmol) and manganese dioxide (7.27 g, 83.67 mmol) in DCM (40 mL) was stirred at room temperature for 12 hours. The resulting precipitate was filtered off, and the filtrate was concentrated to give 4-(methylamino)-2-(methylthio)pyrimidine-5-carbaldehyde (2.8 g, 91%) as a yellowish solid. MS (ES+) $C_7H_9N_3OS$ requires: 183, found: 184 [M+H]$^+$.

Step 4: Synthesis of methyl 2-(3,5-dimethoxyphenyl)acetate

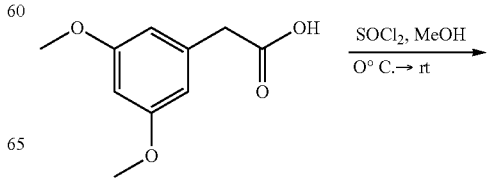

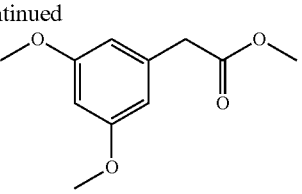

5

To a solution of 2-(3,5-dimethoxyphenyl)acetic acid (5) (600 mg, 3.06 mmol) in MeOH (30 mL) was added dropwise thionyl chloride (3 mL) at 0° C., and the reaction mixture was stirred at room temperature overnight. The reaction was monitored by liquid chromatography-mass spectrometry (LCMS). The mixture was diluted with saturated sodium bicarbonate (aq., 20 mL) and extracted by EtOAc (3×20 mL). The combined organic layers were washed with water and brine, dried over sodium sulfate, filtered and concentrated to give methyl 2-(3,5-dimethoxyphenyl)acetate (crude, 700 mg) as a yellow oil. MS (ES+) $C_{11}H_{14}O_4$ requires: 210, found: 211 [M+H]⁺.

Step 5: Synthesis of 6-(3,5-dimethoxyphenyl)-8-methyl-2-(methylthio)pyrido[2,3-d]pyrimidin-7(8H)-one

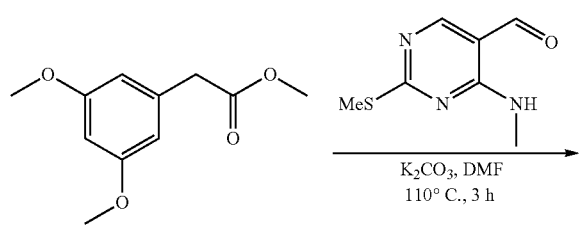

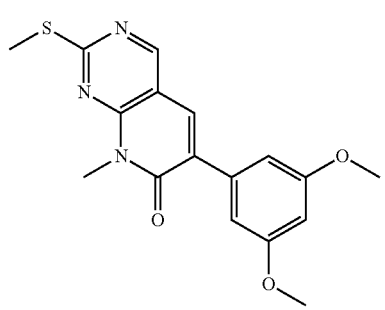

A solution of 2-(3,5-dimethoxyphenyl)acetate (6) (440 mg, 2.40 mmol), 4-amino-2-(methylthio)pyrimidine-5-carbaldehyde (4) (605 mg, 2.88 mmol) and potassium carbonate (662 mg, 4.8 mmol) in DMF (30 mL) was stirred at 110° C. for 3 hours. The reaction was monitored by LCMS. The reaction mixture was diluted with H₂O (30 mL), and extracted by EtOAc (3×40 mL). The combined organic layers were washed with water and brine, dried over sodium sulfate, filtered and concentrated. The residue was purified by column chromatography (silica gel, petroleum ether/EtOAc=2:1) to afford 6-(3,5-dimethoxyphenyl)-8-methyl-2-(methylthio)pyrido[2,3-d]pyrimidin-7(8H)-one (7) (683 mg, 83%) as a white solid. MS (ES+) $C_{17}H_{17}N_3O_5S$ requires: 343, found: 344 [M+H]⁺.

Step 6: Synthesis of 6-(3,5-dimethoxyphenyl)-8-methyl-2-(methylsulfonyl)pyrido[2,3-d]pyrimidin-7(8H)-one

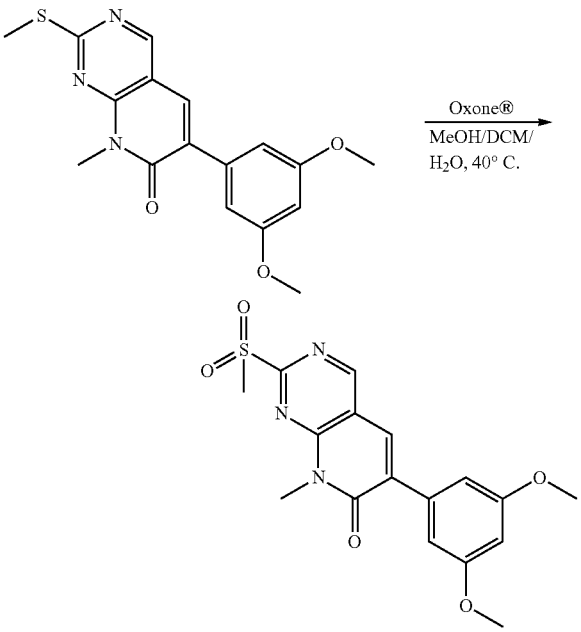

To a solution of 6-(3,5-dimethoxyphenyl)-8-methyl-2-(methylthio)pyrido[2,3-d]pyrimidin-7(8H)-one (1.05 g, 3.1 mmol) in methanol/dichloromethane (MeOH/DCM) (20 mL/20 mL) was added a solution of Oxone® (potassium peroxymonosulfate) (11.3 g, 18.4 mmol) in H₂O (20 mL) at room temperature, and the reaction mixture was stirred at 40° C. for 18 hours. The reaction was monitored by LCMS. The reaction mixture was diluted with H₂O/DCM (150 mL/100 mL), and the aqueous phase was extracted with DCM (100 mL). The combined organic layers were washed with water (200 mL) and brine (200 mL), dried over sodium sulfate, filtered, and concentrated. The crude product was recrystallizated with EtOAc to afford 6-(3,5-dimethoxyphenyl)-8-methyl-2-(methylsulfonyl)pyrido[2,3-d]pyrimidin-7 (8H)-one (8) (910 mg, yield 78%) as yellow solid. MS (ES+) $C_{17}H_{17}N_3O_5S$, requires: 375, found: 376 [M+H]⁺.

Step 7: Synthesis of 6-(2,6-dichloro-3,5-dimethoxyphenyl)-8-methyl-2-(methylsulfonyl)pyrido[2,3-d]pyrimidin-7(8H)-one

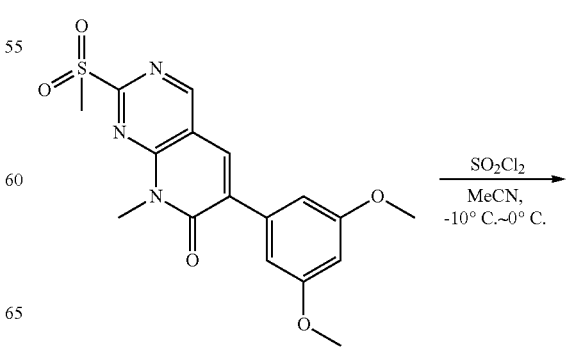

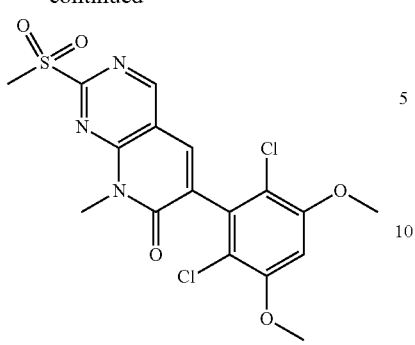

To a solution of 6-(3,5-dimethoxyphenyl)-8-methyl-2-(methylsulfonyl)pyrido[2,3-d]pyrimidin-7(8H)-one (8) (938 mg, 2.5 mmol) in acetonitrile (50 mL) was slowly added a solution of sulfuryl chloride (1.34 g, 10.0 mmol) in acetonitrile (25 mL) over a period of 0.5 hour at a temperature ranging from −10° C. to 0° C. The reaction was monitored by thin layer chromatography (TLC). The reaction mixture was quenched by adding H$_2$O (10 mL). The resultant reaction solution was concentrated under reduced pressure, and the residue was recrystallizated with EtOAc/petroleum ether=1:2 to give 6-(2,6-dichloro-3,5-dimethoxyphenyl)-8-methyl-2-(methylsulfonyl)pyrido[2,3-d]pyrimidin-7(8H)-one (9) (760 mg, 69% yield) as yellow solid. MS (ES+) C$_{17}$H$_{15}$Cl$_2$N$_3$O$_5$S requires: 443, 445, found: 444, 446 [M+H]$^+$.

Synthesis of Common Intermediates:

Intermediate A: 7-fluoro-2,2-dimethyl-6-(4,4,5,5-tetramethyl-1,3,2-dioxaborolan-2-yl)-3,4-dihydro-2H-benzo[b][1,4]oxazine Step 1: Synthesis of 6-bromo-7-fluoro-2,2-dimethyl-2H-benzo[b][1,4]oxazin-3(4H)-one

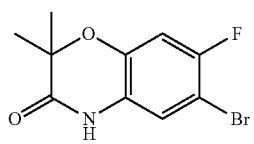

2-amino-4-bromo-5-fluorophenol hydrochloride (1.0 g, 4.12 mmol) was taken up in dichloroethane (10 ml) and 2-bromo-2-methylpropanoyl bromide (0.692 ml, 4.54 mmol) was added, followed by addition of DIEA (0.720 ml, 4.12 mmol). Stirred at room temperature for 3 hours. Reaction was cooled to 0° C. and water added, stirred at 0° C. for 10 minutes. Layers were separated and solvent removed. Residue was then taken back up in acetonitrile and K2CO3 (1.65 g, 12 mmol) added. Reaction was then heated to reflux overnight. Complete conversion to desired product. Filtered of solid and removed solvent. The residue was purified via flash chromatography (0-40% Hex/EtOAc; 12 g column). Recovered 6-bromo-7-fluoro-2,2-dimethyl-2H-benzo[b][1,4]oxazin-3(4H)-one (0.270 g, 24% yield) as a pink solid. LCMS M+H: 275

Step 2: Synthesis of 6-bromo-7-fluoro-2,2-dimethyl-3,4-dihydro-2H-benzo[b][1,4]oxazine

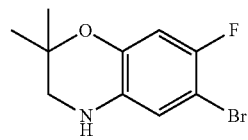

6-bromo-7-fluoro-2,2-dimethyl-2H-benzo[b][1,4]oxazin-3(4H)-one (0.270 g, 0.985 mmol) was taken up in THF (5 ml) and BH3.DMS (1.970 ml, 3.94 mmol) was added slowly at room temperature. The reaction was heated to reflux for 2 hours. Reaction was removed from oil bath and cooled to room temperature and quenched slowly with Methanol(1 ml). Mixture was stirred overnight at room temperature. Diluted with DCM and water, separated layers and removed solvent to give title compound, (0.211 g, 82% yield), that was carried on without purification. LCMS M+H: 261

Step 3: Synthesis of 7-fluoro-2,2-dimethyl-6-(4,4,5,5-tetramethyl-1,3,2-dioxaborolan-2-yl)-3,4-dihydro-2H-benzo[b][1,4]oxazine

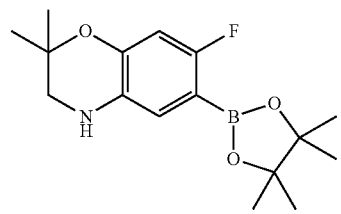

6-bromo-7-fluoro-2,2-dimethyl-3,4-dihydro-2H-benzo[b][1,4]oxazine (0.210 g, 0.807 mmol), BIS(PINACOLATO)DIBORON (0.410 g, 1.615 mmol), PdCl2(dppf)-CH2Cl2Adduct (0.066 g, 0.081 mmol), and POTASSIUM ACETATE (0.238 g, 2.422 mmol) were sealed in a 20 ml reaction tube. The tube was evacuated and purged with N$_2$. Addition of Dioxane (8.07 ml) followed purging with N$_2$. Reaction was heated to 100° C. overnight. Cooled to room temperature and partitioned between EtOAc/water, filtered through celite. Layers were separated and aqueous layer extracted with EtOAcx2. Combined organics were washed with brinex2. Dried over Na2SO4 and solvent removed. Recovered 7-fluoro-2,2-dimethyl-6-(4,4,5,5-tetramethyl-1,3,2-dioxaborolan-2-yl)-3,4-dihydro-2H-benzo[b][1,4]oxazine (0.147 g, 0.479 mmol, 59.3% yield) crude was carried on as is. LCMS M+H: 308.

Intermediate B: 7-methyl-6-(4,4,5,5-tetramethyl-1,3,2-dioxaborolan-2-yl)-3,4-dihydro-2H-benzo[b][1,4]oxazine Step 1: Synthesis of 7-methyl-2H-benzo[b][1,4]oxazin-3(4H)-one

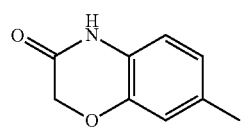

To a solution of 2-amino-5-methyl-phenol (3.0 g, 24.4 mmol) in acetonitrile (203 mL), 2-chloroacetyl chloride (2.75 g, 24.4 mmol) was added dropwise over 20 minutes, followed by potassium carbonate (10.1 g, 73.1 mmol). The reaction mixture was heated at reflux for 2 hours, then cooled to room temperature. The mixture was filtered and the solid was washed with 50 mL of acetonitrile. The filtrate was concentrated under vacuum. The residue was dissolved into dichloromethane (200 mL), washed with water (100 mL), dried over sodium sulfate, filtered, and concentrated under vacuum to yield 7-methyl-2H-benzo[b][1,4]oxazin-3(4H)-one (1.6 g, 40% yield) as a beige/brown solid MS: M+1=164.1.

Step 2: Synthesis of 6-bromo-7-methyl-2H-benzo[b][1,4]oxazin-3(4H)-one

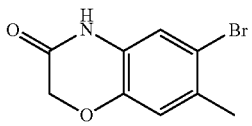

To a stirred suspension of 7-methyl-2H-benzo[b][1,4]oxazin-3(4H)-one (1.065 g, 6.53 mmol) in carbon tetrachloride (22 mL) was added dropwise over 20-25 minutes a solution of bromine (1.046 g, 6.55 mmol) in carbon tetrachloride (14 mL). The suspension was stirred over 5 hours. The reaction progressed slowly to nearly 70% completion. The mixture was then filtered. The solid was washed with carbon tetrachloride followed by DCM. The filtrate was concentrated down and purified by silica gel chromatography to yield were collected, concentrated down, and dried to yield 6-bromo-7-methyl-2H-benzo[b][1,4]oxazin-3(4H)-one (0.42 g, 27% yield). MS: M+1=242.0.

Step 3: Synthesis of 6-bromo-7-methyl-3,4-dihydro-2H-benzo[b][1,4]oxazine

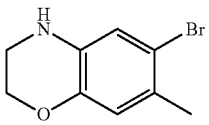

6-Bromo-7-methyl-2H-benzo[b][1,4]oxazin-3(4H)-one (84.6 mg, 0.349 mmol) was stirred at 0° C. in tetrahydrofuran (2 mL), and borane-methyl sulfide complex (0.35 mL of 2N in THF solution, 0.701 mmol) was added slowly over 5 minutes. The reaction was warmed to room temperature and then stirred at 70-75° C. for nearly 2 hours. The reaction was quenched by cooling the clear solution back to 0° C. and slowly adding 1N aqueous HCl (0.2 mL). The solution was then stirred 1 hour at 70° C. After cooling to room temperature, the solution was basified to pH 8-9 with aqueous 1N NaOH, diluted with water (~8 mL), and extracted with EtOAc (~20 mL). The organic extract was dried over sodium sulfate, filtered, concentrated down, and dried to yield 6-bromo-7-methyl-3,4-dihydro-2H-benzo[b][1,4]oxazine (89 mg, 90% purity, 100% yield). MS: M+1=228.0.

Step 4: Synthesis of 7-methyl-6-(4,4,5,5-tetramethyl-1,3,2-dioxaborolan-2-yl)-3,4-dihydro-2H-benzo[b][1,4]oxazine

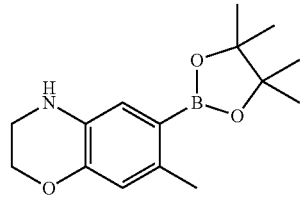 [SMILES: Cc1cc2c(cc1B1OC(C)(C)C(C)(C)O1)NCCO2]

A mixture of 6-bromo-7-methyl-3,4-dihydro-2H-benzo[b][1,4]oxazine (89 mg, 90% purity, 0.351 mmol), bis(pinacolato)diboron (134 mg, 0.526 mmol), and potassium acetate (103 mg, 1.05 mmol) in 1,4-dioxane (3.5 mL) was degassed with nitrogen for 5 min at RT and heated at 100° C. under a nitrogen atmosphere. After 30 min, dichloro[1,1'-bis(diphenylphosphino)-ferrocene]palladium (II) DCM adduct (28.6 mg, 0.035 mmol) was added, and the reaction mixture was stirred at 100° C. After 18 hours, the reaction was cooled to room temperature and filtered with EtOAc through a celite plug. The filtrate was concentrated down and partially purified by silica gel chromatography to yield 7-methyl-6-(4,4,5,5-tetramethyl-1,3,2-dioxaborolan-2-yl)-3,4-dihydro-2H-benzo[b][1,4]oxazine (137.8 mg, 70% purity, 100% yield) as a light amber oil. MS: M+1=276.2.

Intermediate C: 7-fluoro-6-(4,4,5,5-tetramethyl-1,3,2-dioxaborolan-2-yl)-3,4-dihydro-2H-benzo[b][1,4]oxazine

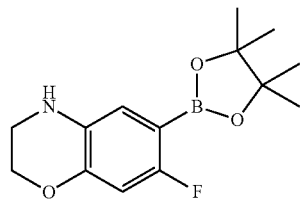 [SMILES: CC1(C)OB(c2cc3c(cc2F)OCCN3)OC1(C)C]

7-Fluoro-6-(4,4,5,5-tetramethyl-1,3,2-dioxaborolan-2-yl)-3,4-dihydro-2H-benzo[b][1,4]oxazine was prepared in similar manner as 7-methyl-6-(4,4,5,5-tetramethyl-1,3,2-dioxaborolan-2-yl)-3,4-dihydro-2H-benzo[b][1,4]oxazine from commercially available 6-bromo-7-fluoro-3,4-dihydro-2H-benzo[b][1,4]oxazine. MS: M+1=280.1.

Intermediate D: 7-fluoro-3-methyl-6-(4,4,5,5-tetramethyl-1,3,2-dioxaborolan-2-yl)-3,4-dihydro-2H-benzo[b][1,4]oxazine Step 1: Synthesis of 6-bromo-7-fluoro-3-methyl-2H-benzo[b][1,4]oxazine

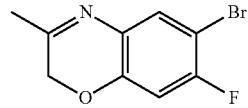

To a stirred 0° C. solution of 2-amino-4-bromo-5-fluorophenol (713 mg, 2.94 mmol) in acetone (2 mL) were added chloroacetone (299 mg, 3.23 mmol) and potassium carbonate (447 mg, 3.23 mmol). The mixture was warmed to room temperature and stirred 16 hours. A white solid was removed by filtration. The filtrate was concentrated down and dried to yield 6-bromo-7-fluoro-3-methyl-2H-benzo[b][1,4]oxazine (660 mg, 92% yield) as a rust-colored solid. MS: M+1=243.9.

Step 2: Synthesis of 6-bromo-7-fluoro-3-methyl-3,4-dihydro-2H-benzo[b][1,4]oxazine

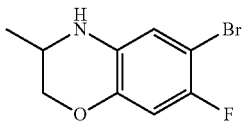

To a stirred mixture of 6-bromo-7-fluoro-3-methyl-2H-benzo[b][1,4]oxazine (660 mg, 2.70 mmol) in trifluoroacetic acid (10 mL) was added in small portions sodium cyanoborohydride (170 mg, 2.70 mmol)). After addition, the mixture was stirred about 3 hours. The mixture was slowly added to 150 mL of 2N aqueous NaOH and extracted with ethyl acetate (2×100 mL). The organic layers were washed with water, combined, dried over sodium sulfate, filtered, concentrated down, and dried to yield 6-bromo-7-fluoro-3-methyl-3,4-dihydro-2H-benzo[b][1,4]oxazine (602 mg, 83% yield) as a brown, thick oil. MS: M+1=247.9.

Step 3: Synthesis of 7-fluoro-3-methyl-6-(4,4,5,5-tetramethyl-1,3,2-dioxaborolan-2-yl)-3,4-dihydro-2H-benzo[b][1,4]oxazine

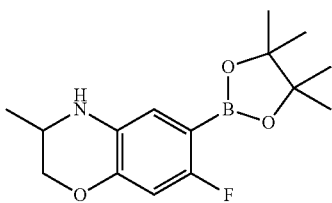

7-Fluoro-3-methyl-6-(4,4,5,5-tetramethyl-1,3,2-dioxaborolan-2-yl)-3,4-dihydro-2H-benzo[b][1,4]oxazine was prepared in similar manner as 7-methyl-6-(4,4,5,5-tetramethyl-1,3,2-dioxaborolan-2-yl)-3,4-dihydro-2H-benzo[b][1,4]oxazine from -bromo-7-fluoro-3-methyl-3,4-dihydro-2H-benzo[b][1,4]oxazine. MS: M+1=294.1.

General Protocol for Coupling Reaction

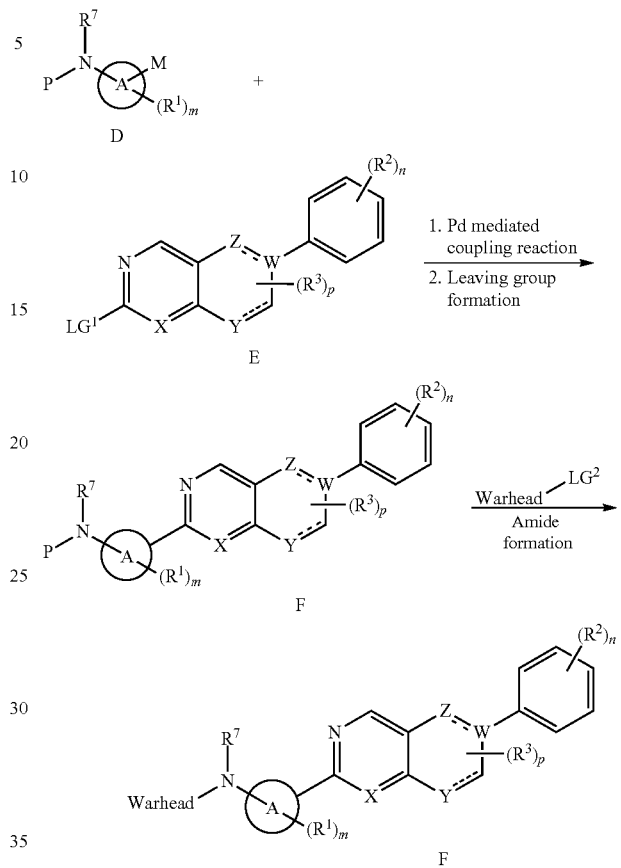

Aromatic bicycle (E) ($LG^1$ can be e.g., Cl, Br, or I; and P can be hydrogen or a protecting group) can be reacted with a boron, tin or zinc aryl or heteroaryl amine (D) (M can be —$B(OR)_2$ where R is hydrogen or alkyl, —$Sn(alkyl)_3$, or —Zn-halo) via a palladium-mediated coupling reaction, e.g., Suzuki, Stille, or Negishi coupling, to provide intermediate (E) with a new carbon-carbon bond formed. The amino group of intermediate (E) can be reacted with a carboxylic acid, or an ester, e.g., an activated ester, such as an N-hydroxysuccinimide ester, or an acyl chloride, to provide compounds of Formula I.

$^1$H NMR and LCMS data for Compounds 1 to 56 is summarized below. The compounds below can be synthesized using procedures analogous to the Synthetic Examples noted in the table.

| Compound Number | Synthetic Example | $^1$H NMR | LC MS (M + 1) |
|---|---|---|---|
| 1 | 1 | $^1$H NMR (400 MHz, DMSO-d6) δ 11.57 (s, 1H), 9.52 (s, 1H), 8.35 (s, 1H), 8.30 (d, J = 8.2 Hz, 1H), 8.14 (d, J = 8.5 Hz, 1H), 8.10-8.06 (m, 1H), 7.88 (dd, J = 7.8, 1.5 Hz, 1H), 7.66 (dd, J = 8.5, 1.7 Hz, 1H), 7.46 (td, J = 8.3, 7.8, 1.5 Hz, 1H), 7.30 (td, J = 7.5, 1.3 Hz, 1H), 7.05 (s, 1H), 6.43 (dd, J = 17.0, 10.2 Hz, 1H), 6.23 (dd, J = 17.0, 1.7 Hz, 1H), 5.75 (dd, J = 10.2, 1.7 Hz, 1H), 3.99 (s, 6H). | 479 |
| 2 | 1 | $^1$H NMR (400 MHz, DMSO-d6) δ 13.00 (s, 1H), 9.85 (s, 1H), 8.71 (dd, J = 14.5, 8.1 Hz, 2H), 8.26 (d, J = | 480 |

-continued

| Compound Number | Synthetic Example | $^1$H NMR | LC MS (M + 1) |
|---|---|---|---|
| | | 8.7 Hz, 1H), 8.16 (d, J = 1.9 Hz, 1H), 7.95 (dd, J = 8.7, 1.9 Hz, 1H), 7.59 (t, J = 7.6 Hz, 1H), 7.32 (t, J = 7.7 Hz, 1H), 7.08 (s, 1H), 6.65 (dd, J = 16.9, 10.2 Hz, 1H), 6.37 (d, J = 16.8 Hz, 1H), 5.90 (d, J = 10.3 Hz, 1H), 4.01 (s, 6H). | |
| 3 | 1 | | 480 |
| 4 | 2 | $^1$H NMR (400 MHz, DMSO-d6) δ 10.36 (s, 1H), 9.04 (s, 1H), 8.34 (dd, J = 7.2, 2.3 Hz, 1H), 8.23 (s, 1H), 8.01 (s, 1H), 7.92-7.83 (m, 1H), 7.36 (dd, J = 11.2, 8.9 Hz, 1H), 6.89 (d, J = 2.3 Hz, 2H), 6.55 (t, J = 2.3 Hz, 1H), 6.43 (dd, J = 17.0, 10.1 Hz, 1H), 6.28 (dd, J = 17.0, 2.1 Hz, 1H), 5.77 (dd, J = 10.1, 2.1 Hz, 1H), 5.56-5.38 (m, 1H), 3.79 (s, 6H), 1.59 (d, J = 7.0 Hz, 6H). | 488 |
| 5 | 1 | $^1$H NMR (400 MHz, DMSO-d6) δ 10.27 (s, 1H), 9.76 (s, 1H), 8.23 (d, J = 2.3 Hz, 1H), 8.13 (d, J = 8.7 Hz, 1H), 8.10 (d, J = 2.0 Hz, 1H), 7.87 (dd, J = 8.6, 2.0 Hz, 1H), 7.85-7.77 (m, 1H), 7.32 (d, J = 8.3 Hz, 1H), 7.06 (s, 1H), 6.45 (dd, J = 17.0, 10.1 Hz, 1H), 6.26 (dd, J = 16.9, 1.9 Hz, 1H), 5.75 (dd, J = 10.1, 1.8 Hz, 1H), 3.99 (s, 6H), 2.56 (s, 3H). | 494 |
| 6 | 1 | $^1$H NMR (400 MHz, DMSO-d6) δ 9.77 (d, J = 0.9 Hz, 1H), 8.57 (dt, J = 7.9, 1.4 Hz, 1H), 8.40 (t, J = 1.9 Hz, 1H), 8.21-8.13 (m, 1H), 8.09 (d, J = 1.9 Hz, 1H), 7.87 (dd, J = 8.6, 2.0 Hz, 1H), 7.68 (t, J = 7.8 Hz, 1H), 7.51 (ddd, J = 8.0, 2.3, 1.1 Hz, 1H), 7.06 (s, 1H), 6.19 (m, 2H), 5.64-5.56 (m, 1H), 3.99 (s, 6H), 3.35 (s, 3H). | 494 |
| 7 | 1 | | 498 |
| 8 | 1 | $^1$H NMR (300 MHz, DMSO-d6) δ 10.44 (s, 1H), 9.80 (s, 1H), 8.47 (dd, J = 6.9, 2.8 Hz, 1H), 8.17 (d, J = 8.7 Hz, 1H), 8.13 (d, J = 1.9 Hz, 1H), 8.00-7.93 (m, 1H), 7.91 (dd, J = 8.7, 2.0 Hz, 1H), 7.38 (dd, J = 10.6, 8.9 Hz, 1H), 7.08 (s, 1H), 6.47 (dd, J = 16.9, 9.9 Hz, 1H), 6.30 (dd, J = 16.9, 2.2 Hz, 1H), 5.80 (dd, J = 9.9, 2.2 Hz, 1H), 4.00 (s, 6H). | 498 |
| 9 | 2 | $^1$H NMR (400 MHz, DMSO-d6) δ 11.84 (s, 1H), 11.33 (s, 1H), 9.04 (s, 1H), 8.16 (s, 2H), 7.79 (dd, J = 2.5, 1.5 Hz, 3H), 7.66 (s, 1H), 7.50-7.40 (m, 1H), 7.28 (t, J = 7.5 Hz, 1H), 6.38 (dd, J = 17.0, 10.2 Hz, 1H), 6.17 (dd, J = 17.0, 1.7 Hz, 1H), 5.71 (dd, J = 10.2, 1.7 Hz, 1H), 4.34 (q, J = 7.1 Hz, 2H), 3.67 (s, 3H), 1.21 (t, J = 7.0 Hz, 3H). | 503 |
| 10 | 2 | 1H NMR (400 MHz, DMSO-d6) δ 10.37 (s, 1H), 9.03 (s, 1H), 8.38-8.29 (m, 1H), 8.13 (s, 1H), 8.03 (s, 1H), 7.89 (dq, J = 8.8, 2.9 Hz, 1H), 7.37 (dd, J = 11.2, 9.0 Hz, 1H), 6.79 (dd, J = 6.9, 3.0 Hz, 1H), 6.57 (dd, J = 4.8, 2.9 Hz, 1H), 6.43 (dd, J = 17.0, 10.1 Hz, 1H), 6.28 (dd, J = 17.0, 2.0 Hz, 1H), 5.78 (dd, J = 10.0, 2.1 Hz, 1H), 5.48-5.35 (m, 1H), 3.86 (s, 3H), 3.78 (s, 3H), 1.58 (d, J = 6.9 Hz, 6H). | 506 |
| 11 | 1 | 1H NMR (400 MHz, DMSO-d6) δ 9.73 (s, 1H), 9.39 (s, 1H), 8.32 (dd, J = 7.8, 1.6 Hz, 1H), 8.14 (d, J = 8.7 Hz, 1H), 8.06 (d, J = 1.9 Hz, 1H), 7.84 (dd, J = 8.6, 2.0 Hz, 1H), 7.44 (d, J = 7.9 Hz, 1H), 7.05 (s, 1H), 6.81 (dd, J = 16.7, 10.2 Hz, 1H), 6.42-6.29 (m, 1H), 5.86 (d, J = 10.4 Hz, 1H), 4.30 (t, J = 8.5 Hz, 2H), 3.29-3.21 (m, 2H). | 506 |
| 12 | 2 | $^1$H NMR (400 MHz, DMSO-d6) δ 10.37 (s, 1H), 9.05 (s, 1H), 8.32 (dd, J = 7.1, 2.8 Hz, 1H), 8.07 (s, 1H), 7.96-7.81 (m, 2H), 7.37 (dd, J = 11.0, 8.9 Hz, 1H), 6.78 (d, J = 2.8 Hz, 1H), 6.63 (d, J = 2.7 Hz, 1H), 6.44 (dd, J = 17.0, 10.0 Hz, 1H), 6.28 (dd, J = 17.0, 2.1 Hz, 1H), 5.83-5.71 (m, 1H), 4.33 (q, J = 7.0 Hz, 2H), 3.88 (s, 3H), 3.80 (s, 3H), 1.27 (t, J = 7.1 Hz, 3H). | 508 |
| 13 | 1 | $^1$H NMR (400 MHz, DMSO-d$_6$) δ 10.43 (s, 1H), 9.69 (s, 1H), 8.74 (t, J = 1.9 Hz, 1H), 8.28 (d, J = 7.8 Hz, 1H), 8.03 (dd, J = 8.2, 1.8 Hz, 1H), 7.61-7.46 (m, 2H), 7.30 (d, J = 1.6 Hz, 1H), 7.05 (s, 1H), 6.50 (dd, J = 16.9, 10.1 Hz, 1H), 6.30 (dd, J = 16.9, 2.0 Hz, 1H), 5.85-5.63 (m, 1H), 4.02 (s, 3H), 3.98 (s, 6H). | 511 |
| 14 | 1 | $^1$H NMR (400 MHz, DMSO-d$_6$) δ 13.85 (s, 1H), 9.80 (s, 1H), 8.85 (dd, J = 8.1, 1.9 Hz, 2H), 7.66 (d, J = 1.6 Hz, 1H), 7.57 (td, J = 8.4, 7.8, 1.7 Hz, 1H), 7.46 (d, J = 1.6 Hz, 1H), 7.35-7.19 (m, 1H), 7.07 (s, 1H), 6.75 (dd, J = 16.9, 10.2 Hz, 1H), 6.39 (dd, J = 17.0, 1.8 Hz, | 511 |

-continued

| Compound Number | Synthetic Example | ¹H NMR | LC MS (M + 1) |
|---|---|---|---|
| | | 1H), 5.98 (dd, J = 10.0, 1.8 Hz, 1H), 4.11 (s, 3H), 3.99 (s, 6H). | |
| 15 | 1 | ¹H NMR (400 MHz, DMSO-d₆) δ 12.99 (s, 1H), 9.63 (s, 1H), 8.67 (dt, J = 8.4, 2.3 Hz, 2H), 8.01 (s, 1H), 7.61 (s, 1H), 7.59-7.53 (m, 1H), 7.37-7.23 (m, 1H), 7.03 (s, 1H), 6.64 (dd, J = 16.9, 10.3 Hz, 1H), 6.36 (dd, J = 17.0, 1.5 Hz, 1H), 5.89 (dd, J = 10.2, 1.5 Hz, 1H), 3.98 (d, J = 1.8 Hz, 6H), 1.06 (s, 3H). | 511 |
| 16 | 1 | ¹H NMR (400 MHz, DMSO-d₆) δ 9.69 (s, 1H), 8.31 (dd, J = 8.7, 2.1 Hz, 1H), 8.08 (d, J = 8.7 Hz, 1H), 8.03 (d, J = 1.9 Hz, 1H), 7.82 (dd, J = 8.6, 2.0 Hz, 1H), 7.11 (d, J = 8.6 Hz, 1H), 7.05 (s, 1H), 6.88 (dd, J = 16.7, 10.4 Hz, 1H), 6.35 (dd, J = 16.8, 2.1 Hz, 1H), 5.89 (dd, J = 10.4, 2.1 Hz, 1H), 4.39 (t, J = 4.5 Hz, 2H), 4.03 (d, J = 4.7 Hz, 2H), 3.99 (s, 6H). | 523 |
| 17 | 2 | | |
| 18 | 1 | | 524 |
| 19 | 2 | ¹H NMR (400 MHz, DMSO-d₆) δ 11.25 (s, 1H), 9.07 (s, 1H), 8.22 (d, J = 8.4 Hz, 1H), 8.09 (s, 1H), 7.91 (d, J = 7.5 Hz, 1H), 7.82 (s, 1H), 7.49 (t, J = 7.7 Hz, 1H), 7.32 (t, J = 7.6 Hz, 1H), 7.02 (s, 1H), 6.43 (dd, J = 17.0, 10.2 Hz, 1H), 6.22 (dd, J = 17.0, 1.7 Hz, 1H), 5.74 (dd, J = 10.1, 1.8 Hz, 1H), 4.37 (q, J = 7.9, 7.5 Hz, 2H), 3.97 (s, 6H), 1.23 (t, J = 7.0 Hz, 3H). | 524 |
| 20 | 2 | ¹H NMR (400 MHz, DMSO-d6) δ 10.34 (s, 1H), 9.02 (s, 1H), 8.46 (t, J = 2.0 Hz, 1H), 8.05 (s, 1H), 8.02-7.87 (m, 3H), 7.50 (t, J = 7.9 Hz, 1H), 7.01 (s, 1H), 6.48 (dd, J = 17.0, 10.1 Hz, 1H), 6.29 (dd, J = 16.9, 2.0 Hz, 1H), 5.78 (dd, J = 10.1, 2.1 Hz, 1H), 4.43 (q, J = 7.0 Hz, 2H), 3.97 (s, 6H), 1.27 (t, J = 7.1 Hz, 3H). | 524 |
| 21 | 1 | ¹H NMR (400 MHz, DMSO-d6) δ 10.38 (s, 1H), 9.06 (s, 1H), 8.31 (dd, J = 7.1, 2.8 Hz, 1H), 8.18 (s, 1H), 7.97-7.82 (m, 2H), 7.37 (dd, J = 11.0, 8.9 Hz, 1H), 7.06 (d, J = 7.8 Hz, 1H), 6.44 (dd, J = 17.0, 10.0 Hz, 1H), 6.28 (dd, J = 17.0, 2.1 Hz, 1H), 5.78 (dd, J = 10.0, 2.1 Hz, 1H), 4.33 (q, J = 7.0 Hz, 2H), 3.94 (s, 3H), 3.93 (s, 3H), 1.27 (t, J = 7.0 Hz, 3H). | 526 |
| 22 | 3 | ¹H NMR (400 MHz, DMSO-d6) δ 10.29 (s, 1H), 8.38 (s, 1H), 8.32 (s, 1H), 7.87 (d, J = 8.1 Hz, 1H), 7.80 (d, J = 7.8 Hz, 1H), 7.50-7.39 (m, 2H), 6.99 (s, 1H), 6.46 (dd, J = 16.9, 10.1 Hz, 1H), 6.28 (dd, J = 17.0, 2.0 Hz, 1H), 5.77 (dd, J = 10.1, 2.1 Hz, 1H), 4.71 (s, 2H), 4.01 (q, J = 7.2 Hz, 2H), 3.96 (s, 6H), 1.21 (t, J = 6.9 Hz, 3H). | 527 |
| 23 | 2 | ¹H NMR (400 MHz, DMSO-d6) δ 10.38 (s, 1H), 9.06 (s, 1H), 8.32 (dd, J = 7.1, 2.8 Hz, 1H), 8.08 (s, 1H), 7.94-7.88 (m, 1H), 7.88 (s, 1H), 7.41-7.34 (m, 1H), 7.02 (s, 1H), 6.44 (dd, J = 17.0, 10.1 Hz, 1H), 6.28 (dd, J = 17.0, 2.1 Hz, 1H), 5.78 (dd, J = 10.0, 2.1 Hz, 1H), 3.97 (s, 6H), 3.70 (s, 3H). | 528 |
| 24 | 1 | ¹H NMR (500 MHz, DMSO-d6) δ 9.70 (s, 1H), 8.08 (d, J = 8.7 Hz, 1H), 8.05 (d, J = 1.9 Hz, 1H), 7.83 (dd, J = 8.6, 2.0 Hz, 1H), 7.05 (s, 1H), 6.93 (s, 1H), 6.89-6.79 (m, 1H), 6.32-6.25 (m, 1H), 5.82 (dd, J = 10.3, 2.1 Hz, 1H), 4.36 (t, J = 4.6 Hz, 2H), 3.99 (s, 6H), 3.33-3.29 (m, 8H), 2.62 (s, 3H). | 531 |
| 25 | 2 | ¹H NMR (400 MHz, DMSO-d6) δ 11.11 (s, 1H), 9.03 (s, 1H), 8.17 (d, J = 8.3 Hz, 1H), 8.03 (s, 1H), 7.91 (s, 1H), 7.88 (d, J = 7.8 Hz, 1H), 7.48 (t, J = 7.8 Hz, 1H), 7.32 (t, J = 7.6 Hz, 1H), 7.01 (s, 1H), 6.42 (dd, J = 17.0, 10.3 Hz, 1H), 6.26-6.17 (m, 1H), 5.74 (dd, J = 9.5, 1.9 Hz, 1H), 5.30-5.17 (m, 1H), 3.97 (s, 6H), 1.53 (d, J = 6.7 Hz, 6H). | 538 |
| 26 | 2 | | 538 |
| 27 | 2 | ¹H NMR (400 MHz, DMSO-d6) δ 10.21 (s, 1H), 9.01 (s, 1H), 8.07 (s, 1H), 7.78 (s, 1H), 7.73 (d, J = 8.5 Hz, 1H), 7.64 (s, 1H), 7.30 (d, J = 8.4 Hz, 1H), 7.02 (s, 1H), 6.44 (dd, J = 16.9, 10.1 Hz, 1H), 6.25 (dd, J = 16.9, 2.1 Hz, 1H), 5.74 (dd, J = 10.1, 1.9 Hz, 1H), 4.34 (q, J = 7.4 Hz, 2H), 3.97 (s, 6H), 2.34 (s, 3H), 1.23 (t, J = 7.0 Hz, 3H). | 538 |
| 28 | 1 | ¹H NMR (500 MHz, DMSO-d6) δ 9.72 (s, 1H), 8.47 (b.s., 1H), 8.10 (d, J = 8.7 Hz, 1H), 8.06 (d, J = 1.9 Hz, 1H), 7.85 (dd, J = 8.7, 2.0 Hz, 1H), 7.05 (s, 1H), 6.99 (d, J = 11.7 Hz, 1H), 6.94-6.79 (m, 1H), 6.30 (dd, J = 16.8, 2.1 Hz, 1H), 5.86 (dd, J = 10.4, 2.1 Hz, | 540 |

-continued

| Compound Number | Synthetic Example | ¹H NMR | LC MS (M + 1) |
|---|---|---|---|
| 29 | 3 | 1H), 4.40 (t, J = 4.6 Hz, 2H), 4.02 (t, J = 4.7 Hz, 2H), 3.99 (s, 6H).<br>¹H NMR (400 MHz, DMSO-d6) δ 10.16 (s, 1H), 8.36 (s, 1H), 7.72 (s, 1H), 7.66 (d, J = 8.2 Hz, 1H), 7.25 (d, J = 8.3 Hz, 1H), 7.11 (s, 1H), 7.00 (s, 1H), 6.43 (dd, J = 16.9, 10.2 Hz, 1H), 6.24 (d, J = 16.9 Hz, 1H), 5.81-5.68 (m, 1H), 4.73 (s, 2H), 3.96 (s, 6H), 3.94-3.87 (m, 1H), 2.30 (s, 3H), 1.16 (t, J = 6.9 Hz, 3H). | 541 |
| 30 | 2 | ¹H NMR (400 MHz, DMSO-d6) δ 10.38 (s, 1H), 9.06 (s, 1H), 8.30 (dd, J = 7.1, 2.8 Hz, 1H), 8.08 (s, 1H), 7.94-7.86 (m, 2H), 7.37 (dd, J = 11.0, 8.9 Hz, 1H), 7.02 (s, 1H), 6.44 (dd, J = 16.9, 10.0 Hz, 1H), 6.28 (dd, J = 17.0, 2.1 Hz, 1H), 5.78 (dd, J = 10.0, 2.1 Hz, 1H), 4.34 (q, J = 7.1 Hz, 2H), 3.97 (s, 6H), 1.26 (t, J = 7.0 Hz, 3H). | 542 |
| 31 | 4 | ¹H NMR (400 MHz, DMSO-d6) δ 10.40 (s, 1H), 9.27 (s, 1H), 8.56 (dd, J = 7.0, 2.8 Hz, 1H), 8.08 (s, 1H), 7.93 (dt, J = 9.0, 3.4 Hz, 1H), 7.37 (dd, J = 10.9, 8.9 Hz, 1H), 7.03 (s, 1H), 6.44 (dd, J = 17.0, 10.1 Hz, 1H), 6.29 (dd, J = 17.0, 2.0 Hz, 1H), 5.79 (dd, J = 10.1, 2.1 Hz, 1H), 4.48 (q, J = 6.9 Hz, 2H), 3.97 (s, 6H), 1.29 (t, J = 7.0 Hz, 3H). | 543 |
| 32 | 3 | ¹H NMR (400 MHz, DMSO-d6) δ 10.32 (s, 1H), 8.42 (s, 1H), 8.19 (dd, J = 7.2, 2.7 Hz, 1H), 7.90-7.79 (m, 1H), 7.39 (s, 1H), 7.32 (dd, J = 10.9, 8.9 Hz, 1H), 7.00 (s, 1H), 6.42 (dd, J = 17.0, 10.1 Hz, 1H), 6.27 (dd, J = 17.0, 2.1 Hz, 1H), 5.77 (dd, J = 10.0, 2.1 Hz, 1H), 4.73 (s, 2H), 3.96 (s, 6H), 3.95-3.87 (m, 2H), 1.19 (t, J = 7.0 Hz, 3H). | 545 |
| 33 | 1 | | 548 |
| 34 | 1 | 1H NMR (400 MHz, DMSO-d6) δ 9.69 (s, 1H), 8.31 (dd, J = 8.6, 2.1 Hz, 1H), 8.08 (d, J = 8.7 Hz, 1H), 8.03 (d, J = 1.9 Hz, 1H), 7.82 (dd, J = 8.7, 2.0 Hz, 1H), 7.06 (d, J = 7.9 Hz, 2H), 6.95 (dd, J = 16.7, 10.4 Hz, 1H), 6.39 (dd, J = 16.6, 2.1 Hz, 1H), 5.91 (dd, J = 10.3, 2.1 Hz, 1H), 3.99 (s, 6H), 3.86 (s, 2H), 1.32 (s, 6H). | 551 |
| 35 | 2 | ¹H NMR (400 MHz, DMSO-d6) δ 9.04 (s, 1H), 9.01 (s, 1H), 8.04 (s, 1H), 7.95-7.85 (m, 2H), 7.41 (d, J = 7.8 Hz, 1H), 7.01 (s, 1H), 6.79 (dd, J = 16.5, 9.9 Hz, 1H), 6.34 (dd, J = 16.7, 1.9 Hz, 1H), 5.85 (dd, J = 10.4, 2.2 Hz, 1H), 4.42 (q, J = 7.0 Hz, 2H), 4.29 (t, J = 8.4 Hz, 2H), 3.97 (s, 6H), 3.24 (t, J = 8.3 Hz, 2H), 1.27 (t, J = 7.0 Hz, 3H). | 550 |
| 36 | 1 | ¹H NMR (400 MHz, DMSO-d₆) δ 9.47 (s, 1H), 8.29 (dd, J = 8.6, 2.1 Hz, 1H), 7.87 (s, 1H), 7.48 (s, 1H), 7.09 (d, J = 8.6 Hz, 1H), 7.00 (s, 1H), 6.88 (dd, J = 16.9, 10.5 Hz, 1H), 6.35 (dd, J = 16.7, 2.1 Hz, 1H), 5.88 (dd, J = 10.4, 2.1 Hz, 1H), 4.38 (t, J = 4.6 Hz, 2H), 4.02 (t, J = 4.7 Hz, 2H), 3.97 (s, 6H), 3.92 (s, 3H). | 553 |
| 37 | 2 | ¹H NMR (400 MHz, DMSO-d6) δ 8.95 (s, 1H), 8.41-8.28 (m, 1H), 8.11-7.93 (m, 2H), 7.85 (s, 1H), 7.07 (d, J = 8.6 Hz, 1H), 7.01 (s, 1H), 6.85 (dd, J = 16.8, 10.4 Hz, 1H), 6.32 (dd, J = 16.8, 2.1 Hz, 1H), 5.85 (dd, J = 10.4, 2.1 Hz, 1H), 4.37 (t, J = 4.6 Hz, 4H), 4.00 (t, J = 4.6 Hz, 4H), 3.96 (s, 6H), 3.74 (s, 3H). | 552 |
| 38 | 1 | ¹H NMR (300 MHz, DMSO-d6) δ 9.73 (s, 1H), 8.12 (d, J = 8.7 Hz, 1H), 8.08 (d, J = 1.8 Hz, 1H), 7.87 (dd, J = 8.7, 1.9 Hz, 1H), 7.07 (d, J = 11.7 Hz, 1H), 6.93-6.77 (m, 2H), 6.32 (dd, J = 16.7, 1.9 Hz, 1H), 5.87 (dd, J = 10.4, 1.8 Hz, 1H), 4.45-4.20 (m, 1H), 4.00 (s, 6H), 3.48-3.36 (m, 2H), 1.21 (d, J = 7.0 Hz, 3H). | 554 |
| 39 | 2 | 1H NMR (400 MHz, DMSO-d6) δ 10.19 (s, 1H), 9.01 (s, 1H), 8.18 (d, J = 2.7 Hz, 1H), 8.05 (s, 1H), 8.03 (s, 1H) 7.88 (dd, J = 8.9, 2.8 Hz, 1H), 7.19 (d, J = 9.0 Hz, 1H), 7.01 (s, 1H), 6.43 (dd, J = 16.9, 10.1 Hz, 1H), 6.24 (dd, J = 17.0, 2.1 Hz, 1H), 5.73 (dd, J = 10.2, 2.1 Hz, 1H), 4.31 (q, J = 7.1 Hz, 2H), 3.97 (s, 6H), 3.89 (s, 3H), 1.29 (t, J = 7.1 Hz, 3H). | 554 |
| 40 | 2 | ¹H NMR (400 MHz, DMSO-d6) δ 10.38 (s, 1H), 9.04 (s, 1H), 8.37-8.25 (m, 1H), 8.04 (d, J = 10.4 Hz, 1H), 7.96-7.85 (m, 1H), 7.37 (dd, J = 11.1, 8.9 Hz, 1H), 7.01 (s, 1H), 6.44 (dd, J = 17.0, 10.1 Hz, 1H), 6.28 (dd, J = 17.0, 2.0 Hz, 1H), 5.78 (dd, J = 10.1, 2.1 | 556 |

-continued

| Compound Number | Synthetic Example | ¹H NMR | LC MS (M + 1) |
|---|---|---|---|
| | | Hz, 1H), 5.30-5.17 (m, 1H), 3.97 (s, 6H), 1.56 (d, J = 6.9 Hz, 6H). | |
| 41 | 2 | ¹H NMR (400 MHz, DMSO-d6) δ 10.56 (s, 1H), 9.08 (s, 1H), 8.12-8.03 (m, 2H), 7.98-7.95 (m, 2H), 7.02 (s, 1H), 6.42 (dd, J = 17.0, 9.9 Hz, 1H), 6.30 (dd, J = 17.0, 2.1 Hz, 1H), 5.81 (dd, J = 9.9, 2.1 Hz, 1H), 4.34 (q, J = 6.8 Hz, 2H), 3.97 (s, 6H), 1.26 (t, J = 7.0 Hz, 3H). | 560 |
| 42 | 2 | ¹H NMR (400 MHz, DMSO-$d_6$) δ 11.03 (s, 1H), 9.04 (s, 1H), 8.16 (d, J = 8.2 Hz, 1H), 8.05 (s, 1H), 7.96-7.77 (m, 2H), 7.48 (t, J = 7.9 Hz, 1H), 7.32 (t, J = 7.6 Hz, 1H), 7.01 (s, 1H), 6.42 (dd, J = 17.0, 10.2 Hz, 1H), 6.22 (d, J = 16.8 Hz, 1H), 5.74 (d, J = 9.5 Hz, 1H), 5.44 (s, 1H), 3.96 (s, 6H), 2.09 (s, 2H), 1.95 (d, J = 21.5 Hz, 3H), 1.62 (s, 2H), 1.19 (d, J = 26.6 Hz, 1H). | 565 |
| 43 | 2 | ¹H NMR (400 MHz, DMSO-$d_6$) δ 10.34 (s, 1H), 8.99 (s, 1H), 8.45 (s, 1H), 8.11 (s, 1H), 8.01 (s, 1H), 7.98-7.87 (m, 2H), 7.50 (t, J = 7.9 Hz, 1H), 7.01 (s, 1H), 6.48 (dd, J = 16.9, 9.8 Hz, 1H), 6.37-6.18 (m, 1H), 5.89-5.69 (m, 1H), 5.54 (d, J = 10.0 Hz, 1H), 3.96 (s, 6H), 2.13 (s, 2H), 1.99 (s, 3H), 1.67 (s, 2H), 1.23 (s, 1H). | 565 |
| 44 | 1 | ¹H NMR (400 MHz, DMSO-d6) δ 9.70 (s, 1H), 8.16-7.99 (m, 2H), 7.83 (dd, J = 8.6, 2.0 Hz, 1H), 7.06 (s, 1H), 6.88 (s, 1H), 6.39-6.27 (m, 1H), 5.85 (dd, J = 10.4, 2.1 Hz, 1H), 3.99 (s, 8H), 3.82 (s, 2H), 2.62 (s, 3H), 1.31 (s, 6H). | 565 |
| 45 | 2 | ¹H NMR (400 MHz, DMSO-$d_6$) δ 8.98 (s, 1H), 8.03 (d, J = 8.5 Hz, 3H), 7.92 (s, 1H), 7.39 (d, J = 7.9 Hz, 1H), 7.01 (s, 1H), 6.63 (dd, J = 16.7, 10.3 Hz, 1H), 6.31-6.21 (m, 1H), 5.77-5.67 (m, 1H), 4.42 (q, J = 7.0 Hz, 2H), 3.96 (d, J = 0.8 Hz, 6H), 3.80 (t, J = 6.5 Hz, 2H), 2.79 (t, J = 6.5 Hz, 2H), 1.97-1.89 (m, 2H), 1.24 (t, J = 7.0 Hz, 3H). | 564 |
| 46 | 4 | ¹H NMR (400 MHz, DMSO-$d_6$) δ 11.71 (s, 1H), 9.28 (d, J = 1.0 Hz, 1H), 8.44 (d, J = 8.3 Hz, 1H), 8.29 (dd, J = 8.0, 1.6 Hz, 1H), 8.08 (d, J = 1.1 Hz, 1H), 7.63-7.46 (m, 1H), 7.39-7.22 (m, 1H), 7.02 (s, 1H), 6.50 (dd, J = 17.0, 10.2 Hz, 1H), 6.27 (dd, J = 17.0, 1.6 Hz, 1H), 6.05 (q, J = 8.7 Hz, 1H), 5.79 (dd, J = 10.2, 1.6 Hz, 1H), 3.97 (s, 6H), 2.19 (d, J = 12.5 Hz, 2H), 1.93 (d, J = 19.0 Hz, 2H), 1.62 (s, 2H). | 566 |
| 47 | 2 | ¹H NMR (400 MHz, DMSO-d6) δ 8.95 (s, 1H), 8.30 (b.s., 1H), 8.04-7.98 (m, 2H), 7.87 (s, 1H), 7.07 (d, J = 8.6 Hz, 1H), 7.01 (s, 1H), 6.85 (dd, J = 16.7, 10.4 Hz, 1H), 6.32 (dd, J = 16.7, 2.1 Hz, 1H), 5.84 (dd, J = 10.4, 2.1 Hz, 1H), 4.47-4.33 (m, 4H), 4.00 (t, J = 4.7 Hz, 2H), 3.96 (s, 6H), 1.24 (t, J = 7.0 Hz, 3H). | 566 |
| 48 | 1 | ¹H NMR (400 MHz, DMSO-d6) δ 9.72 (s, 1H), 8.15-8.01 (m, 2H), 7.85 (dd, J = 8.7, 2.0 Hz, 1H), 7.06 (s, 1H), 6.94 (d, J = 11.8 Hz, 1H), 6.35 (dd, J = 16.7, 2.1 Hz, 1H), 5.89 (dd, J = 10.4, 2.1 Hz, 1H), 3.99 (s, 8H), 3.87 (s, 2H), 1.33 (s, 6H). | 569 |
| 49 | 2 | 1H NMR (400 MHz, DMSO-d6) δ 10.32 (s, 1H), 8.99 (s, 1H), 8.04 (s, 1H), 7.97 (d, J = 1.7 Hz, 1H), 7.90 (s, 1H), 7.65 (s, 1H), 7.49 (t, J = 1.9 Hz, 1H), 7.02 (s, 1H), 6.46 (dd, J = 16.9, 10.1 Hz, 1H), 6.29 (dd, J = 17.0, 2.1 Hz, 1H), 5.78 (dd, J = 10.0, 2.1 Hz, 1H), 4.70 (p, J = 6.0 Hz, 1H), 3.97 (s, 6H), 3.78 (s, 3H), 1.33 (d, J = 6.0 Hz, 6H). | 569 |
| 50 | 3 | 1H NMR (400 MHz, DMSO-d6) δ 8.31 (s, 1H), 8.14 (b.s., 1H), 7.85 (d, J = 8.2 Hz, 1H), 7.38 (s, 1H), 7.02 (d, J = 8.6 Hz, 1H), 6.99 (s, 1H), 6.83 (dd, J = 16.8, 10.3 Hz, 1H), 6.30 (dd, J = 16.7, 2.1 Hz, 1H), 5.83 (dd, 1H), 4.67 (s, 2H), 4.35 (t, J = 4.5 Hz, 2H), 4.05-3.97 (m, 4H), 3.95 (s, 6H), 1.18 (t, J = 6.9 Hz, 3H). | 569 |
| 51 | 2 | ¹H NMR (400 MHz, DMSO-$d_6$) δ 10.24 (s, 1H), 9.01 (d, J = 2.8 Hz, 1H), 8.46 (s, 1H), 8.05 (s, 1H), 7.97-7.77 (m, 3H), 7.48 (t, J = 8.3 Hz, 1H), 7.01 (s, 1H), 6.87-6.70 (m, 1H), 6.30 (d, J = 15.5 Hz, 1H), 4.42 (q, J = 8.6, 7.0 Hz, 2H), 3.97 (s, 6H), 3.06 (d, J = 5.7 Hz, 1H), 2.25 (s, 1H), 2.18 (s, 6H), 1.27 (t, J = 6.7 Hz, 3H). | 581 |

-continued

| Compound Number | Synthetic Example | $^1$H NMR | LC MS (M + 1) |
|---|---|---|---|
| 52 | 2 | | 595 |
| 53 | 2 | $^1$H NMR (300 MHz, DMSO-d6) δ 9.02 (s, 1H), 8.05 (s, 1H), 7.83 (s, 1H), 7.06 (d, J = 12.2 Hz, 1H), 7.02 (s, 1H), 6.93-6.72 (m, 2H), 6.31 (dd, J = 16.7, 1.7 Hz, 1H), 5.90-5.81 (m, 1H), 4.44-4.17 (m, 3H), 3.98 (s, 6H), 3.48-3.36 (m, 2H), 1.26 (t, J = 7.1 Hz, 3H), 1.19 (d, J = 6.8 Hz, 3H). | 598 |
| 54 | 2 | | 607 |
| 55 | 4 | $^1$H NMR (400 MHz, DMSO-d$_6$) δ 9.15 (s, 1H), 8.21 (dd, J = 8.6, 2.1 Hz, 1H), 7.98 (s, 1H), 7.11 (d, J = 8.7 Hz, 1H), 7.01 (s, 1H), 6.86 (dd, J = 16.7, 10.4 Hz, 1H), 6.33 (dd, J = 16.7, 2.1 Hz, 1H), 6.14-5.97 (m, 1H), 5.84 (dd, J = 10.4, 2.1 Hz, 1H), 4.47-4.33 (m, 2H), 4.01 (t, J = 4.6 Hz, 2H), 3.96 (s, 6H), 2.28 (d, J = 26.3 Hz, 2H), 1.93 (d, J = 35.6 Hz, 5H), 1.64 (s, 2H). | 608 |
| 56 | 2 | $^1$H NMR (400 MHz, DMSO-d6) δ 9.04 (s, 1H), 8.48-8.27 (m, 1H), 8.17 (s, 1H), 8.04 (dd, J = 8.6, 2.2 Hz, 1H), 7.13-7.03 (m, 1H), 6.85 (dd, J = 16.7, 10.4 Hz, 1H), 6.32 (dd, J = 16.8, 2.1 Hz, 1H), 5.84 (dd, J = 10.4, 2.1 Hz, 1H), 5.58-5.41 (m, 1H), 4.38 (t, J = 4.6 Hz, 4H), 4.01 (t, J = 4.5 Hz, 4H), 3.98 (s, 6H), 2.20-1.87 (m, 6H), 1.78-1.53 (m, 2H). | 607 |

Biochemical Activity Assessment

In order to assess the activity of chemical compounds against the relevant kinase of interest, the Caliper LifeSciences electrophoretic mobility shift technology platform is utilized. Fluorescently labeled substrate peptide is incubated in the presence of dosed levels of compounds, a set concentration of kinase and of ATP, so that a reflective proportion of the peptide is phosphorylated. At the end of the reaction, the mix of phosphorylated (product) and non-phosphorylated (substrate) peptides are passed through the microfluidic system of the Caliper LabChip® EZ Reader II, under an applied potential difference. The presence of the phosphate group on the product peptide provides a difference in mass and charge between the product peptide and the substrate peptide, resulting in a separation of the substrate and product pools in the sample. As the pools pass the LEDS within the instrument, these pools are detected and resolved as separate peaks. The ratio between these peaks therefore reflects the activity of the chemical matter at that concentration in that well, under those conditions.

FGFR-4 wild type assay at Km: In each well of a 384-well plate, 0.5 ng/ul of wild type FGFR-4 (Carna Biosciences, Inc.) was incubated in a total of 12.5 ul of buffer (100 mM HEPES pH 7.5, 0.015% Brij 35, 10 mM MgCl$_2$, 1 mM DTT) with 1 uM CSKtide (5-FAM-KKKKEEIYFFFG-NH$_2$) and 400 uM ATP at 25 C for 90 minutes in the presence or absence of a dosed concentration series of compound (1% DMSO final concentration). The reaction was stopped by the addition of 70 ul of Stop buffer (100 mM HEPES pH 7.5, 0.015% Brij 35, 35 mM EDTA and 0.2% of Coating Reagent 3 (Caliper Lifesciences)). The plate was then read on a Caliper LabChip® EZ Reader II (protocol settings: −1.9 psi, upstream voltage −700, downstream voltage −3000, post sample sip 35 s).

Detection of pMAPK (Thr202/Tyr204) Using Alpha Elisa

MDA-MB453 cells were plated in 96-well cell culture plates at a density of 1×10$^5$ cells. Cells were allowed to attach, and growth media was replaced with serum free media. Compounds were added at the indicated concentrations. Following 1 hr incubation in the presence of compound, cells were collected. Cell lysates were prepared and processed according to manufacturer instruction (AlphaScreen® SureFire™ Phospho-ERK 1/2 Kit (Perkin Elmer).

The table below summarizes biochemical data for Compounds 1-56. In the table below, for FGFR4 and pERK alphaLISA: "A" means that the IC$_{50}$ is less than 10 nM; "B" means the IC$_{50}$ is greater than or equal to 10 and less than 100 nM; "C" means that the IC$_{50}$ is greater than or equal to 100 and less than 1000 nM; "D" means that the IC$_{50}$ is greater than 1000 nM.

| Compound Number | FGFR4 IC$_{50}$ (nM) | pERK alphaLISA |
|---|---|---|
| 1 | C | |
| 2 | C | |
| 3 | D | |
| 4 | B | C |
| 5 | D | |
| 6 | D | |
| 7 | B | C |
| 8 | C | |
| 9 | A | B |
| 10 | A | B |
| 11 | B | |
| 12 | A | A |
| 13 | C | |
| 14 | D | |
| 15 | C | |
| 16 | B | |
| 17 | A | A |
| 18 | A | B |
| 19 | A | B |
| 20 | A | A |
| 21 | A | A |
| 22 | B | B |
| 23 | A | B |
| 24 | B | B |
| 25 | A | B |
| 26 | B | |
| 27 | B | B |
| 28 | A | B |
| 29 | B | |
| 30 | A | A |
| 31 | B | |
| 32 | A | B |
| 33 | C | |
| 34 | B | B |

-continued

| Compound Number | FGFR4 IC$_{50}$ (nM) | pERK alphaLISA |
|---|---|---|
| 35 | A | B |
| 36 | B | |
| 37 | A | |
| 38 | B | |
| 39 | A | A |
| 40 | A | A |
| 41 | A | |
| 42 | A | |
| 43 | A | |
| 44 | B | |
| 45 | A | |
| 46 | B | |
| 47 | A | B |
| 48 | B | |
| 49 | B | |
| 50 | A | B |
| 51 | B | |
| 52 | A | B |
| 53 | A | B |
| 54 | B | |
| 55 | B | |
| 56 | A | |

In the table above: "A" means that the IC$_{50}$ is less than 10 nM; "B" means the IC$_{50}$ is greater than or equal to 10 and less than 100 nM; "C" means that the IC$_{50}$ is greater than or equal to 100 and less than 1000 nM; "D" means that the IC$_{50}$ is greater than 1000 nM.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A compound of Formula Ib or a pharmaceutically acceptable salt thereof:

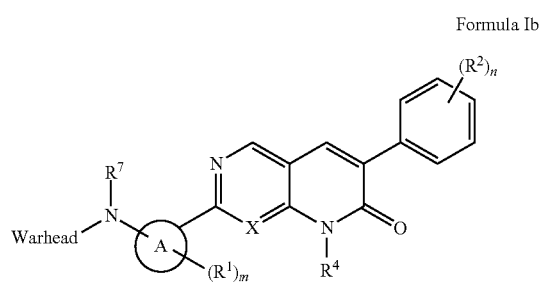

Formula Ib wherein:
Warhead is a moiety capable of forming a covalent bond with a nucleophile;
Ring A is a 5-8 membered aryl, 5-12 membered heteroaryl, 3-7 membered monocyclic or bicyclic heterocyclyl, or 3-12 membered monocyclic or bicyclic cycloalkyl group;
X is CH;
R$^4$ is H, C$_{1-6}$ alkyl, or 3-12 membered cycloalkyl;
each of R$^1$ and R$^2$ is independently halo, cyano, optionally substituted C$_{1-6}$ alkyl, optionally substituted C$_{1-6}$ alkoxy, hydroxy, oxo, amino, amido, alkyl urea, or optionally substituted 3-7 member heterocyclyl;
R$^7$ is hydrogen or C$_{1-6}$ alkyl, or R$^7$ together with Ring A forms a 8-12 membered bicyclic heterocyclyl optionally substituted with 1-5 occurrences of R$^1$;
m is 0, 1, 2, 3, 4, or 5; and
n is 0, 1, 2, 3, 4, or 5.

2. The compound of claim 1 or a pharmaceutically acceptable salt thereof, wherein:
Ring A is phenyl;
and m is 0, 1, 2, or 3.

3. The compound of claim 1 or a pharmaceutically acceptable salt thereof, wherein R$^7$ is hydrogen.

4. The compound of claim 1 or a pharmaceutically acceptable salt thereof, wherein R$^7$ together with Ring A forms an optionally substituted 8-12 membered bicyclic heterocyclyl.

5. The compound of claim 1 or a pharmaceutically acceptable salt thereof, wherein:
m is 1, 2, 3, 4, or 5; and
each R$^1$ is independently halo, optionally substituted C$_{1-6}$ alkyl, or optionally substituted C$_{1-6}$ alkoxy.

6. The compound of claim 1 or a pharmaceutically acceptable salt thereof, wherein n is 4, with two R$^2$ being halo and two R$^2$ being alkoxy.

7. The compound of claim 1 or a pharmaceutically acceptable salt thereof, wherein Warhead is selected from

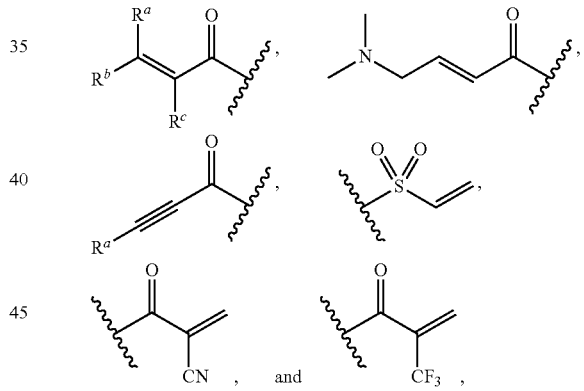

wherein each of R$^a$, R$^b$, and R$^c$ is independently hydrogen, optionally substituted C$_{1-4}$ alkyl, optionally substituted 3-12 membered cycloalkyl, or cyano.

8. The compound of claim 7 or a pharmaceutically acceptable salt thereof, wherein Warhead is

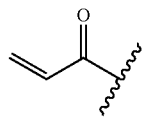

9. A pharmaceutical composition comprising a pharmaceutically acceptable carrier and a compound of claim 1 or a pharmaceutically acceptable salt thereof.

10. A method of treating a cancer mediated by FGFR-4, the method comprising administering to a subject in need thereof a therapeutically effective amount of compound of claim 1 or a pharmaceutically acceptable salt thereof, wherein the cancer is liver cancer, breast cancer, lung cancer, ovarian cancer, or a sarcoma.

11. A method of treating hepatocellular carcinoma mediated by FGFR-4, the method comprising administering to a subject a therapeutically effective amount of a compound of claim 1 or a pharmaceutically acceptable salt thereof.

12. A compound selected from any one of the following compounds and pharmaceutically acceptable salts thereof:

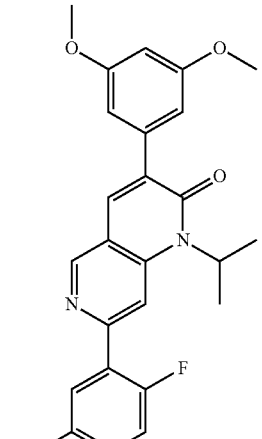

-continued
| Compound Number | Structure |
|---|---|
| 17 | 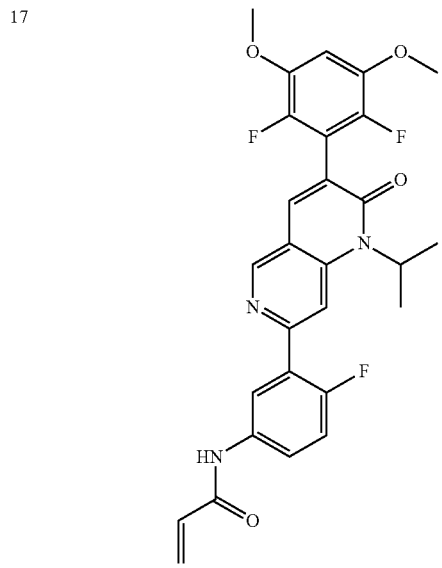 |
| 19 | 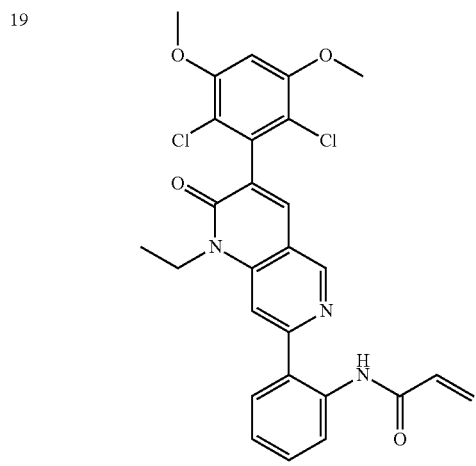 |
| 20 | 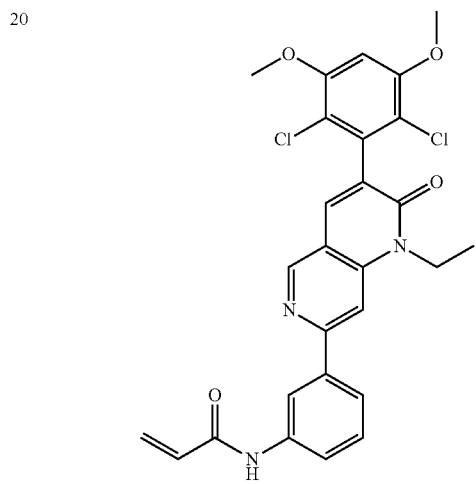 |
-continued
| Compound Number | Structure |
|---|---|
| 21 | 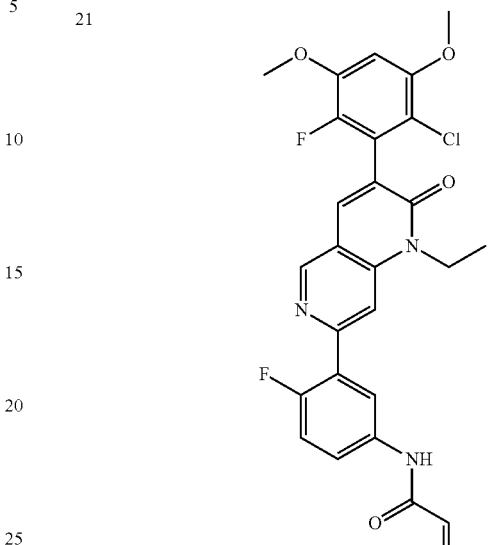 |
| 23 | 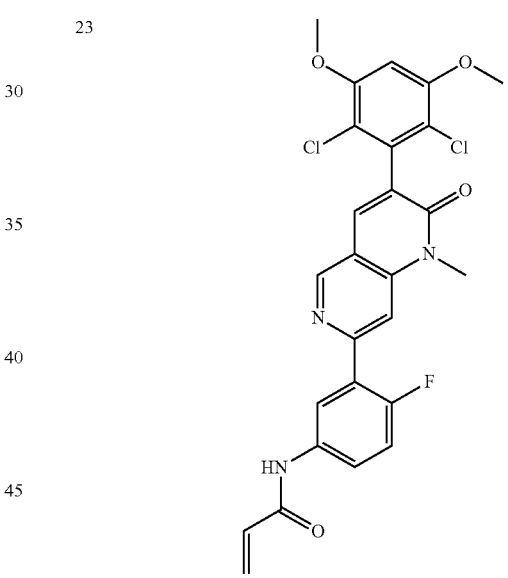 |
| 25 | 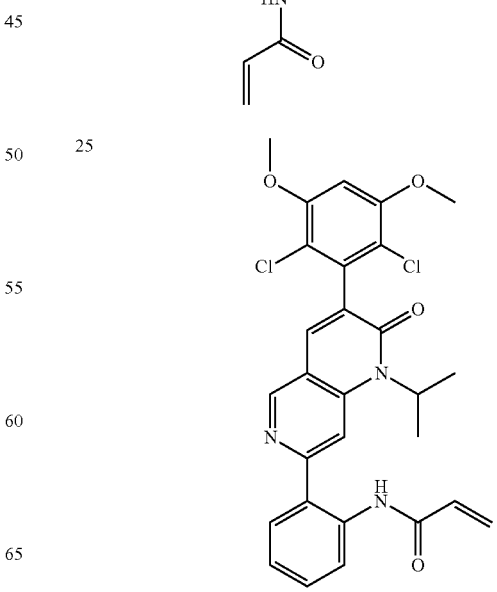 |

| Compound Number | Structure |
|---|---|
| 26 | 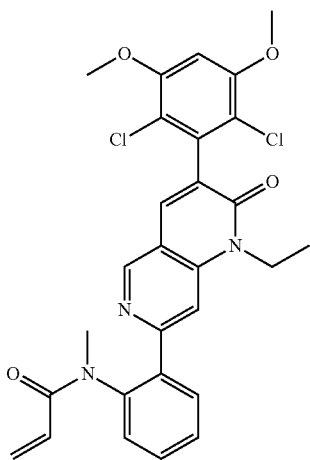 [SMILES: C=CC(=O)N(C)c1ccccc1-c1cc2c(cn1)cc(-c1c(Cl)c(OC)cc(OC)c1Cl)c(=O)n2CC] |
| 27 | 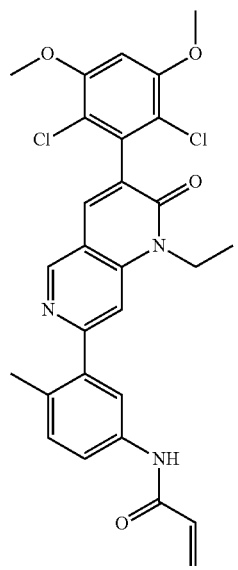 [SMILES: C=CC(=O)Nc1ccc(C)c(-c2cc3c(cn2)cc(-c2c(Cl)c(OC)cc(OC)c2Cl)c(=O)n3CC)c1] |
| 35 | 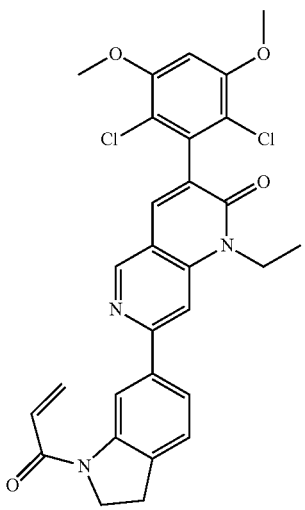 [SMILES: C=CC(=O)N1CCc2ccc(-c3cc4c(cn3)cc(-c3c(Cl)c(OC)cc(OC)c3Cl)c(=O)n4CC)cc21] |
| Compound Number | Structure |
|---|---|
| 37 | 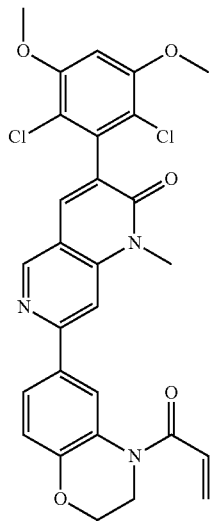 [SMILES: C=CC(=O)N1CCOc2ccc(-c3cc4c(cn3)cc(-c3c(Cl)c(OC)cc(OC)c3Cl)c(=O)n4C)cc21] |
| 39 | 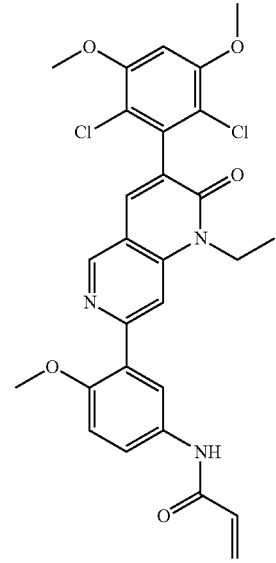 [SMILES: C=CC(=O)Nc1ccc(OC)c(-c2cc3c(cn2)cc(-c2c(Cl)c(OC)cc(OC)c2Cl)c(=O)n3CC)c1] |

-continued
| Compound Number | Structure |
|---|---|
| 40 | 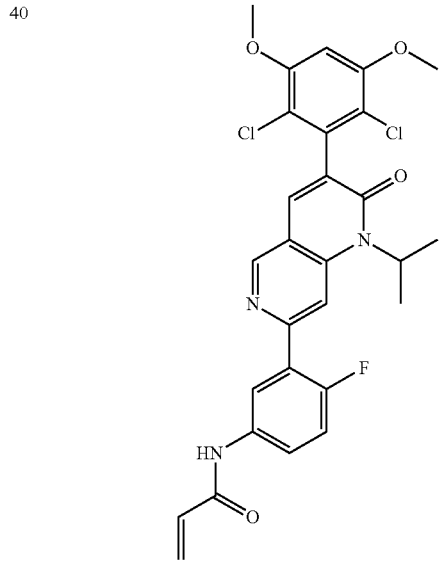 |
| 41 | 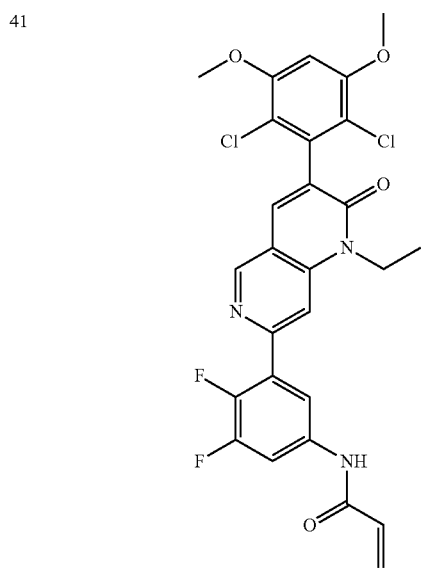 |
| 42 | 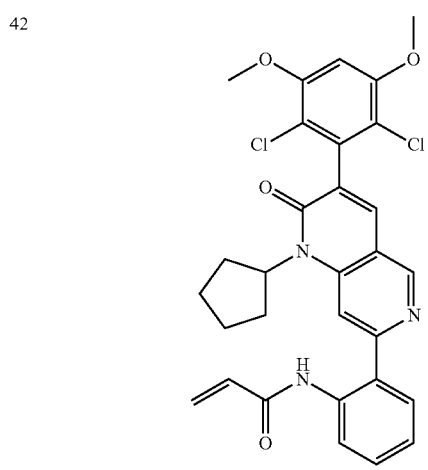 |
-continued
| Compound Number | Structure |
|---|---|
| 43 | 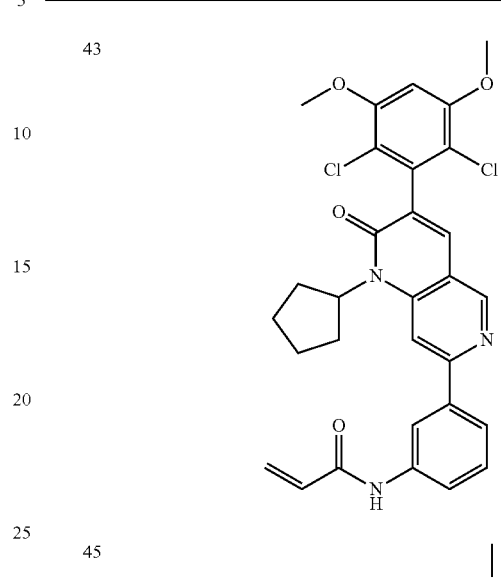 |
| 45 | 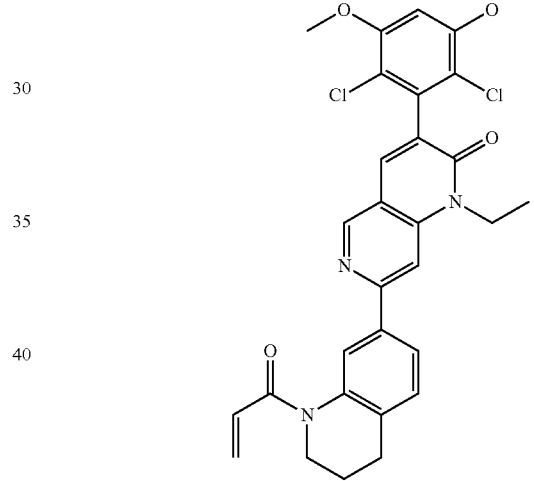 |
| 47 | 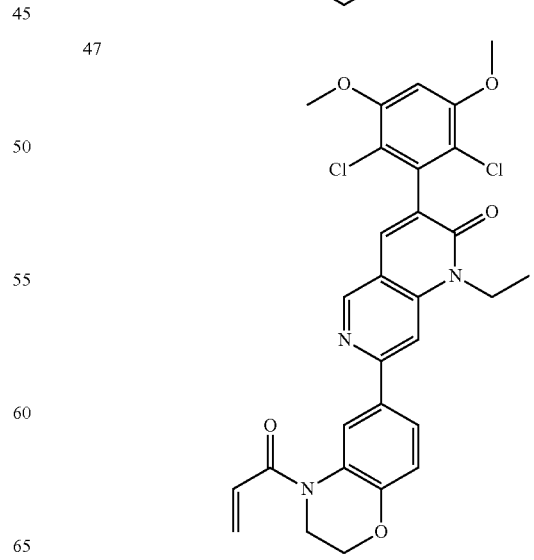 |

-continued
| Compound Number | Structure |
|---|---|
| 49 | 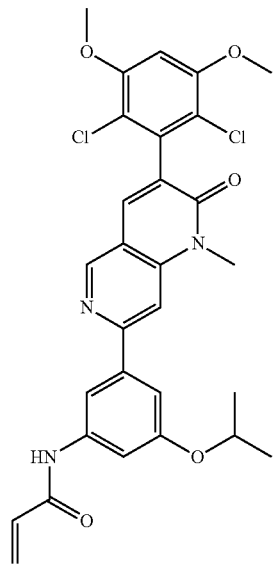 [SMILES: C=CC(=O)Nc1cc(OC(C)C)cc(-c2cc3c(cn2)cc(-c2c(Cl)c(OC)cc(OC)c2Cl)c(=O)n3C)c1] |
| 51 | 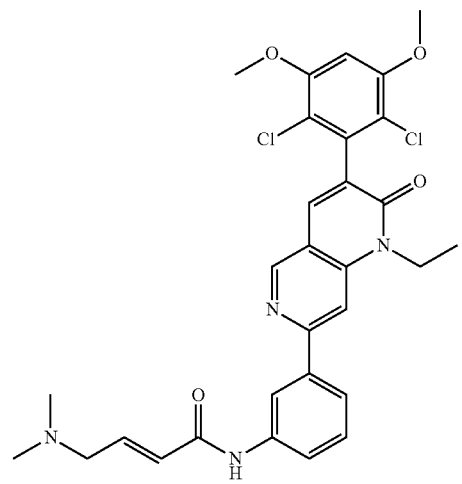 [SMILES: CCn1c(=O)c(-c2c(Cl)c(OC)cc(OC)c2Cl)cc2cnc(-c3cccc(NC(=O)/C=C/CN(C)C)c3)cc21] |
| 52 | 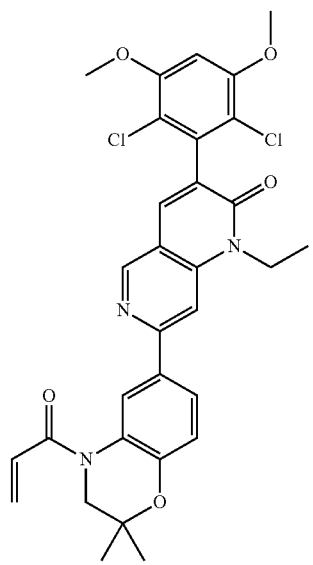 [SMILES: C=CC(=O)N1CC(C)(C)Oc2ccc(-c3cc4c(cn3)cc(-c3c(Cl)c(OC)cc(OC)c3Cl)c(=O)n4CC)cc21] |
-continued
| Compound Number | Structure |
|---|---|
| 53 | 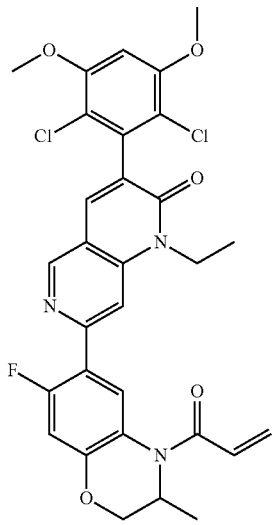 [SMILES: C=CC(=O)N1c2cc(-c3cc4c(cn3)cc(-c3c(Cl)c(OC)cc(OC)c3Cl)c(=O)n4CC)c(F)cc2OCC1C] |
| 54 | 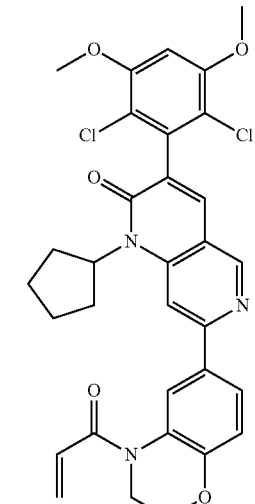 |
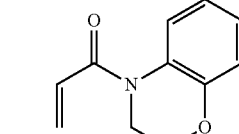
* * * * *